United States Patent
Haick et al.

(10) Patent No.: US 12,064,239 B2
(45) Date of Patent: Aug. 20, 2024

(54) DEVICE AND METHODS FOR DETECTION AND MONITORING OF TUBERCULOSIS

(71) Applicant: TECHNION RESEARCH & DEVELOPMENT FOUNDATION LIMITED, Haifa (IL)

(72) Inventors: Hossam Haick, Haifa (IL); Rotem Vishinkin, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 363 days.

(21) Appl. No.: 16/496,022

(22) PCT Filed: Mar. 22, 2018

(86) PCT No.: PCT/IL2018/050329
§ 371 (c)(1),
(2) Date: Sep. 20, 2019

(87) PCT Pub. No.: WO2018/173060
PCT Pub. Date: Sep. 27, 2018

(65) Prior Publication Data
US 2021/0282678 A1    Sep. 16, 2021

Related U.S. Application Data

(60) Provisional application No. 62/475,274, filed on Mar. 23, 2017.

(51) Int. Cl.
*A61B 5/145* (2006.01)
*A61B 5/00* (2006.01)
(Continued)

(52) U.S. Cl.
CPC ........ *A61B 5/14546* (2013.01); *A61B 5/0803* (2013.01); *A61B 5/14517* (2013.01); *A61B 5/4842* (2013.01); *G01N 33/497* (2013.01)

(58) Field of Classification Search
CPC .............. A61B 5/14546; A61B 5/0803; A61B 5/14517; A61B 5/4842; G01N 33/497
See application file for complete search history.

(56) References Cited

U.S. PATENT DOCUMENTS 5,817,012 A * 10/1998 Schoendorfer .... A61B 10/0035
600/362
6,773,926 B1    8/2004 Freund
(Continued)

FOREIGN PATENT DOCUMENTS

WO          9927357 A1    6/1999
WO    WO-2004081527 A2 *  9/2004 ........... G01N 27/624
(Continued)

OTHER PUBLICATIONS

Fend, R. et al. (2006). Prospects for clinical application of electronic-nose technology to early detection of *Mycobacterium* tuberculosis in culture and sputum. Journal of Clinical Microbiology, 44(6), 2039-2045. https://doi.org/10.1128/jcm.01591-05 (Year: 2006).*
(Continued)

*Primary Examiner* — Benjamin S Melhus
*Assistant Examiner* — Samuel C Kim
(74) *Attorney, Agent, or Firm* — RAPHAEL BELLUM PLLC

(57) ABSTRACT

Methods of diagnosing and/or monitoring tuberculosis (TB) in a subject by analyzing a test sample comprising at least one volatile organic compound (VOC) or semi-volatile organic compound (SVOC) emitted or excreted from the skin of the subject. The test sample can be analyzed by a sensing unit comprising nanomaterials- and/or polymer-based sensors. Further provided is a skin-mountable device comprising a fixing unit and said sensing unit. Also discloses a method of diagnosing and/or monitoring tuberculosis,
(Continued)

comprising analyzing specific skin-emitted VOCs or SVOCs, which are indicative of tuberculosis in a subject.

10 Claims, 6 Drawing Sheets

(51) Int. Cl.
    *A61B 5/08*     (2006.01)
    *G01N 33/497*     (2006.01)

(56) References Cited

U.S. PATENT DOCUMENTS

| | | | |
|---|---|---|---|
| 8,366,630 B2 | 2/2013 | Haick | |
| 8,481,324 B2 | 7/2013 | Haick | |
| 2003/0159927 A1 | 8/2003 | Lewis | |
| 2004/0006257 A1 | 1/2004 | Burch | |
| 2004/0127808 A1 | 7/2004 | Vaughan | |
| 2005/0101841 A9 | 5/2005 | Kaylor | |
| 2007/0062255 A1 | 3/2007 | Talton | |
| 2008/0150556 A1* | 6/2008 | Han | B82Y 15/00 977/762 |
| 2009/0239252 A1 | 9/2009 | Trevejo | |
| 2009/0308742 A1* | 12/2009 | Paranjape | A61B 5/14546 204/403.14 |
| 2010/0137733 A1 | 6/2010 | Wang | |
| 2010/0248268 A1 | 9/2010 | Woods | |
| 2010/0291617 A1 | 11/2010 | Trevejo | |
| 2010/0318070 A1* | 12/2010 | Mitra | A61F 13/15203 604/540 |
| 2011/0098591 A1 | 4/2011 | Haick | |
| 2011/0269632 A1 | 11/2011 | Haick | |
| 2012/0245434 A1 | 9/2012 | Haick | |
| 2012/0245854 A1 | 9/2012 | Haick | |
| 2013/0034910 A1 | 2/2013 | Haick | |
| 2013/0059758 A1 | 3/2013 | Haick | |
| 2013/0143247 A1 | 6/2013 | Haick | |
| 2013/0150261 A1 | 6/2013 | Haick | |
| 2014/0303462 A1* | 10/2014 | Ellenberger-Girard | A61B 5/0205 600/314 |
| 2014/0330138 A1* | 11/2014 | Banet | A61B 5/743 600/484 |
| 2015/0301021 A1 | 10/2015 | Haick | |
| 2016/0058364 A1* | 3/2016 | Ionescu | A61B 5/07 600/301 |

FOREIGN PATENT DOCUMENTS

| | | | |
|---|---|---|---|
| WO | 2009066293 A1 | 5/2009 |
| WO | 2010079491 A1 | 7/2010 |
| WO | 2011148371 A1 | 12/2011 |
| WO | 2014068554 A1 | 5/2014 |

OTHER PUBLICATIONS

Liang, K., Dodabalapur, A., & amp; Sharma, D. (2016). Technical papers and presentations. COMSOL. www.comsol.com/paper/multiple-mode-polymeric-silicon-dual-channel-gas-sensors-37212 (Year: 2016).*

Abaffy et al., (2010) Differential volatile signatures from skin, naevi and melanoma: a novel approach to detect a pathological process. PLoS One 5(11): e13813; 12 pages.

Abdi (2010) Partial least squares regression and projection on latent structure regression (PLS Regression). WIREs Computational Statistics 2(1): 97-106.

Altomare et al., (2013) Exhaled volatile organic compounds identify patients with colorectal cancer. Br J Surg 100(1): 144-150.

Bajtarevic et al., (2009) Noninvasive detection of lung cancer by analysis of exhaled breath. BMC Cancer 9: 348; 16 pages.

Banday et al., (2011) Use of Urine Volatile Organic Compounds to Discriminate Tuberculosis Patients from Healthy Subjects. Anal Chem 83(14): 5526-5534.

Barash et al., (2009) Sniffing the Unique "Odor Print" of Non-Small-Cell Lung Cancer with Gold Nanoparticles. Small 5(22): 2618-2624.

Barash et al., (2012) Classification of lung cancer histology by gold nanoparticle sensors. Nanomedicine: Nanotechnology, Biology and Medicine 8(5): 580-589.

Barbieri et al., (2005) Determination of microbial volatile organic compounds from *Staphylococcus* pasteuri against Tuber borchii using solid-phase microextraction and gas chromatography/ion trap mass spectrometry. Rapid Commun Mass Spectrom 19(22): 3411-3415.

Brust and Kiely (2002) Some recent advances in nanostructure preparation from gold and silver particles: a short topical review. Colloids and Surfaces A: Physicochemical and Engineering Aspects 202(2-3): 175-186.

Brust et al., (1994) Synthesis of thiol-derivatised gold nanoparticles in a two-phase Liquid-Liquid system. J Chem Soc Chem Commun 7: 801-802.

Buszewski et al., (2007) Human exhaled air analytics: biomarkers of diseases. Biomedical Chromatography 21(6): 553-566.

Chambers et al., (2011) Novel diagnostics: progress toward a breath test for invasive Aspergillus fumigatus. Med Mycol 49 Suppl 1: S54-S61.

Chen et al., (2007) A study of the volatile organic compounds exhaled by lung cancer cells in vitro for breath diagnosis. Cancer 110(4): 835-844.

Chigona et al., (2012) A review on mHealth research in developing countries. The Journal of Community Informatics 9(2). Retrieved from http://ci-journal.net/index.php/ciej/article/view/941; 10 pages.

D'Amico et al., (2010) An investigation on electronic nose diagnosis of lung cancer. Lung Cancer 68(2): 170-176.

De Gennaro et al., (2010) Chemical characterization of exhaled breath to differentiate between patients with malignant plueral mesothelioma from subjects with similar professional asbestos exposure. Anal Bioanal Chem 398(7-8): 3043-3050.

Dummer et al., (2011) Analysis of biogenic volatile organic compounds in human health and disease. TrAC Trends in Analytical Chemistry 30(7): 960-967.

Fend et al., (2006) Prospects for clinical application of electronic-nose technology to early detection of *Mycobacterium* tuberculosis in culture and sputum. J Clin Microbiol 44(6): 2039-2045.

Filipiak et al., (2008) Release of volatile organic compounds (VOCs) from the lung cancer cell line CALU-1 in vitro. Cancer Cell Int 8: 17; 11 pages.

Filipiak et al., (2015) Breath analysis for in vivo detection of pathogens related to ventilator-associated pneumonia in intensive care patients: a prospective pilot study. J Breath Res 9(1): 016004; 16 pages.

Gallagher et al., (2008) Analyses of volatile organic compounds from human skin. Br J Dermatol 159(4): 780-791.

Hakim et al., (2012) Volatile Organic Compounds of Lung Cancer and Possible Biochemical Pathways. Chem Rev 112(11): 5949-5966.

Hanouneh et al., (2014) The Breathprints in Patients with Liver Disease Identify Novel Breath Biomarkers in Alcoholic Hepatitis. Clin Gastroenterol Hepatol 12(3): 516-523.

Hostetler et al., (1998) Alkanethiolate Gold Cluster Molecules with Core Diameters from 1.5 to 5.2 nm: Core and Monolayer Properties as a Function of Core Size. Langmuir 14(1): 17-30.

Huynh et al., (2016) Composites of Polymer and Carbon Nanostructures for Self-Healing Chemical Sensors. Advanced Materials Technologies 1(9): 1600187; 8 pages.

Huynh et al., (2017) Advanced Materials for Use in Soft Self-Healing Devices. Adv Mater 29(19): 1604973; 14 pages.

Ibañez and Zamborini (2012) Chemiresistive Sensing with Chemically-Modified Metal and Alloy Nanoparticles. Small 8(2): 174-202.

Ionescu et al., (2011) Detection of multiple sclerosis from exhaled breath using bilayers of polycyclic aromatic hydrocarbons and single-wall carbon nanotubes. ACS Chem Neurosci 2(12): 687-693.

Joseph et al., (2008) Gold Nanoparticle/Organic Networks as Chemiresistor Coatings: The Effect of Film Morphology on Vapor Sensitivity. J Phys Chem C 112(32): 12507-12514.

(56) References Cited

OTHER PUBLICATIONS

Kneepkens et al., (1994) The potential of the hydrocarbon breath test as a measure of lipid peroxidation. Free Radic Biol Med 17(2): 127-160 with erratum.
Konvalina and Haick (2012) Effect of Humidity on Nanoparticle-Based Chemiresistors: A Comparison between Synthetic and Real-World Samples. ACS Appl Mater Interfaces 4(1): 317-325.
Lalvani and Pareek (2010) A 100 year update on diagnosis of tuberculosis infection. Br Med Bull 93: 69-84.
Lechner and Rieder (2007) Mass spectrometric profiling of low-molecular-weight volatile compounds—diagnostic potential and latest applications. Curr Med Chem 14(9): 987-995.
Lorwongtragool et al., (2014) A novel wearable electronic nose for healthcare based on flexible printed chemical sensor array. Sensors (Basel) 14(10): 19700-19712.
Martinez et al., (2008) Tuberculosis and air travel: WHO guidance in the era of drug-resistant TB. Travel Med Infect Dis 6(4): 177-181.
Mgode et al., (2012) *Mycobacterium* tuberculosis volatiles for diagnosis of tuberculosis by Cricetomys rats. Tuberculosis (Edinb) 92(6): 535-542.
Miekisch et al., (2004) Diagnostic potential of breath analysis—focus on volatile organic compounds. Clin Chim Acta 347(1-2): 25-39.
Nakhleh et al., (2014) Detecting active pulmonary tuberculosis with a breath test using nanomaterial-based sensors. Eur Respir J 43(5): 1522-1525.
Naraghi et al., (2010) Use of volatile fingerprints for rapid screening of antifungal agents for efficacy against dermatophyte *Trichophyton* species. Sensors and Actuators B: Chemical 146(2): 521-526.
Nawrath et al., (2012) The volatiles of pathogenic and nonpathogenic mycobacteria and related bacteria. Beilstein J Org Chem 8: 290-299.
Pande et al., (2015) Using Smartphone Sensors for Improving Energy Expenditure Estimation. IEEE J Transl Eng Health Med 3: 2700212; 12 pages.
Peled et al. (2012) Detection of volatile organic compounds in cattle naturally infected with *Mycobacterium* bovis. Sensors and Actuators B: Chemical 171-172: 588-594.
Peng et al., (2008) Detecting simulated patterns of lung cancer biomarkers by random network of single-walled carbon nanotubes coated with nonpolymeric organic materials. Nano Lett 8(11): 3631-3635.
Peng et al., (2009) Diagnosing lung cancer in exhaled breath using gold nanoparticles. Nat Nanotechnol 4(10): 669-673.
Peng et al., (2012) Detection of lung, breast, colorectal, and prostate cancers from exhaled breath using a single array of nanosensors. Br J Cancer 103(4): 542-551.
Pennazza et al., (2011) Monitoring of melanoma released volatile compounds by a gas sensors array: From in vitro to in vivo experiments. Sensors and Actuators B: Chemical 154(2): 288-294.
Phillips et al., (1999) Volatile organic compounds in breath as markers of lung cancer: a cross-sectional study. Lancet 353(9168): 1930-1933.
Phillips et al., (2003) Breath markers of oxidative stress in patients with unstable angina. Heart Dis 5(2): 95-99.
Phillips et al., (2006) Prediction of breast cancer using volatile biomarkers in the breath. Breast Cancer Res Treat 99(1): 19-21.
Phillips et al., (2007) Volatile biomarkers of pulmonary tuberculosis in the breath. Tuberculosis (Edinb) 87(1): 44-52.
Phillips et al., (2010) Breath biomarkers of active pulmonary tuberculosis. Tuberculosis (Edinb) 90(2): 145-151.
Phillips et al., (2012) Point-of-care breath test for biomarkers of active pulmonary tuberculosis. Tuberculosis (Edinb) 92(4): 314-320.
Poli et al., (2005) Exhaled volatile organic compounds in patients with non-small cell lung cancer: cross sectional and nested short-term follow-up study. Respir Res 6: 71; 10 pages.
Rawat et al., (2015) Towards efficient disaster management: 5G and Device to Device communication. 2nd International Conference on Information and Communication Technologies for Disaster Management (ICT-DM), Rennes, France. Nov. 30-Dec. 2, 2015; pp. 79-87, IEEE.
Riazanskaia et al., (2008) The analytical utility of thermally desorbed polydimethylsilicone membranes for in-vivo sampling of volatile organic compounds in and on human skin. Analyst 133(8): 1020-1027.
Röck et al., (2008) Electronic nose: current status and future trends. Chem Rev 108(2): 705-725.
Sahgal et al., (2006) *Trichophyton* species: use of volatile fingerprints for rapid identification and discrimination. Br J Dermatol 155(6): 1209-1216.
Segev-Bar et al., (2012) Effect of perforation on the sensing properties of monolayer-capped metallic nanoparticle films. J Phys Chem C 116(29): 15361-15368.
Segev-Bar et al., (2013) Tunable touch sensor and combined sensing platform: toward nanoparticle-based electronic skin. ACS Appl Mater Interfaces 5(12): 5531-5541.
Shao et al., (2011) Recent patents on nanosensor for tumor biomarker detection. Nano Biomedicine & Engineering 3(1): 66-72.
Shuster et al., (2011) Classification of breast cancer precursors through exhaled breath. Breast Cancer Research and Treatment 126(3): 791-796.
Stetter et al., (2000) New sensor arrays and sampling systems for a modular electronic nose. Sensors and Actuators B: Chemical 69(3): 410-419.
Syhre and Chambers (2008) The scent of *Mycobacterium* tuberculosis. Tuberculosis (Edinb) 88(4): 317-323.
Syhre et al., (2009) The scent of *Mycobacterium* tuberculosis—part II breath. Tuberculosis (Edinb) 89(4): 263-266.
Tisch and Haick (2010) Arrays of chemisensitive monolayer-capped metallic nanoparticles for diagnostic breath testing. Reviews in Chemical Engineering 26(5-6): 171-179.
Tisch and Haick (2010) Chapter 4: Sensors Based on Monolayer-Capped Metallic Nanoparticles. In: Chemical Sensors—Fundamentals of Sensing Materials; vol. 2: Nanostructured Materials. Edited by Korotcenkov G. Momentum Press, LLC, New York, USA, pp. 141-202.
Tisch and Haick (2010) Nanomaterials for cross-reactive sensor arrays. MRS Bull 35(10): 797-803.
Turner (2011) Potential of breath and skin analysis for monitoring blood glucose concentration in diabetes. Expert Rev Mol Diagn 11(5): 497-503.
Vishinkin and Haick; "Self-Administered Adhesive Patch for Detection of Tuberculosis". The 52nd Annual Meeting of the Israel Institute of Chemical Engineers. Jun. 26, 2017, Tel Aviv, Israel. Retrieved from the Internet <URL:https://bioforumconf.com/IICHE-abs/outofhtml/IICHE_2017/self-administer_Rotem_Vishinkin. html> Jun. 26, 2017 (Jun. 26, 2017) on Jul. 15, 2018; 2 pages.
Wood et al., (2006) Analysis of Volatile Bacterial Metabolites by Gas Chromatography—Mass Spectrometry. Spectroscopy 21(6): 20-28.
Zhao et al., (1997) Soft lithographic methods for nano-fabrication. J Mater Chem 7(7): 1069-1074.
Zhu et al., (2010) Fast detection of volatile organic compounds from bacterial cultures by secondary electrospray ionization-mass spectrometry. J Clin Microbiol 48(12): 4426-4431.
Zilberman et al., (2009) Spongelike structures of hexa-peri-hexabenzocoronene derivatives enhance the sensitivity of chemiresistive carbon nanotubes to nonpolar volatile organic compounds of cancer. Langmuir 25(9): 5411-5416.
Zilberman et al., (2010) Carbon nanotube/hexa-peri-hexabenzocoronene bilayers for discrimination between nonpolar volatile organic compounds of cancer and humid atmospheres. Adv Mater 22(38): 4317-4320.
Zilberman et al., (2011) Nanoarray of Polycyclic Aromatic Hydrocarbons and Carbon Nanotubes for Accurate and Predictive Detection in Real-World Environmental Humidity. ACS Nano 5(8): 6743-6753.

\* cited by examiner

DEVICE AND METHODS FOR DETECTION AND MONITORING OF TUBERCULOSIS

FIELD OF THE INVENTION

The present invention provides a technology for detecting and monitoring tuberculosis based on the sensing of volatile or semi-volatile organic compounds emitted or excreted from skin.

BACKGROUND OF THE INVENTION

Tuberculosis (TB) is a common infectious disease caused by mycobacterium, mainly *M. tuberculosis*. *M. tuberculosis* is an aerobe bacterium which usually attacks the lungs (as pulmonary TB) but can also affect other organs and systems such as: bones, joints, genitourinary system, central nervous system, the circulatory system, the lymphatic system, and even the skin. TB is easily spread by airborne transmission of small droplets, e.g. through cough, sneeze and spit.

The symptoms and physical findings of an active TB are not specific and may be related to other diseases—a fact which leads to delayed diagnosis and further spreading of TB. In 2012, there were 8.6 million new TB cases, and a total of 1.3 million deaths from TB. About 95% of TB cases occur in developing countries, where individuals live on less than $1 per day.

Currently there are several diagnostic methods, such as, sputum smear microscopy, TB culture from sputum and Xpert MTB/RIF for the detection of active TB. However, these methods have limitations especially in developing countries.

Nucleic acid amplification tests (NAATs) that identify *M. tuberculosis* in respiratory system within 2-7 hours and interferon γ release assay are two of the more recently developed methods for TB diagnosis. These methods are considered to be more rapid, accurate and sensitive. However, the equipment used in these methods is expensive and it requires technical expertise and/or the testing requires the use of radioactive materials and their disposal. Hence, the current diagnostic techniques are either inaccurate and time consuming, or are expensive and demand highly sophisticated laboratories which are not available in resource-poor and developing countries.

Because of their potential role in the diagnosis of pulmonary diseases, exhaled Volatile Organic Compounds (VOCs) have captured an increased interest in recent years. Chemical analysis, including specific identification and quantification of VOCs in breath samples, has revealed key differences between breath compositions of patients afflicted with several pulmonary diseases as compared to control samples. These pulmonary diseases include asthma, chronic obstructive pulmonary disease, cystic fibroses and lung cancer (WO 2010/079491; U.S. 2013/143247; and U.S. 2013/150261).

VOCs can be detected from samples of bodily fluids or the headspace of a container containing infected cells and/or tissues or directly from exhaled breath in which disease-related changes are reflected through exchange via the blood or directly via the lung airways (Zhu et al., J. Clic. Microbiol., 48, 4426-4431 (2010); and Naraghi et al., Sens. Actuat. B, 146, 521-526 (2010); Abaffy et al., PLOS ONE, 5(11), e13813, doi:10.1371/journal.pone.0013813 (2010); Sahgal et al., Br. J. Dermatol., 155, 1209-1216 (2006); Turner, Exp. Rev. Mol. Diag., 11, 497-503 (2011); and Pennazza et al., Sens. Actuat. B, 154, 288-294 (2011)).

Specific alterations in VOC compositions of urine and breath samples of TB positive individuals have been reported (Banday et al., Anal. Chem., 83(14), 5526-5534 (2011)). Phillips et al. used gas-chromatography linked with mass spectrometry (GC-MS) to identify TB-related VOCs, part of which was found in *M. tuberculosis* cultures (Tuberculosis, 90, 145-151 (2010); and Tuberculosis, 87, 44-52 (2007)). Analyzing these VOCs using pattern recognition algorithms provided the accurate classification of 80-84% of the samples (Phillips et al., Tuberculosis, 92, 314-320 (2012)). Banday et al. showed significant alterations in VOCs concentrations in urine samples collected from TB patients using GC-MS (Anal. Chem., 83, 5526-5534 (2011)).

The use of GC-MS analysis for the detection of VOCs as breath biomarkers for TB has several disadvantages for use in clinical point-of-care applications. In particular, this technique utilizes bulky equipment which is relatively expensive and complicated to operate. In addition, it involves a pre-concentrating step which increases the risk of contamination and/or loss of analytes (Buszewski et al., Biomed. Chromatogr., 21, 553-566 (2007)). Furthermore, the accuracy obtained in these measurements is relatively low and it does not meet the criterion which is required for a TB screening test. Syhre et al. used GC-MS for specific detection of nicotinic acid as an indication for active TB (Tuberculosis, 89, 263-266 (2009)). The method required the in-vitro methylation of the nicotinic acid prior to measurements. Furthermore, this method could not provide reliable results for smoking individuals. Peled et al. identified unique VOCs or a VOC profile in the breath of cattle infected with *M. bovis* (bovine tuberculosis) using GC-MS analysis. The unique profile of VOCs was used to design a nanotechnology-based array of sensors for detection of *M. bovis*-infected cattle via breath (Sens. Actuat. B, 171-172, 588-594 (2012); FIG. 11).

U.S. 2010/0291617 and U.S. 2009/0239252 disclose methods and devices for identifying *M. tuberculosis* bacteria in a sample comprising the detection of one or more volatile organic compounds indicative of a presence of or response to treatment or resistance of the *M. tuberculosis* bacteria in the sample.

U.S. 2010/0137733 discloses a method for detecting whether a subject has tuberculosis or monitoring a tuberculosis subject, said method comprising: contacting breath from said subject with an apparatus, said apparatus having a gas chromatograph, wherein said gas chromatograph is fluidly coupled to a detector array to produce a signal; and analyzing said signal from the detector array to determine whether said subject has tuberculosis.

U.S. 2007/0062255 discloses an apparatus for collecting and detecting compounds in a human breath sample comprising: a handheld sample collector comprising a sorbent phase; a breath analyzer comprising a thermal desorption column; two or more sensors for detection of breath compounds; and a flow controller for controlling the transfer of breath compounds from the sample collector into the breath analyzer, wherein the handheld sample collector and breath analyzer are configured for fluid communication with each other so that breath compounds from the sample collector can pass into the breath analyzer for detection.

A promising approach for the detection and classification of TB relies on the detection of volatile organic compounds (VOCs) that are linked with TB, and so, the detection of tuberculosis was demonstrated by Nakhleh et al. (Nakhleh et al. Eur. Resp. J. 2014, 43, 1519-1522) through detection of VOCs, achieving 90% sensitivity, 93% specificity and 92% accuracy in discrimination between healthy and TB infected patients using electronic nose devices with a single sensor.

WO 2014/068554 to some of the inventors of the present invention discloses a sensor for diagnosing tuberculosis caused by *M. tuberculosis* bacteria in a subject, which comprises at least one of gold nanoparticles coated with dodecanethiol and single walled carbon nanotubes coated with 2-methyl-2-butene. Said publication further provides a method of diagnosing tuberculosis comprising, inter alia, exposing said sensor to a test sample selected from exhaled breath and at least one bodily fluid or secretion of the subject and measuring an electrical signal upon exposure of the sensor to the test sample.

However, to date, the use of the techniques based on the detection of VOCs has been impeded by the need for moderately to highly expensive equipment, the high levels of expertise required to operate such instruments, the time required for sampling and analysis, and the need for pre-concentration techniques. Moreover, the current methods can detect TB only in laboratory conditions and not in real time and cannot continuously monitor the health condition of the person. There exists, therefore, an unmet need for a portable and user-friendly device, which would allow real-time diagnosing and monitoring of tuberculosis.

SUMMARY OF THE INVENTION

The present invention is directed to methods and medical devices for diagnosing and/or monitoring of tuberculosis. The medical device of the present invention utilizes a nanosensor technology incorporating conductive nanostructures and/or polymers for the detection of volatile organic compounds (VOCs) or semi-volatile organic compounds (SVOCs), which are indicative of active tuberculosis in a subject. The present invention is based in part on an unexpected finding that VOCs and SVOCs, which can be used as TB biomarkers are excreted by human skin. The inventors have therefore developed a skin-mountable medical device comprising tailored nanosensors which detect skin-emitted or skin-excreted VOCs and SVOCs indicative of tuberculosis with a detection limit, which allows fast and reliable diagnosing of pulmonary tuberculosis. Various sensors which can be used in the skin-mountable medical devices according to the principles of the invention showed 100% sensitivity and at least about 85% accuracy in diagnosing active tuberculosis. The medical device according to the principles of the invention offers direct analysis of the VOCs and SVOCs emitted or excreted from the skin upon which the device is placed and does not require obtaining and handling a test sample.

Accordingly, the method of diagnosing and monitoring TB utilizing the medical devices of the present invention does not involve the use of expensive laboratory equipment and does not require any special medical or technical skills, such that it can be performed independently and routinely by the end user. Said method enables real-time diagnosing and/or monitoring of the state of the disease. The medical devices of the present invention can be configured to communicate with each other and/or with remote servers or portable electronic devices, thereby enabling even more accurate evaluation of the state of the disease, collection of TB-related information, mapping disease spread and alerting the population of TB-infection risk in real-time.

The present invention further provides non-real time methods of diagnosing and monitoring pulmonary tuberculosis by analyzing skin-emitted or skin-excreted VOCs or SVOCs, wherein said analysis can be performed, inter alia, by the nanosensors comprising conductive nanostructures and/or polymers or by gas chromatography.

In one aspect, there is provided a method of diagnosing and/or monitoring pulmonary tuberculosis (TB) in a subject, the method comprising the steps of: obtaining a test sample comprising at least one volatile organic compound (VOC) or semi-volatile organic compound (SVOC) excreted from or emitted from the skin of the subject; providing a sensing unit comprising at least one sensor comprising a material selected from the group consisting of conductive nanostructures coated with an organic coating, a conducting polymer and a conductive polymer composite; exposing the at least one sensor to the test sample; measuring an output signal of the at least one sensor upon exposure thereof to the test sample; and diagnosing pulmonary tuberculosis if the signal is greater than a reference value.

In some embodiments, the step of obtaining a test sample comprises placing an absorbent material on the skin of the subject for a predetermined period of time. In some embodiments, the step of obtaining a test sample further comprises retrieving the at least one VOC or SVOC from the absorbent material.

In some embodiments, the conductive nanostructures coated with an organic coating are selected from gold nanoparticles (GNPs) coated with a thiol or a disulfide and single walled carbon nanotubes (SWCNTs) coated with polycyclic aromatic hydrocarbon (PAH). Each possibility represents a separate embodiment of the invention.

In some embodiments, the thiol is selected from the group consisting of 3-ethoxythiophenol, 2-ethoxythiophenol, decanethiol, 2-nitro-4-(trifluoromethyl)benzenethiol, butanethiol, benzyl mercaptan, octadecanethiol, 2-naphthalenethiol, 4-chlorobenzenemethanethiol, dodecanethiol, tert-dodecanethiol, 2-ethyl hexanethiol, hexanethiol, octadecanethiol, 1-methyl-2-imidazolethiol, and combinations thereof. Each possibility represents a separate embodiment of the invention. In some embodiments, the disulfide comprises dibutyl disulfide.

In some embodiments, the polycyclic aromatic hydrocarbon comprises hexa-perihexabenzocoronene or a derivative thereof. In certain embodiments, the polycyclic aromatic hydrocarbon comprises crystal hexakis(n-dodecyl)-peri-hexabenzocoronene (HBC—C12).

In some embodiments, the conducting polymer is selected from the group consisting of diketopyrrolopyrrole-naphthalene copolymer (PDPP-TNT), polydiketopyrrolopyrrole, polyaniline (PANT), polythiophene, poly(3,4-ethylenedioxythiophene)-poly(styrene-sulfonate) (PEDOT:PSS), polypyrrole, and derivatives and combinations thereof. Each possibility represents a separate embodiment of the invention.

In some embodiments, the conductive polymer composite comprises a disulfide polymer mixed with carbon black, wherein the disulfide polymer is selected from poly(propylene-urethaneureaphenyl-disulfide), poly(urethane-carboxyphenyl-disulfide) and combinations thereof. Each possibility represents a separate embodiment of the invention.

In some embodiments, the at least one sensor comprises SWCNTs coated with crystal hexakis(n-dodecyl)-peri-hexabenzocoronene (HBC—C12) or decanethiol-coated GNPs.

In some embodiments, the sensing unit comprises a sensor array. In further embodiments, the sensor array comprises a combination of sensors selected from the group consisting of: decanethiol-coated GNPs and hexanethiol-coated GNPs; decanethiol-coated GNPs and dodecanethiol-coated GNPs; octadecanethiol-coated GNPs and decanethiol-coated GNPs; PDPP-TNT and 2-nitro-4-(trifluoromethyl)benzenethiol-coated GNPs; PDPP-TNT, tert-dodecanethiol-coated GNPs, and 3-ethoxythiophenolcoated GNPs; decanethiol-coated GNPs, PDPP-TNT, and dodecanethiol-coated GNPs; 2-nitro-4-(trifluoromethyl)benzenethiol-coated GNPs, 3-ethoxythiophenol-coated GNPs, and 2-ethylhexanethiol-coated GNPs; 2-ethylhexanethiol-coated GNPs, dibutyl disulfide-coated GNPs, and 3-ethoxythiophenol-coated GNPs; HBC—C12, 2-naphthalenethiol-coated GNPs, and PDPP-TNT; octadecanethiol-coated GNPs, benzyl mercaptan-coated GNPs and 2-ethylhexanethiol-coated GNPs; 3-ethoxythiophenol-coated GNPs, tert-dodecanethiol-coated GNPs, and 4-chlorobenzenemethanethiol-based GNPs; PDPP-TNT, decanethiol-coated GNPs and dibutyl disulfide-coated GNPs; dibutyl-disulfide-coated GNPs, a composite of carbon black with poly(propylene-urethaneureaphenyl-disulfide) and 2-naphthalenethiol-based GNPs; 2-ethyl hexanethiol-coated GNPs, decanethiol-coated GNPs, dibutyl disulfide-coated GNPs and 3-ethoxythiophenol-coated GNPs; 3-ethoxythiophenol-coated GNPs, dibutyl disulfide-coated GNPs, 2-nitro-4-(trifluoromethyl)benzenethiol-coated GNPs and 2-ethylhexanethiol-coated GNPs; benzyl mercaptan-coated GNPs, 3-ethoxythiophenol-coated GNPs, octadecanethiol-coated GNPs and 2-ethylhexanethiol-coated GNPs; tert-dodecanethiol-coated GNPs, benzyl mercaptan-coated GNPs, HBC—C12 and 2-ethylhexanethiol-coated GNPs; decanethiol-coated GNPs, tert-dodecanethiol-coated GNPs, 2-nitro-4-(trifluoromethyl)benzenethiol-coated GNPs, and 2-ethylhexanethiol-coated GNPs; HBC—C12, a composite of black carbon with poly(propylene-urethaneureaphenyl-disulfide) mixed with poly(urethane-carboxyphenyl-disulfide), 2-ethylhexanethiol-coated GNPs and PDPP-TNT; Tert-dodecanethiol-coated GNPs, decanethiol-coated GNPs, 3-ethoxythiophenol coated GNPs, HBC—C12, a composite of black carbon with poly(propylene-urethaneureaphenyl-disulfide) mixed with poly(urethane-carboxyphenyl-disulfide); a composite of carbon black with poly(propylene-urethaneureaphenyl-disulfide), tert-dodecanethiol-coated GNPs, and a composite of black carbon with poly(propylene-urethaneureaphenyl-disulfide) mixed with poly(urethane-carboxyphenyl-disulfide), 2-ethylhexanethiol-coated GNPs; a composite of carbon black with poly(propylene-urethaneureaphenyl-disulfide), tert-dodecanethiol-coated GNPs, 2-ethylhexanethiol-coated GNPs, decanethiol-coated GNPs and 3-ethoxythiophenol-coated GNPs; a composite of carbon black with poly(propylene-urethaneureaphenyl-disulfide), decanethiol-coated GNPs, and 4-chlorobenzenemethanethiol-based GNPs; HBC—C12, decanethiol-coated GNPs, 2-naphthalenethiol-coated GNPs, decanethiol-coated GNPs, 3-ethoxythiophenol-coated GNPs, and HBC—C12; decanethiol-coated GNPs, HBC—C12, 3-ethoxythiophenol-coated GNPs, and hexanethiol-coated GNPs; HBC—C12, and decanethiol-coated GNPs; a composite of carbon black with poly(propylene-urethaneureaphenyl-disulfide), 2-naphthalenethiol-coated GNPs, and decanethiol-coated GNPs; a composite of carbon black with poly(propylene-urethaneureaphenyl-disulfide), 2-naphthalenethiol-coated GNPs, and decanethiol-coated GNPs; 2-naphthalenethiol-coated GNPs, decanethiol-coated GNPs, and benzyl mercaptan-coated GNPs; decanethiol-coated GNPs and 2-nitro-4-(trifluoromethyl)benzenethiol-coated GNPs; hexanethiol-coated GNPs; hexanethiol-coated GNPs, and 3-ethoxythiophenol-coated GNPs; a composite of carbon black with poly(propylene-urethaneureaphenyl-disulfide), 2-naphthalenethiol-coated GNPs and decanethiol-coated GNPs; a composite of carbon black with poly(propylene-urethaneureaphenyl-disulfide), 2-naphthalenethiol-coated GNPs, and decanethiol-coated GNPs; 2-naphthalenethiol-coated GNPs, decanethiol-coated GNPs, and benzyl mercaptan-coated GNPs; decanethiol-coated GNPs, 3-ethoxythiophenol-coated GNPs and PDPP-TNT; PDPP-TNT, 3-ethoxythiophenol-coated GNPs, and decanethiol-coated GNPs; decanethiol-coated GNPs, 3-ethoxythiophenol-coated GNPs and PDPP-TNT; PDPP-TNT, decanethiol-coated GNPs, and hexanethiol-coated GNPs; PDPP-TNT, 3-ethoxythiophenol-coated GNPs, and hexanethiol-coated GNPs; PDPP-TNT, and a composite of carbon black with poly(propylene-urethaneureaphenyl-disulfide); PDPP-TNT, dodecanethiol-coated GNPs, and a composite of carbon black with poly(propylene-urethaneureaphenyl-disulfide); PDPP-TNT, and decanethiol-coated GNPs; 3-ethoxythiophenol-coated GNPs, and PDPP-TNT; decanethiol-coated GNPs, octadecanethiol-coated GNPs, and 3-ethoxythiophenol-coated GNPs; PDPP-TNT, 3-ethoxythiophenol-coated GNPs, and 2-naphthalenethiol-coated GNPs; PDPP-TNT; PDPP-TNT, and HBC—C12; PDPP-TNT, octadecanethiol-coated GNPs, 3-ethoxythiophenol-coated GNPs, and dibutyl disulfide-coated GNPs; decanethiol-coated GNPs, dodecanethiol-coated GNPs, and 3-ethoxythiophenol-coated GNPs; PDPP-TNT, octadecanethiol-coated GNPs, 3-ethoxythiophenol-coated GNPs, and dibutyl disulfide-coated GNPs; decanethiol-coated GNPs, dodecanethiol-coated GNPs, PDPP-TNT, and 3-ethoxythiophenol-coated GNPs; decanethiol-coated GNPs, and tert-dodecanethiol-coated GNPs; PDPP-TNT, decanethiol-coated GNPs, hexanethiol-coated GNPs, and octadecanethiol-coated GNPs; PDPP-TNT, decanethiol-coated GNPs, HBC—C12, and a composite of carbon black with poly(propylene-urethaneureaphenyl-disulfide); PDPP-TNT, HBC—C12, and octadecanethiol-coated GNPs; PDPP-TNT, a composite of black carbon with poly(propylene-urethaneureaphenyl-disulfide) mixed with poly(urethane-carboxyphenyl-disulfide), 2-ethylhexanethiol-coated GNPs, and decanethiol-coated GNPs; PDPP-TNT, a composite of black carbon with poly(propylene-urethaneureaphenyl-disulfide) mixed with poly(urethane-carboxyphenyl-disulfide), 2-ethylhexanethiol-coated GNPs, HBC—C12, and hexanethiol-coated GNPs; PDPP-TNT, octadecanethiol-coated GNPs, hexanethiol-coated GNPs, and dibutyl disulfide-coated GNPs; PDPP-TNT, decanethiol-coated GNPs, tert-dodecanethiol-coated GNPs and a composite of black carbon with poly(propylene-urethaneureaphenyl-disulfide) mixed with poly(urethane-carboxyphenyl-disulfide), 2-ethylhexanethiol-coated GNPs; PDPP-TNT, decanethiol-coated GNPs, and 2-naphthalenethiol-coated GNPs; PDPP-TNT, hexanethiol-coated GNPs, decanethiol-coated GNPs, and dibutyl disulfide-coated GNPs; PDPP-TNT, hexanethiol-coated GNPs, 2-ethylhexanethiol-coated GNPs, and dodecanethiol-coated GNPs; PDPP-TNT, dodecanethiol-coated GNPs, octadecanethiol-coated GNPs, and hexanethiol-coated GNPs; PDPP-TNT, octadecanethiol-coated GNPs, and hexanethiol-coated GNPs; PDPP-TNT, octadecanethiol-coated GNPs, 2-ethylhexanethiol-coated GNPs, and hexanethiol-coated GNPs; PDPP-TNT, decanethiol-coated GNPs, dodecanethiol-coated GNPs, and hexanethiol-coated GNPs; PDPP-TNT, octadecanethiol-coated GNPs, hexanethiol-coated GNPs, dibutyl disulfide-coated GNPs; PDPP-TNT, decanethiol-coated GNPs, dodecanethiol-coated GNPs, and hexanethiol-coated GNPs; hexanethiol-coated GNPs, a composite of carbon black with poly(propylene-urethaneureaphenyl-disulfide), dibutyl disulfide-coated GNPs, and 3-ethoxythiophenol-coated GNPs; a composite of carbon black with poly(propylene-urethaneureaphenyl-disulfide), tert-dodecanethiol-coated GNPs, 3-ethoxythiophenol-coated GNPs, and 2-nitro-4-(trifluoromethyl)benzenethiol-coated GNPs; 2-nitro-4-(trifluoromethyl)benzenethiol-coated GNPs, 2-ethylhexanethiol-coated GNPs, and HBC—C12; and 2-nitro-4-(trifluoromethyl)benzenethiol-coated GNPs, HBC—C12, 3-ethoxythiophenol-coated GNPs, and decanethiol-coated GNPs. Each possibility represents a separate embodiment of the invention.

In some embodiments, the at least one sensor is configured to detect at least one VOC or SVOC selected from the group consisting of 2-methylbutane, 2,2,4,6,6-pentamethylheptane, cyclopentane, isopropyl alcohol, 2,3-dimethyl-2,3-butanediol, diisobutyl phthalate, squalene, xylene and combinations thereof. Each possibility represents a separate embodiment of the invention.

In some embodiments, the absorbent material is selected from the group consisting of polydimethylsiloxane (PDMS), poly(2,6-diphenylphenylene oxide), polyacrylate, PDMS-divinylbenzene (PDMS-DVB), activated carbon-PDMS; polyethylene glycol-divinylbenzene, polyethylene glycol-template resin; divinylbenzene-activated carbon-PDMS; graphitized carbon black, styrene-divinylbenzene and combinations thereof. In some embodiments, the absorbent material comprises polydimethylsiloxane (PDMS) and/or poly(2,6-diphenylphenylene oxide). Each possibility represents a separate embodiment of the invention.

In some embodiments, the absorbent material is covered on its external side with a cover selected from aluminum foil and adhesive tape. In some embodiments, placing the absorbent material on the skin of the subject comprises placing the absorbent material on at least one of the chest, mastoid part of the temporal bone and inner arm skin of the subject.

In some embodiments, the predetermined period of time ranges from about 5 to about 240 minutes.

In some embodiments, the step of retrieving the at least one VOC or SVOC from the absorbent material comprises heating the absorbing material to at least about 150° C.

In some embodiments, the reference value is determined from a database of responses of the at least one sensor to skin-emitted or skin excreted VOCs or SVOCs of subjects afflicted with pulmonary tuberculosis and subjects known to be TB negative.

In some embodiments, the output signal measured upon exposure of the at least one sensor to the test sample is an electrical signal selected from the group consisting of resistance, conductance, alternating current (AC), capacitance, impedance, inductance, electrical potential, and voltage threshold. Each possibility represents a separate embodiment of the invention.

In another aspect, there is provided a skin-mountable medical device for diagnosing and/or monitoring pulmonary tuberculosis in a subject, said device comprising: a flexible fixing unit; and a sensing unit comprising at least one sensor comprising a material selected from the group consisting of conductive nanostructures coated with an organic coating, a conducting polymer and a conductive polymer composite.

In some embodiments, the skin-mountable medical device further comprises at least one of (a) a processing unit, which receives an output signal from the at least one sensor and compares said signal to a reference value and (b) a transmitter, which receives an output signal of the at least one sensor and transmits said signal to a remote server and/or to a portable electronic device.

In some embodiments, the fixing unit has two opposing surfaces forming a structure comprising an internal face and an external face, wherein the sensing unit is disposed on said internal face and said internal face faces the skin during use. In some embodiments, the internal face comprises an adhesive and contacts the skin during use. In some embodiments, the internal face substantially isolates a skin area from the environment, when mounted on said skin area.

In some embodiments, the conductive nanostructures coated with an organic coating are selected from gold nanoparticles (GNPs) coated with a thiol or a disulfide and single walled carbon nanotubes (SWCNTs) coated with polycyclic aromatic hydrocarbon (PAH).

In some embodiments, the thiol is selected from the group consisting of 3-ethoxythiophenol, 2-ethoxythiophenol, decanethiol, 2-nitro-4-(trifluoromethyl)benzenethiol, butanethiol, benzyl mercaptan, octadecanethiol, 2-naphthalenethiol, 4-chlorobenzenemethanethiol, dodecanethiol, tert-dodecanethiol, 2-ethylhexanethiol, hexanethiol, octadecanethiol, 1-methyl-2-imidazolethiol, and combinations thereof. Each possibility represents a separate embodiment of the invention. In some embodiments, the disulfide comprises dibutyl disulfide. Each possibility represents a separate embodiment of the invention.

In some embodiments, the polycyclic aromatic hydrocarbon comprises hexa-perihexabenzocoronene. In certain embodiments, the polycyclic aromatic hydrocarbon comprises HBC—C12.

In some embodiments, the conducting polymer is selected from the group consisting of diketopyrrolopyrrole-naphthalene copolymer (PDPP-TNT), polydiketopyrrolopyrrole, polyaniline (PANT), polythiophene, poly(3,4-ethylenedioxythiophene)-poly(styrene-sulfonate) (PEDOT:PSS), polypyrrole, and derivatives and combinations thereof. Each possibility represents a separate embodiment of the invention.

In some embodiments, the conductive polymer composite comprises a disulfide polymer mixed with carbon black. In some embodiments, the disulfide polymer is selected from poly(propylene-urethaneureaphenyl-disulfide), poly(urethane-carboxyphenyl-disulfide) and combinations thereof. Each possibility represents a separate embodiment of the invention.

In some embodiments, the at least one sensor comprises HBC—C12 or decanethiol-coated GNPs.

In some embodiments, the sensing unit comprises a sensor array. In further embodiments, the sensor array comprises a combination of sensors selected from the list presented hereinabove in connection with the diagnosing method embodiments.

In some embodiments, the at least one sensor is configured in a form selected from the group consisting of a capacitive sensor, a resistive sensor, a chemiresistive sensor, an impedance sensor, and a field effect transistor sensor. Each possibility represents a separate embodiment of the invention.

In some embodiments, the sensing unit further comprises at least two electrodes being in electrical contact with the at least one sensor. In some embodiments, the sensing unit further comprises a measuring device configured to measure the electrical signal of the at least one sensor. In some embodiments, the sensing unit further comprises a rigid or a flexible substrate, on which the at least one sensor is disposed. The substrate can be made of a material selected from the group consisting of paper, polymer, silicon dioxide, silicon rubber, ceramic material, metal, insulator, semiconductor, semimetal and combinations thereof. In some embodiments, the polymer is selected from the group consisting of polyamide, polyimide, polyester, polyimine, polyethylene, polyvinyl chloride, polydimethylsiloxane, polystyrene, and combinations thereof. Each possibility represents a separate embodiment of the invention.

In some embodiments, the device further comprises at least one hydrophobic and/or oleophobic membrane disposed on the internal face of the fixing unit, which substantially separates the at least one sensor from the skin, when in use.

In some embodiments, at least one of the remote server and the portable electronic device comprises an algorithm, which compares the output signal of the at least one sensor to a reference. In some embodiments, the reference value is determined from a database of responses of the at least one sensor to skin-emitted or excreted VOCs or SVOCs of subjects afflicted with pulmonary tuberculosis and subjects known to be TB negative.

In some embodiments, the device comprises at least one indicator, wherein at least one of the processing unit and the transmitter is configured to transmit a positive indication signal or a negative indication signal to the at least one indicator, thereby displaying the diagnosis outcome.

In some embodiments, at least one of the processing unit, the remote server and the portable electronic device further comprises an algorithm configured to differentiate between the response of the at least one sensor to the skin-emitted or excreted VOCs or SVOCs and the response of said at least one sensor to a stimulus selected from the group consisting of temperature, humidity, lateral strain, and combinations thereof. Each possibility represents a separate embodiment of the invention.

In another aspect, there is provided a method for real-time diagnosing and/or monitoring pulmonary tuberculosis in a subject, the method comprising the steps of: providing the skin-mountable medical device disclosed herein; mounting the skin-mountable medical device on the skin of a subject, thus exposing the at least one sensor to at least one VOC or SVOC emitted or excreted from the skin; measuring an output signal of the at least one sensor upon exposure thereof to the at least one VOC or SVOC; analyzing the output signal by at least one of the processing unit, the remote server and the portable electronic device; and diagnosing tuberculosis if the output signal is greater than a reference.

In some embodiments, mounting the skin-mountable medical device on the skin of the subject comprises sticking the internal face of the flexible fixing unit to the skin of the subject. In further embodiments, mounting the skin-mountable medical device on the skin of the subject further comprises substantially isolating the skin of the subject, which is in contact with the flexible fixing unit from the environment. In some embodiments, the skin-mountable medical device is mounted on at least one of chest area skin, mastoid skin and brachium skin of the subject. Each possibility represents a separate embodiment of the invention.

In some embodiments, the measuring step is performed after about 5 minutes to about 240 minutes following the mounting step.

In some embodiments, analyzing the output signal of the at least one sensor comprises extracting a plurality of response-induced parameters from said signal, the response-induced parameters being selected from the group consisting of full non-steady state response at the beginning of the signal, full non-steady state response at the beginning of the signal normalized to baseline, full non-steady state response at the middle of the signal, full non-steady state response at the middle of the signal normalized to baseline, full steady state response, full steady state response normalized to baseline, area under non-steady state response, area under steady state response, the gradient of the response upon exposure of the at least one sensor, and the time required to reach 10%, 20%, 30%, 40%, 50%, 60%, 70%, 80%, 90% or 100% of the response upon exposure of the at least one sensor. Each possibility represents a separate embodiment of the invention.

In some embodiments, diagnosing tuberculosis comprises transmitting the positive indication signal or a negative indication signal from any one of the processing unit, the remote server and the portable electronic device to the indicator, thereby displaying the diagnosis outcome. In some embodiments, diagnosing tuberculosis further comprises transmitting the positive indication signal or a negative indication signal from the processing unit to the remote server and/or a portable electronic device.

In another aspect, there is provided a method of diagnosing and/or monitoring pulmonary tuberculosis (TB) in a subject, the method comprising the steps of: placing an absorbent material on the skin of the subject for a predetermined period of time, thereby obtaining a test sample; retrieving the test sample from the absorbent material; determining the level of at least one skin-emitted or excreted VOC or SVOC indicative of pulmonary tuberculosis in the test sample, said VOC or SVOC being selected from the group consisting of 2-methylbutane, 2,2,4,6,6-pentamethylheptane, cyclopentane, isopropyl alcohol, 2,3-dimethyl-2,3-butanediol diisobutyl phthalate, squalene, xylene and combinations thereof; and comparing the level of the at least one skin-emitted or excreted VOC or SVOC indicative of pulmonary tuberculosis from the test sample with the level of said at least one VOC or SVOC in a negative control sample, whereby a significantly different level of said at least one VOC or SVOC in the test sample as compared to the level of said compound in the negative control sample is indicative of pulmonary tuberculosis.

In some embodiments, the method comprises the step of determining the levels of at least three VOCs or SVOCs.

In some embodiments, the step of determining the level of the at least one skin-emitted or excreted VOC or SVOC indicative of tuberculosis comprises the use of at least one technique selected from the group consisting of Gas-Chromatography (GC), GC-lined Mass-Spectrometry (GC-MS), Proton Transfer Reaction Mass-Spectrometry (PTR-MS), Electronic nose device, and Quartz Crystal Microbalance (QCM). Each possibility represents a separate embodiment of the invention.

In some embodiments, placing the absorbent material on the skin of the subject comprises placing the absorbent material on the chest, mastoid part of the temporal bone and/or inner arm skin of the subject. Each possibility represents a separate embodiment of the invention.

In some embodiments, the predetermined period of time ranges from about 5 to about 240 minutes.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIG. 10A shows the side view of the sensing unit and FIG. 10B shows the face of the sensing unit including the exposed GNPs-based sensors.

DETAILED DESCRIPTION OF THE INVENTION

Figure 1:
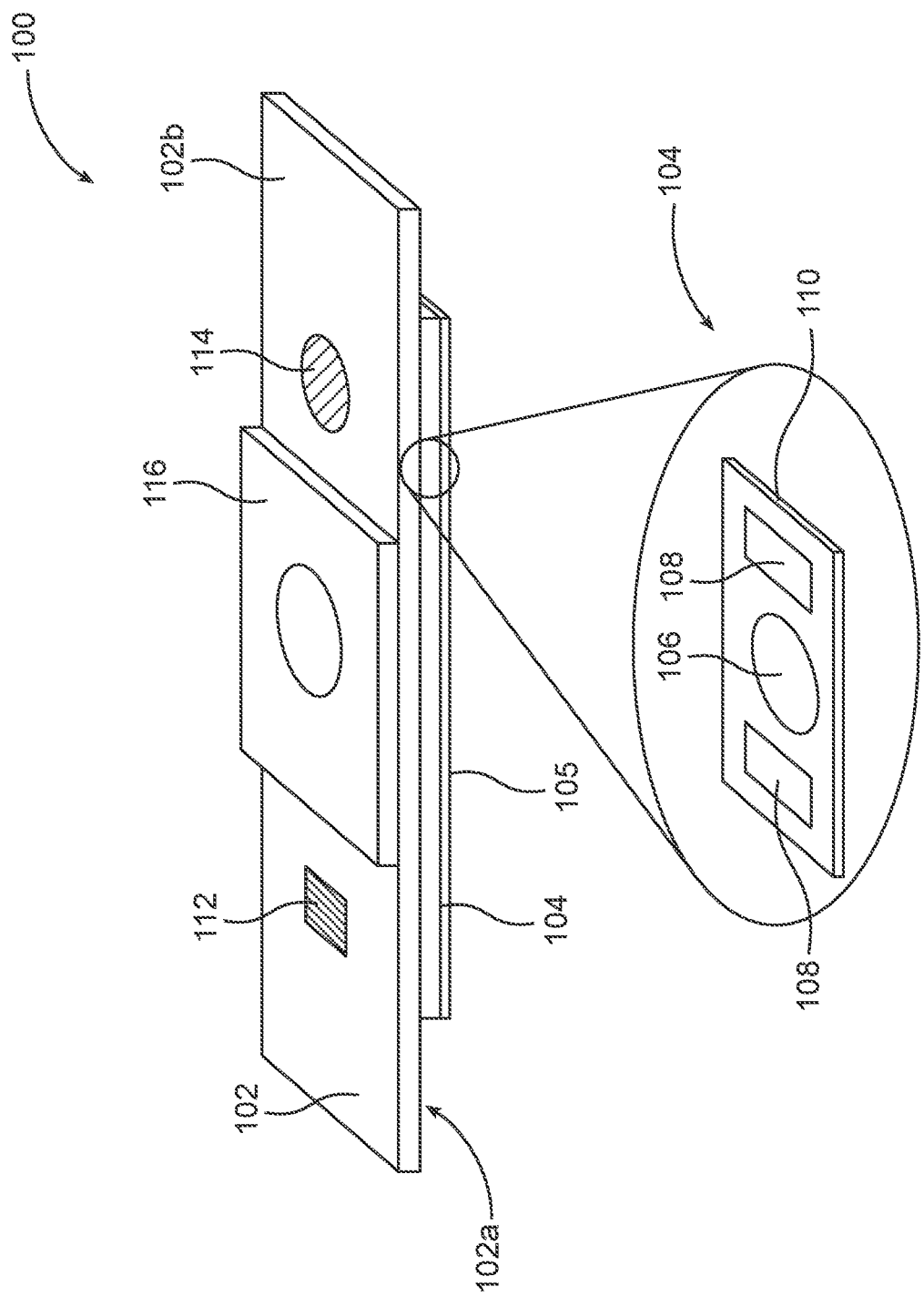
FIG. 1: Schematic representation of the skin-mountable medical device according to some embodiments of the invention.

The present invention is directed to methods and medical devices for diagnosis and/or monitoring of tuberculosis. The diagnosis is based on the detection of volatile and semi-volatile organic compounds, which were found to be excreted through the skin of subjects suffering from active tuberculosis. It was surprisingly found that although pulmonary tuberculosis affects the lungs and the respiratory system, VOCs and SVOCs indicative of pulmonary tuberculosis, which are emitted from the skin, provide reliable indication and diagnosis of pulmonary tuberculosis.

In some aspects and embodiments of the invention the diagnosis of tuberculosis is achieved by placing an absorbent material on the skin of the subject in order to absorb the VOCs and/or SVOCs, which are indicative of tuberculosis, from the skin of the subject. It was surprisingly found that such derivation of TB-indicative compounds from the skin still provides reliable results after retrieving the VOCs and/or SVOCs from the absorbent material through desorption of the compounds and the analysis and/or detection thereof using GC-MS and/or tailored nanosensors.

Thus, according to a first aspect, there is provided a method of diagnosing and/or monitoring tuberculosis (TB) in a subject, the method comprising the steps of: obtaining a test sample comprising at least one volatile organic compound (VOC) or semi-volatile organic compound (SVOC) excreted or emitted from the skin of the subject; providing a sensing unit comprising at least one sensor comprising a material selected from the group consisting of conductive nanostructures coated with an organic coating, a conducting polymer and a conductive polymer composite; exposing the at least one sensor to the test sample; measuring an output signal of the at least one sensor upon exposure thereof to the test sample; and diagnosing tuberculosis if the signal is greater than a reference.

Said method can be considered a non-real time method. The term "non-real time", as used herein, refers in some embodiments, to a diagnosing process, which is performed by at least two unconnected or uncoupled devices or units. The non-real time diagnosing process can include a step of obtaining the test sample, which is performed by a first device and a step of analyzing the test sample, which is performed by a second device. In other embodiments, the non-real time diagnosing process includes a step of obtaining the test sample, which is performed by the first device and a step of providing the results of the analysis of the test sample, which is performed by the second device.

In some aspects and embodiments of the invention, real-time diagnosing and/or monitoring of tuberculosis is achieved by mounting a portable medical device on the skin of a subject, where the device can be used, inter alia, to continuously monitor the subject for the presence of tuberculosis. The device comprises a flexible fixing strap, which is preferably adhesive, such as a medical plaster, and a sensor comprising at least one of conductive nanostructures coated with an organic coating, a conducting polymer and a conductive polymer composite. When the device is placed or attached to the skin of the subject, the sensor is exposed to the skin-emitted or excreted VOCs and SVOCs, thereby allowing diagnosis of tuberculosis if tuberculosis biomarkers are present, based on the response of the sensor to the skin-emitted compounds, as compared to a reference. Said skin-mountable device has multiple advantages, such as low cost, easy handling and real-time diagnosing ability.

Thus, according to another aspect, there is provided a skin-mountable medical device for diagnosing and/or monitoring tuberculosis in a subject, said device comprising: a flexible fixing unit; and a sensing unit comprising at least one sensor comprising a material selected from the group consisting of conductive nanostructures coated with an organic coating, a conducting polymer and a conductive polymer composite.

According to another aspect, there is provided a method for diagnosing and/or monitoring pulmonary tuberculosis in a subject, the method comprising the steps of: (a) providing a skin-mountable medical device comprising a flexible fixing unit; and a sensing unit comprising at least one sensor comprising a material selected from the group consisting of conductive nanostructures coated with an organic coating, a conducting polymer and a conductive polymer composite; (b) mounting the skin-mountable medical device on the skin of a subject, thus exposing the at least one sensor to at least one VOC or SVOC emitted or excreted from the skin; (c) measuring an output signal of the at least one sensor upon exposure thereof to the at least one VOC or SVOC; (d) analyzing the output signal; and (e) diagnosing tuberculosis if the output signal is greater than a reference.

Said method can be considered a real-time method. As used herein, the term "real-time" refers in some embodiments, to a diagnosing method, which allows analyzing the output signal of the at least one sensor as soon as the device is mounted on the skin of a subject. The term "real-time", as used herein, refers in further embodiments, to a diagnosing method, which is performed by a single device. The real-time diagnosing method can include obtaining the test sample and analyzing the same by a single device. In other embodiments, the real-time diagnosing method includes obtaining the test sample and providing the results of the analysis of the test sample by a single device.

The Absorbent Material

As indicated hereinabove, the non-real time TB diagnostic method according to the principles of the invention comprises a step of obtaining a test sample. In some embodiments, said step comprises placing an absorbent material on the skin of the subject for a predetermined period of time. In further embodiments, said step comprises retrieving the at least one VOC or SVOC from the absorbent material.

In some embodiments the absorbent material is selected from the group consisting of polydimethylsiloxane (PDMS), poly(2,6-diphenylphenylene oxide), polyacrylate, PDMS-divinylbenzene (PDMS-DVB), activated carbon-PDMS; polyethylene glycol-divinylbenzene, polyethylene glycol-template resin; divinylbenzene-activated carbon-PDMS; graphitized carbon black, styrene-divinylbenzene and combinations thereof. Each possibility is a separate embodiment of the invention.

In some embodiments the absorbent material comprises polydimethylsiloxane (PDMS). In some embodiments the absorbent material comprises poly(2,6-diphenylphenylene oxide). In some embodiments the absorbent material comprises polyacrylate. In some embodiments the absorbent material comprises PDMS-divinylbenzene (PDMS-DVB). In some embodiments the absorbent material comprises activated carbon-PDMS. In some embodiments the absorbent material comprises polyethylene glycol-divinylbenzene. In some embodiments the absorbent material comprises polyethylene glycol-template resin. In some embodiments the absorbent material comprises divinylbenzene-activated carbon-PDMS. In some embodiments the absorbent material comprises graphitized carbon black, styrene-divinylbenzene. In some embodiments the absorbent material comprises polydimethylsiloxane (PDMS) and/or poly(2,6-diphenylphenylene oxide). In some embodiments, the absorbent material comprises calcium sulfate ($CaSO_4$).

Specific absorbents, including polydimethylsiloxane (PDMS) and poly(2,6-diphenylphenylene oxide) (Tenax) were found optimal in terms of both quick and thorough absorption of volatile organic compounds and semi-volatile organic compounds and easy thermal desorption of the VOCs and SVOCs therefrom, with minor effect on the detection of VOCs and SVOC.

In some embodiments, the non-real time diagnostic method further comprises cleaning the absorbent material prior to placing thereof on the skin of the subject. The absorbing material can be cleaned, for example, by a solution comprising at least one component selected from anionic surface active agents, non-ionic surface active agents, stabilizing agents, alkalis, non-phosphate detergent builders, and sequestering agents. One non-limiting example of a commercially-available solution suitable for cleaning the absorbing material is Decon 90. In further embodiments, the absorbent material cleaning step comprises storing the absorbent material in vacuum oven at a temperature of at least about 150° C. In further embodiments, the absorbent material is stored at a temperature of at least about 175° C., at least about 200° C., or at least about 210° C. In some embodiments, the absorbent material is stored for at least about 5 hours. In still further embodiments, the absorbent material is stored for at least about 10 hours or for at least about 15 hours. In yet further embodiments, the absorbent material cleaning step comprises thermal conditioning at the temperature of at least about 200° C. under a constant gas flow. In still further embodiments, the thermal conditioning is performed at the temperature of at least about 250° C. or 270° C. The gas can be selected from nitrogen and helium. In further embodiments, the thermal conditioning is performed for at least about 30 minutes. In still further embodiments, the thermal conditioning is performed for at least about 60 minutes. In certain embodiments, the absorbing material comprises PDMS. Each possibility represents a separate embodiment of the invention.

In some embodiments the step of retrieving the at least one VOC or SVOC from the absorbent material comprises retrieving at least 50% of the total amount of the at least one VOC or SVOC from the absorbent material. In some embodiments the step of retrieving the at least one VOC or SVOC from the absorbent material comprises retrieving at least 75% of the total amount of the at least one VOC or SVOC from the absorbent material. In some embodiments the step of retrieving the at least one VOC or SVOC from the absorbent material comprises desorbing the at least one VOC or SVOC from the absorbent material prior to exposing the at least one sensor to the test sample. In some embodiments desorbing comprises heating the absorbing material to at least about 100° C. In some embodiments desorbing comprises heating the absorbing material to at least about 150° C. In some embodiments desorbing comprises heating the absorbing material to at least about 200° C. In some embodiments desorbing comprises heating the absorbing material to at least about 250° C. In some embodiments desorbing comprises heating the absorbing material to about 270° C.

As used herein, the term "about" refers to a range of values ±20%, or ±10% of a specified value. For example, the phrase "heating the absorbing material to at least about 200° C." includes ±20% of 200° C., and includes heating over 160° C.

In some embodiment the method further comprises the step of covering the absorbent material with a cover. In further embodiments, the absorbent material is covered on its external side. In some embodiments the absorbent material is covered with a cover. In some embodiments the cover is selected from a metallic foil, a paper tape or a tape made of a polymer. In some embodiments the cover is selected from aluminum foil and adhesive tape. Each possibility represents a separate embodiment of the invention.

According to some embodiments, the absorbent material is placed on the skin of the subject for a predetermined period of time. In some embodiments the predetermined period of time is in the range of about 5 minutes to about 12 hours. In further embodiments, the predetermined period of time is in the range of about 20 minutes to about 10 hours, of about 1 hour to about 8 hours, or from about 2 hours to about 6 hours. In certain embodiments, the predetermined time is about 4 hours. In some embodiments the predetermined period of time is in the range of about 10 to 120 minutes, or from about 30 to 90 minutes. Each possibility represents a separate embodiment of the invention.

In some embodiments placing the absorbent material on the skin of the subject comprises placing the absorbent material on the chest of the subject. In some embodiments placing the absorbent material on the skin of the subject comprises placing the absorbent material on the mastoid part of the temporal bone of the subject. In some embodiments placing the absorbent material on the skin of the subject comprises placing the absorbent material on the inner arm skin of the subject.

The Sensor

As mentioned hereinabove, the sensing unit according to the principles of the invention comprises at least one sensor comprising a material selected from the group consisting of conductive nanostructures coated with an organic coating, a conducting polymer and a conductive polymer composite In some embodiments, the at least one sensor comprises conductive nanostructures coated with an organic coating. In some embodiments, the conductive nanostructures comprise conductive nanoparticles. In further embodiments, said conductive nanoparticles are selected from metal and metal alloy nanoparticles. According to certain embodiments, the conductive nanoparticles comprise metals and metal alloys selected from the group consisting of Au, Ag, Ni, Co, Pt, Pd, Cu, Al, Au/Ag, Au/Cu, Au/Ag/Cu, Au/Pt, Au/Pd, Au/Ag/Cu/Pd, Pt/Rh, Ni/Co, and Pt/Ni/Fe. Each possibility represents a separate embodiment of the invention. In some embodiments, the conductive nanoparticles comprise platinum nanoparticles and/or gold nanoparticles (GNPs). In some particular embodiments, the conductive nanoparticles comprise gold nanoparticles (GNPs).

In various embodiments, the coating of the conductive nanoparticles comprises a monolayer or multilayers of organic compounds, wherein the organic compounds can be small molecules, monomers, oligomers or polymers, preferably short polymeric chains. In particular embodiments, the organic compounds are selected from the group consisting of alkylthiols, arylthiols, alkylarylthiols, alkylthiolates, ω-functionalized alkylthiolates, arenethiolates, (γ-mercaptopropyl)tri-methyloxysilane, dialkyl sulfides, diaryl sulfides, alkylaryl sulfides, dialkyl disulfides, diaryl disulfides, alkylaryl disulfides, alkyl sulfites, aryl sulfites, alkylaryl sulfites, alkyl sulfates, aryl sulfates, alkylaryl sulfates, xanthates, oligonucleotides, polynucleotides, dithiocarbamate, alkyl amines, aryl amines, diaryl amines, dialkyl amines, alkylaryl amines, arene amines, alkyl phosphines, aryl phosphines, dialkyl phosphines, diaryl phosphines, alkylaryl phosphines, phosphine oxides, alkyl carboxylates, aryl carboxylates, dialkyl carboxylates, diaryl carboxylates, alkylaryl carboxylates, cyanates, isocyanates, peptides, proteins, enzymes, polysaccharides, phospholipids, and combinations and derivatives thereof. Each possibility represents a separate embodiment of the invention.

In some embodiments the conductive nanostructures coated with an organic coating are selected from gold nanoparticles coated with a thiol or a disulfide. In a particular embodiment, the organic coating comprises alkylthiols with $C_3$-$C_{24}$ chains.

In some embodiments the thiol is selected from the group consisting of 3-ethoxythiophenol, 2-ethoxythiophenol, decanethiol, 2-nitro-4-(trifluoromethyl)benzenethiol, butanethiol, benzyl mercaptan, octadecanethiol, 2-naphthalenethiol, 4-chlorobenzenemethanethiol, dodecanethiol, tert-dodecanethiol, 2-ethylhexanethiol, hexanethiol, octadecanethiol, 1-methyl-2-imidazolethiol, and combinations and derivatives thereof. Each possibility is a separate embodiment of the invention.

In some embodiments the thiol is selected from the group consisting of 3-ethoxythiophenol, 2-ethoxythiophenol, decanethiol, 2-nitro-4-(trifluoromethyl)benzenethiol, butanethiol, benzyl mercaptan, octadecanethiol, 2-naphthalenethiol, 4-chlorobenzenemethanethiol and combinations and derivatives thereof.

In some embodiments the thiol comprises 3-ethoxythiophenol. In some embodiments the thiol comprises 2-ethoxythiophenol. In some embodiments the thiol comprises decanethiol. In some embodiments the thiol comprises 2-nitro-4-(trifluoromethyl)benzenethiol. In some embodiments the thiol comprises butanethiol. In some embodiments the thiol comprises benzyl mercaptan. In some embodiments the thiol comprises octadecanethiol. In some embodiments the thiol comprises 2-naphthalenethiol. In some embodiments the thiol comprises 4-chlorobenzenemethanethiol. In some embodiments the thiol comprises tert-dodecanethiol. In some embodiments the thiol comprises 2-ethylhexanethiol.

In certain embodiments, the at least one sensor does not include gold nanoparticles coated with dodecanethiol. In certain embodiments, the sensing unit is devoid of gold nanoparticles coated with dodecanethiol.

In some embodiments, the disulfide comprises dibutyl disulfide.

In some embodiments, the organic coating comprises a monolayer of organic compounds. In further embodiments, the organic coating comprises two, three, four, five, six, seven, eight, nine, ten or more layers of organic compounds. Each possibility represents a separate embodiment of the invention.

Sensors comprising metal nanoparticles capped with various organic coatings can be synthesized as is known in the art, for example using the two-phase method (Brust et al., J. Chem. Soc. Chem. Commun., 1994, 801, 2) with some modifications (Hostetler et al., Langmuir, 1998, 14, 24). Capped gold nanoparticles can be synthesized by transferring $AuCl_4^-$ from aqueous $HAuCl_4 \cdot xH_2O$ solution to a toluene solution by the phase-transfer reagent TOAB. After isolating the organic phase, excess thiols are added to the solution. The mole ratio of thiol:$HAuCl_4 \cdot xH_2O$ can vary between 1:1 and 10:1, depending on the thiol used. This is performed in order to prepare mono-disperse solution of gold nanoparticles in average size of about 2-5 nm. After vigorous stirring of the solution, aqueous solution of reducing agent $NaBH_4$ in large excess is added. The reaction is constantly stirred at room temperature for at least 3 hours to produce a dark brown solution of the thiol-capped Au nanoparticles. The resulting solution is further subjected to solvent removal in a rotary evaporator followed by multiple washings using ethanol and toluene. Gold nanoparticles capped with particular thiols, can be synthesized by ligand—exchange method from pre-prepared hexanethiol-capped gold nanoparticles. In a typical reaction, excess of thiol is added to a solution of hexanethiol-capped gold nanoparticles in toluene. The solution is kept under constant stirring for few days in order to allow as much ligand conversion as possible. The nanoparticles are purified from free thiol ligands by repeated extractions.

In some embodiments, the organic coating comprises an amine. One non-limiting example of a suitable amine is oleylamine.

The metal nanoparticles may have any desirable morphology including, but not limited to, a cubic, a spherical, and a spheroidal morphology. Each possibility represents a separate embodiment of the invention. In some embodiments, the metal nanoparticles have a spherical morphology. In some embodiments, the metal nanoparticles have a cubic morphology.

According to some embodiments, the mean particle size of the metal nanoparticles is in the range of about 1 to about 10 nm, such as, for example, about 2 to about 5 nm or about 3 to about 4 nm. Each possibility represents a separate embodiment of the invention. According to further embodiments, the metal nanoparticles are characterized by a narrow particle size distribution.

The synthesized nanoparticles can then be assembled (e.g. by a self-assembly process) to produce 1D wires or a film of capped nanoparticles. The term "film", as used herein, corresponds to a configuration of well-arranged assembly of capped nanoparticles. 2D or 3D films of coated nanoparticles may also be used. Exemplary methods for obtaining well-ordered two or three dimensional assemblies of coated nanoparticles include, but are not limited to, i. Random deposition from solution of capped nanoparticles on solid surfaces. The deposition is performed by drop casting, spin coating, spray coating and other similar techniques.

ii. Field-enhanced or molecular-interaction-induced deposition from solution of capped nanoparticles on solid surfaces.

iii. Langmuir-Blodgett or Langmuir-Schaefer techniques. The substrate is vertically plunged through self-organized/well-ordered 2D monolayer of capped nanoparticles at the air-subphase interface, wherein the latter is being subsequently transferred onto it. Multiple plunging of the substrate through the 2D monolayer of capped nanoparticles at the air-subphase interface results in the fabrication of the 3D-ordered multilayers of capped nanoparticles.

iv. Soft lithographic techniques, such as micro-contact printing (mCP), replica molding, micro-molding in capillaries (MIMIC), and micro-transfer molding (mTM). These methods are based on variations of self-assembly and replica molding of organic molecules and polymeric materials, for fabricating capped nanoparticles from nanometer-scale to a mesoscopic scale (Zhao et al., J. Mater. Chem., 1997, 7(7), 1069).

v. Various combinations of Langmuir-Blodgett or Langmuir-Schaefer methods with soft lithographic techniques can be used to produce patterned Langmuir-Blodgett films of molecularly modified capped nanoparticles which are transferred onto solid substrates.

vi. Printing on solid-state or flexible substrates using an inject printer designated for printed electronics. A solution containing the capped nanoparticles is used as a filling material (or "ink") of the printing head according to procedures well known in the art.

According to various embodiments of the invention, the conductive nanostructures comprise single-walled carbon nanotubes (SWCNTs). The nanotubes can be arranged in a random network configuration. In some embodiments, the network of SWCNTs can be fabricated by a physical manipulation or in a self-assembly process. The term "self-assembly" as used herein refers to a process of the organization of molecules without intervening from an outside source. The self-assembly process occurs in a solution/solvent or directly on a solid-state substrate.

Main approaches for the synthesis of carbon nanotubes in accordance with the present invention include, but are not limited to, laser ablation of carbon, electric arc discharge of graphite rod, and chemical vapor deposition (CVD) of hydrocarbons. Among these approaches, CVD coupled with photolithography has been found to be the most versatile in the preparation of various carbon nanotube devices. In a CVD method, a transition metal catalyst is deposited on a substrate (e.g. silicon wafer) in the desired pattern, which may be fashioned using photolithography followed by etching. The silicon wafer having the catalyst deposits is then placed in a furnace in the presence of a vapor-phase mixture of, for example, xylene and ferrocene. Carbon nanotubes typically grow on the catalyst deposits in a direction normal to the substrate surface. Various carbon nanotube materials and devices are currently available from commercial sources.

Other CVD methods include the preparation of carbon nanotubes on silica ($SiO_2$) and silicon surfaces without using a transition metal catalyst. Accordingly, areas of silica are patterned on a silicon wafer, by photolithography and etching. Carbon nanotubes are then grown on the silica surfaces in a CVD or a plasma-enhanced CVD (PECVD) process. These methods provide the production of carbon nanotube bundles in various shapes.

The term "single walled carbon nanotube" as used herein refers to a cylindrically shaped thin sheet of carbon atoms having a wall which is essentially composed of a single layer of carbon atoms which are organized in a hexagonal crystalline structure with a graphitic type of bonding. A nanotube is characterized by the length-to-diameter ratio. It is to be understood that the term "nanotubes" as used herein refers to structures in the nanometer as well as micrometer range.

According to various embodiments, the single-walled carbon nanotubes of the present invention have diameters ranging from about 0.6 nanometers (nm) to about 100 nm and lengths ranging from about 50 nm to about 10 millimeters (mm). More preferably, the single-walled carbon nanotubes have diameters ranging from about 0.7 nm to about 50 nm and lengths ranging from about 250 nm to about 1 mm. Even more preferably, the single-walled carbon nanotubes have diameters ranging from about 0.8 nm to about 10 nm and lengths ranging from about 0.5 micrometer (μm) to about 100 Most preferably, the single-walled carbon nanotubes of the present invention have diameters ranging from about 0.9 nm to about 5 nm and lengths ranging from about 1 μm to about 50 μm.

In some embodiments, the SWCNTs are coated with polycyclic aromatic hydrocarbons (PAH) or derivatives thereof, such as hexa-peri-hexabenzocoronene (HBC) molecules. HBC molecules can be unsubstituted or substituted by any one of methyl ether (HBC—$OC_1$), 2-ethyl-hexyl (HBC—$C_{6,2}$), 2-hexyldecyl (HBC—$C_{10,6}$), 2-decyltetradecyl (HBC—$C_{14,10}$), and dodecyl (HBC—$C_{12}$). Each possibility represents a separate embodiment of the invention. In particular embodiments, the organic coating comprises crystal hexakis(n-dodecyl)-peri-hexabenzocoronene (HBC—$C_{12}$).

In some embodiments, the at least one sensor comprises a conducting polymer. The term "conducting polymer", as used in some embodiments, refers to a polymer which is intrinsically electrically-conductive, and which does not require incorporation of electrically-conductive additives (e.g., carbon black, carbon nanotubes, metal flake, etc.) to support substantial conductivity of electronic charge carrier.

In further embodiments, the term "conducting polymer" refers to a polymer which becomes electrically-conductive following doping with a dopant. In certain embodiments, said doping comprises protonation (also termed herein "protonic doping"). In still further embodiments, the term "conducting polymer" refers to a polymer which is electrically-conductive in the protonated state thereof, whether said protonation is either partial or full. Alternatively, conducting polymers can be doped via a redox reaction. In yet further embodiments, the term "conducting polymer" refers to a polymer which is electrically-conductive in the oxidized and/or reduced state thereof. The term "conducting polymer", as used herein, refers in some embodiments to a semiconducting polymer. The term "semiconducting polymer", as used in some embodiments, refers to a polymer which is intrinsically semi-conductive, and which does not require doping with charge transporting or withdrawing molecules or components to support substantial conductivity of electronic charge carrier. The conducting polymers suitable for use in the devices and methods of the present invention can have conductivity ranging from about 0.1 $S \cdot cm^{-1}$ to about 500 $S \cdot cm^{-1}$, from about 0.1 $S \cdot cm^{-1}$ to about 100 $S \cdot cm^{-1}$, or from about 0.1 $S \cdot cm^{-1}$ to about 10 $S \cdot cm^{-1}$.

In some embodiments the conducting polymer is selected from the group consisting of diketopyrrolopyrrole-naphthalene copolymer (PDPP-TNT), polydiketopyrrolopyrrole, polyaniline (PANI), polythiophene, poly(3,4-ethylenedioxythiophene)-poly(styrene-sulfonate) (PEDOT:PSS), polypyrrole, and derivatives and combinations thereof. In some embodiments, the polymer is PANI. In further embodiments, PANI is doped with a dopant. The dopant may be an acid, such that the doping would be a result of protonation. In some embodiments, the dopant is selected from the group consisting of hydrochloric acid, sodium bisulfate, salicylic acid, maleic acid, fumaric acid, benzoic acid, phosphoric acid and any combination thereof. Each possibility represents a separate embodiment of the invention.

In some embodiments, the conducting polymer is in a form of a conducting polymer film. Various techniques can be used to prepare conducting polymer films. The non-limiting examples include, spin-coating, dip-coating, electrochemical deposition, Langmuir-Blodgett technique, layer-by-layer (LBL) self-assembly technique, thermal evaporation, vapor deposition polymerization, drop-coating, electric field induced electrochemical polymerization, lift-off, float-on (LOFO), and inkjet-printing.

Spin-coating: Spin-coating is a simple method for preparing films from soluble conducting polymers. In this process, the conducting polymer solution is spread on a rotating substrate. After evaporation of solvent, a thin film is formed. Thickness of the film can be controlled, inter alia, by repeating the above process. Concentration of the solution and rotating rate of the substrate also play important roles in adjusting the thickness of the formed film. Said method can be used to prepare conducting polymer films on both conducting and insulating substrates.

Dip-coating: When dipping a substrate into a chemical polymerization solution, part of the polymer will be deposited onto its surface. This process occurs on different substrates, and the thickness of the film is usually controlled by dipping time. Another similar process involves alternatively immersing a substrate into the monomer and oxidant solutions. The adsorbed monomer is polymerized on the surface of substrate.

Electrochemical deposition: Electrochemical deposition can be used to conveniently deposit conducting polymer films. The thickness of the film can be controlled by the total charge passed through the electrochemical cell during film growing process. Moreover, the film can be deposited on patterned electrodes.

Layer-by-layer (LBL) self-assembly technique: By alternating immersion of the substrate into a polymeric anion solution and a polymeric cation solution, a composite film is formed, which consists of the two alternating ((layer by layer) polymers.

Thermal evaporation: Thermal evaporation technology can be realized by heating conducting polymer under vacuum, wherein the evaporated conducting polymer is deposited on the target substrate. The thickness of the film is determined by the evaporation duration.

Vapor deposition polymerization: Vapor deposition polymerization technology includes preparation of an oxidant film and placing the film in a monomer vapor ambiance. Monomers diffuse into the film and are polymerized thereon.

Drop-coating: A polymer solution is drop dried or drops of a monomer and oxidant solutions are dropped and reacted on a substrate.

Electric field induced electrochemical polymerization: Said method can be used to fabricate patterned conducting polymer films.

Inkjet-printing: Inkjet printing can be used for producing thin films from soluble conducting polymers.

LOFO: LOFO can be used for transferring the prepared polymer film to a desired substrate.

In some embodiments, the at least one sensor comprises a conductive polymer composite. The term "conductive polymer composite", as used in some embodiments, refers to a combination of a polymer which is not intrinsically conductive with electrically-conductive additives (e.g., carbon black, carbon nanotubes, metal flake, etc.).

In some embodiments the conductive polymer composite comprises a disulfide polymer mixed with a carbon powder. In certain embodiments, said carbon powder comprises carbon black.

Non-limiting examples of carbon black suitable for use in the conductive polymer composites include acetylene black, channel black, furnace black, lamp black and thermal black.

In some embodiments, carbon black is present in the conductive polymer composite in a weight percent ranging from about 1 to about 30 of the total weight of the composite. In further embodiments, carbon black is present in the conductive polymer composite in a weight percent ranging from about 3 to about 20, or from about 6 to about 10 of the total weight of the composite.

In some embodiments the conductive polymer composite comprises a disulfide polymer mixed with graphite According to some embodiments, the disulfide polymer is a self-healing polymer. The self-healing polymer can be a dynamically covalently crosslinked polymer, which crosslinking bridges comprise disulfide moieties. According to further embodiments, the self-healing polymer is cross-linked through aromatic disulfide moieties. In certain such embodiments, the dynamic crosslinking of the polymeric chains can proceed through the metathesis reaction of aromatic disulfides.

According to some embodiments, the polymeric chain comprises a polyurethane. The polyurethane can have a molecular weight in the range from about 250 to about 400 g/mole. The polymeric chain can further comprise an urea unit. Thus, in some embodiments, the polymeric chain comprises a poly(urea-urethane).

According to further embodiments, the polymeric chain comprises a polyether backbone segment. In certain embodiments, the poly(urea-urethane) comprises a polyether backbone segment. In further embodiments, the polyether backbone segment has an average molecular weight of at least about 2000 g/mole. In additional embodiments, the average molecular weight of the polyether backbone segment is in the range of about 2000 to 10,000 g/mole. In certain embodiments, the average molecular weight is from about 2000 to about 6000 g/mole. The polyether segment can be selected from polypropylene glycol or polyethylene glycol. Each possibility represents a separate embodiment of the invention.

According to some embodiments, the polymeric chain comprises an aromatic urethane unit. In certain embodiments, poly(urea-urethane) comprises an aromatic urethane unit. In further embodiments, said aromatic urethane unit is tolylene urethane. According to some embodiments, the polymeric chain comprises an urea unit. In certain embodiments, poly(urea-urethane) comprises an urea unit. In further embodiments, the polymeric chain is covalently bound to the crosslinking bridge through an urea unit. According to some embodiments, the polymeric chains are further dynamically connected via hydrogen bonds between the urea units of the polymeric chains.

In some embodiments the disulfide polymer is selected from poly(propylene-urethaneureaphenyl-disulfide), poly(urethane-carboxyphenyl-disulfide) and combinations thereof. In some embodiments the disulfide polymer is poly(propylene-urethaneureaphenyl-disulfide). In some embodiments the disulfide polymer is poly(urethane-carboxyphenyl-di sulfide).

The self-healing polymer can be prepared and mixed with the carbon powder as reported in Huynh Tan-Phat, Khatib M., Srour R., Plotkin M., Wu W., Vishinkin R., Hayek N., Jin H., Gazit O. M., Haick H. (2016). Composites of Polymer and Carbon Nanostructures for Self-Healing Chemical Sensors. Adv. Mater. Technol., 1: 1600187, the content of which is herein incorporated by reference in its entirety.

In some embodiments the at least one sensor comprises SWCNTs coated with crystal hexakis(n-dodecyl)-peri-hexabenzocoronene. In some embodiments the at least one sensor consists of SWCNTs coated with crystal hexakis(n-dodecyl)-peri-hexabenzocoronene. In some embodiments, the sensing unit comprises a single sensor comprising SWCNTs coated with crystal hexakis(n-dodecyl)-peri-hexabenzocoronene.

In some embodiments the at least one sensor comprises decanethiol-coated GNPs. In some embodiments the at least one sensor consists of decanethiol-coated GNPs. In some embodiments, the sensing unit comprises a single sensor comprising decanethiol-coated GNPs.

In some embodiments the sensing unit comprises a sensor array, comprising two sensors. In some embodiments, the sensing unit comprises a sensor array, comprising at least two sensors. In some embodiments, the sensor array comprises gold nanoparticles coated with at least two distinct thiols or disulfides. In some embodiments, the sensor array comprises gold nanoparticles coated with a thiol or disulfide and a conducting polymer. In certain embodiments, the sensors comprise: decanethiol-coated GNPs and hexanethiol-coated GNPs; decanethiol-coated GNPs and dodecanethiol-coated GNPs; or octadecanethiol-coated GNPs and decanethiol-coated GNPs; or PDPP-TNT and 2-nitro-4-(trifluoromethyl)benzenethiol-coated GNPs. Each possibility represents a separate embodiment of the invention. In further embodiments, the sensor array consists of: decanethiol-coated GNPs and dodecanethiol-coated GNPs; or octadecanethiol-coated GNPs and decanethiol-coated GNPs; or PDPP-TNT and 2-nitro-4-(trifluoromethyl)benzenethiol-coated GNPs. Each possibility represents a separate embodiment of the invention.

In some embodiments, the sensing unit comprises a sensor array, comprising three sensors. In some embodiments, the sensing unit comprises a sensor array, comprising at least three sensors. In some embodiments, the sensor array comprises gold nanoparticles coated with at least three distinct thiols or disulfides. In some embodiments, the sensor array comprises gold nanoparticles coated with at least two distinct thiols or disulfides and a conducting polymer. In some embodiments, the sensor array comprises gold nanoparticles coated with at least two distinct thiols or disulfides and SWCNTs coated with PAH or derivatives thereof. In some embodiments, the sensor array comprises gold nanoparticles coated with a thiol or disulfide, SWCNTs coated with PAH or derivatives thereof, and a conducting polymer. In some embodiments, the sensor array comprises gold nanoparticles coated with at least two distinct thiols or disulfides and a conductive polymer composite. In certain embodiments, the sensors comprise: PDPP-TNT, tert-dodecanethiol-coated GNPs, and 3-ethoxythiophenol-coated GNPs; or decanethiol-coated GNPs, PDPP-TNT, and dodecanethiol-coated GNPs; or 2-nitro-4-(trifluoromethyl)benzenethiol-coated GNPs, 3-ethoxythiophenol-coated GNPs, and 2-ethylhexanethiol-coated GNPs; or 2-ethylhexanethiol-coated GNPs, dibutyl disulfide-coated GNPs, and 3-ethoxythiophenol-coated GNPs; or SWCNTs coated with crystal hexakis(n-dodecyl)-peri-hexabenzocoronene, 2-naphthalenethiol-coated GNPs, and PDPP-TNT; or octadecanethiol-coated GNPs chemiresistor, benzyl mercaptan-coated GNPs chemiresistor and 2-ethylhexanethiol-coated GNPs; or 3-ethoxythiophenol-coated GNPs, tert-dodecanethiol-coated GNPs, and 4-chlorobenzenemethanethiol-based GNPs; or PDPP-TNT, decanethiol-coated GNPs and dibutyl disulfide-coated GNPs; or dibutyl-disulfide-coated GNPs, a composite of carbon black with poly(propylene-urethaneureaphenyl-disulfide) and 2-naphthalenethiol-based GNPs. Each possibility represents a separate embodiment of the invention.

In some embodiments, the sensing unit comprises a sensor array, comprising four sensors. In some embodiments, the sensing unit comprises a sensor array, comprising at least four sensors. In some embodiments, the sensor array comprises gold nanoparticles coated with at least four distinct thiols or disulfides. In some embodiments, the sensor array comprises gold nanoparticles coated with at least three distinct thiols or disulfides and a conducting polymer. In some embodiments, the sensor array comprises gold nanoparticles coated with at least three distinct thiols or disulfides and SWCNTs coated with PAH or derivatives thereof. In some embodiments, the sensor array comprises gold nanoparticles coated with a thiol or disulfide, SWCNTs coated with PAH or derivatives thereof, conducting polymer and a conductive polymer composite. In some embodiments, the sensors comprise: 2-ethylhexanethiol-coated GNPs, decanethiol-coated GNPs, dibutyl disulfide-coated GNPs and 3-ethoxythiophenol-coated GNPs; or 3-ethoxythiophenol-coated GNPs, dibutyl disulfide-coated GNPs, 2-nitro-4-(trifluoromethyl)benzenethiol-coated GNPs and 2-ethylhexanethiol-coated GNPs; or benzyl mercaptan-coated GNPs, 3-ethoxythiophenol-coated GNPs, octadecanethiol-coated GNPs and 2-ethylhexanethiol-coated GNPs; or tert-dodecanethiol-coated GNPs, benzyl mercaptan-coated GNPs, SWCNTs coated with crystal hexakis(n-dodecyl)-peri-hexabenzocoronene and 2-ethylhexanethiol-coated GNPs; decanethiol-coated GNPs, tert-dodecanethiol-coated GNPs, 2-nitro-4-(trifluoromethyl)benzenethiol-coated GNPs, and 2-ethylhexanethiol-coated GNPs; or SWCNTs coated with crystal hexakis(n-dodecyl)-peri-hexabenzocoronene, a composite of black carbon with poly(propyleneurethaneureaphenyl-disulfide) mixed with poly(urethanecarboxyphenyl-disulfide), 2-ethylhexanethiol-coated GNPs and PDPP-TNT. Each possibility represents a separate embodiment of the invention.

The terms "two sensors", "at least two sensors", "three sensors", "at least three sensors", "four sensors", and "at least four sensors", as used herein, refer in some embodiments to the number of distinct types of the sensors within the sensing unit.

In some embodiments the sensor is configured in a form selected from the group consisting of a capacitive sensor, a resistive sensor, a chemiresistive sensor, an impedance sensor, and a field effect transistor sensor. Each possibility is a separate embodiment of the invention.

In some embodiments, the signal measured upon exposure of the at least one sensor to the test sample is an electrical signal. In some embodiments the electrical signal is selected from the group consisting of resistance, conductance, alternating current (AC), frequency, capacitance, impedance, inductance, electrical potential, and voltage threshold. Each possibility is a separate embodiment of the invention.

The Sensing Unit

In some embodiments the sensing unit further comprises a substrate. In some embodiments, the substrate is rigid. In other embodiments, the substrate is flexible. The non-limiting examples of suitable substrates include paper, polymer, silicon dioxide, silicon rubber, ceramic material, metal, insulator, semiconductor, semimetals and combinations thereof. The polymer can be selected from polyamide, polyimide, polyester, polyimine, polyethylene, polyethylene terephthalate, polyvinyl chloride (PVC), polydimethylsiloxane, polystyrene, and derivatives and combinations thereof. In some embodiments the substrate is made of at least one of PVC, polyimide film, polyethylene, biaxially-oriented polyethylene terephthalate, glass and silicone. Each possibility represents a separate embodiment of the invention.

In further embodiments, the sensing unit comprises at least two electrodes on said substrate. In further embodiments, the at least two electrodes are in electric contact with the at least one sensor. In some embodiments, the electrodes are coupled to the sensor' material. In some embodiments, the sensor material is applied onto the electrodes. The electrodes, which are coupled to the sensor' material and/or are disposed beneath the sensors' material can enable the measurement and transmittance of the electric signals generated by the sensor. The at least two electrodes can be further used to apply a constant current or potential to the sensor. In certain such embodiments, the measured signal of the at least one sensor is potential or current change, respectively.

In some embodiments the sensing unit comprises a substrate and at least three electrodes on said substrate. In some embodiments the sensing unit further comprises a substrate and a plurality of electrodes on said substrate. In some embodiments the distance between the electrodes is between 0.3 µm and 400 µm. In some embodiments the distance between the electrodes is between 0.5 µm and 300 µm. In some embodiments the distance between the electrodes is between 1 µm and 200 µm.

In some embodiments, the sensing unit comprises an electrode array. The electrode array can include a pair of electrodes (a positive electrode and a negative electrode) or a plurality of said pairs of electrodes. The electrode array can further comprise patterned electrodes, for example, interdigitated electrodes. In some embodiments, the electrode array includes a plurality of interdigitated electrodes sets. The interdigitated electrodes can have any shape known in the art, such as, but not limited to circular or rectangular shapes. Alternatively, the electrode array may include a source and a drain electrode separated from one another by a source-drain gap. The electrode array may further comprise a gate electrode wherein the electric signal may be indicative of a certain property of the conducting polymer film under the influence of a gate voltage.

The electrode array can comprise any metal having high conductivity. The non-limiting examples of suitable metals suitable include Au, Ti, Cu, Ag, Pd, Pt, Ni, and Al.

In some embodiments, the sensing unit further comprises at least one sensor selected from the group consisting of a temperature sensor, a humidity sensor, and a touch sensor. In certain embodiments, the sensing unit further comprises a temperature sensor, a humidity sensor, or both. Each possibility represents a separate embodiment of the invention.

The sensing unit suitable for use in the real-time diagnosing method and in the skin-mountable medical device can have the same or different structure.

VOCs and SVOCs

As mentioned hereinabove, the present invention is based in part on the surprising finding that nanoparticle- and polymer-based sensors can detect skin-emitted or excreted VOCs and SVOCs, which are indicative of tuberculosis. In some embodiments, the VOCs or SVOCs, which are indicative of tuberculosis are selected from 2-methylbutane, 2,2,4,6,6-pentamethylheptane, cyclopentane, isopropyl alcohol, 2,3-dimethyl-2,3-butanediol, diisobutyl phthalate, squalene, xylene and combinations thereof. In certain embodiments, the VOCs or SVOCs, which are indicative of tuberculosis are selected from 2-methylbutane, 2,2,4,6,6-pentamethylheptane, cyclopentane, 2,3-dimethyl-2,3-butanediol, diisobutyl phthalate, squalene, xylene and combinations thereof. In some embodiments, tuberculosis is pulmonary tuberculosis.

In some embodiments, the at least one sensor is configured to detect at least one VOC or SVOC selected from the group consisting of 2-methylbutane, 2,2,4,6,6-pentamethylheptane, cyclopentane, isopropyl alcohol, diisobutyl phthalate, squalene, xylene and 2,3-dimethyl-2,3-butanediol. In some embodiments the at least one sensor is configured to detect at least two VOCs or SVOCs selected from the group consisting of 2-methylbutane, 2,2,4,6,6-pentamethylheptane, cyclopentane, isopropyl alcohol, diisobutyl phthalate, squalene, xylene and 2,3-dimethyl-2,3-butanediol. In some embodiments the at least one sensor is configured to detect at least three VOCs or SVOCs selected from the group consisting of 2-methylbutane, 2,2,4,6,6-pentamethylheptane, cyclopentane, isopropyl alcohol, diisobutyl phthalate, squalene, xylene and 2,3-dimethyl-2,3-butanediol. In some embodiments the at least one sensor is configured to detect at least four VOCs or SVOCs selected from the group consisting of 2-methylbutane, 2,2,4,6,6-pentamethylheptane, cyclopentane, isopropyl alcohol, and 2,3-dimethyl-2,3-butanediol. In some embodiments the at least one sensor is configured to detect at least five VOCs or SVOCs comprising 2-methylbutane, 2,2,4,6,6-pentamethylheptane, cyclopentane, isopropyl alcohol, diisobutyl phthalate, squalene, xylene and 2,3-dimethyl-2,3-butanediol. In certain embodiments, said VOCs or SVOCs are indicative of pulmonary tuberculosis.

In some embodiments, the at least one sensor is configured to detect at least one VOC or SVOC selected from the group consisting of 2-methylbutane, 2,2,4,6,6-pentamethylheptane, cyclopentane, diisobutyl phthalate, squalene, xylene and 2,3-dimethyl-2,3-butanediol. In further embodiments, the at least one sensor is configured to detect at least two of said VOCs or SVOCs. In still further embodiments, the at least one sensor is configured to detect at least four of said VOCs or SVOCs. In certain embodiments, said VOCs or SVOCs are indicative of pulmonary tuberculosis.

Measuring the Signal of the at Least One Sensor

The signal of the at least one sensor can be detected by a suitable detection and/or measuring device. Thus, in some embodiments, the sensing unit is coupled to the signal detection and/or measuring device. Suitable detection and/or measuring devices should be susceptible to a change in any one or more of resistance, conductance, alternating current (AC), frequency, capacitance, impedance, inductance, mobility, electrical potential, piezoelectricity, and voltage threshold. Each possibility represents a separate embodiment of the present invention. In additional embodiments, the measuring devices are susceptible to swelling or aggregation of the conducting polymer, the conductive polymer composite and/or conductive nanostructures. Each possibility represents a separate embodiment of the present invention. Changes in the electric properties of the sensor(s), such as resistance, conductance, direct or alternating current, capacitance, impedance, electrical potential, or voltage threshold can be measured by any suitable device known in the art, including, inter alia, a data logger, a potentiostat, a voltmeter, a conductivity meter, an LCR meter or a millimeter. Changes in the piezoelectricity properties of the sensor(s) can be measured using, for example, a piezoelectric sensor.

In certain embodiments, the measured signals are transmitted to a processing unit. The measured signals can be transmitted to a remote server and/or portable electronic device. Additionally or alternatively, the measured signals can be displayed on a display.

The Reference

According to some aspects and embodiments of the invention, the output signal of the at least one sensor is compared to a reference. As used herein, the terms "reference" and "reference value" are interchangeable and refer to a threshold criterion/value to which measured signals are compared in order to obtain an identification of the presence of pulmonary tuberculosis. The reference value can be derived in any one of a number of manners. For example, the reference value may be based on a collection of data of samples from subjects known to be afflicted with tuberculosis. Additionally or alternatively, the reference value may be based on a collection of data of samples from subjects known to be TB negative. In some embodiments, the reference value is derived from a collection of data of samples from subjects known to be afflicted with tuberculosis and subjects known to be TB negative.

According to certain aspects and embodiments, the reference value is determined from statistical analysis of studies that compared VOCs and SVOCs profiles of subjects with known clinical outcomes and correlated them with the corresponding electrical signals of the sensors of the present invention. Accordingly, the reference value may be obtained from data collected from a sample population of subjects, which acts as a pool of data from which normalized expected differences in electrical responses for TB positive and TB negative subjects can be determined. The reference value is then generated by selecting the value of electrical signal that is determined as the cut-off for classifying TB positive and TB negative samples. The reference value may be varied according to subject parameters such as age, sex, height, weight, race, interventions, or the like.

In some embodiments the reference value is determined from a database of responses of the at least one sensor to skin-emitted or excreted VOCs or SVOCs of subjects afflicted with pulmonary tuberculosis. In some embodiments the reference value is determined from a database of responses of the at least one sensor to skin-emitted or excreted VOCs or SVOCs of subjects known to be TB negative. In some embodiments the reference value is determined from a database of responses of the at least one sensor to skin-emitted or excreted VOCs or SVOCs of subjects afflicted with pulmonary tuberculosis and subjects known to be TB negative. In some embodiments the subjects afflicted with pulmonary tuberculosis are HIV positive subjects afflicted with pulmonary tuberculosis. In some embodiments the subjects known to be TB negative are HIV positive subjects known to be TB negative.

In some embodiments the subjects afflicted with pulmonary tuberculosis are at least two subjects afflicted with pulmonary tuberculosis. In some embodiments the subjects afflicted with pulmonary tuberculosis are at least three subjects afflicted with pulmonary tuberculosis. In some embodiments the subjects afflicted with pulmonary tuberculosis are at least four subjects afflicted with pulmonary tuberculosis. In some embodiments the subjects afflicted with pulmonary tuberculosis are at least five subjects afflicted with pulmonary tuberculosis. In some embodiments the subjects afflicted with pulmonary tuberculosis are at least ten subjects afflicted with pulmonary tuberculosis. In some embodiments the subjects afflicted with pulmonary tuberculosis are at least fifty subjects afflicted with pulmonary tuberculosis. In some embodiments the subjects afflicted with pulmonary tuberculosis are at least hundred subjects afflicted with pulmonary tuberculosis.

In some embodiments the subjects known to be TB negative are at least two subjects known to be TB negative. In some embodiments the subjects known to be TB negative are at least three subjects known to be TB negative. In some embodiments the subjects known to be TB negative are at least four subjects known to be TB negative. In some embodiments the subjects known to be TB negative are at least five subjects known to be TB negative. In some embodiments the subjects known to be TB negative are at least ten subjects known to be TB negative. In some embodiments the subjects known to be TB negative are at least fifty subjects known to be TB negative. In some embodiments the subjects known to be TB negative are at least hundred subjects known to be TB negative.

The statistical analysis of the comparison of the skin-emitted or excreted VOCs and SVOCs profiles of subjects with known clinical outcomes (e.g., TB positive or negative) can be performed by using various learning and pattern recognition algorithms. Said algorithms include, but are not limited to, unsupervised principal component analysis (PCA), discriminant function analysis (DFA), artificial neural networks (ANN) and support vector machine analysis (SVM).

PCA is a statistical method for data analysis that effectively reduces the multidimensional data space obtained from sensors array to its main components. The analysis extracts the most important information from the data space and hence compresses the size of the space while retaining as much as possible of the variation in the original data space. PCA creates new variables called principal components which are obtained as linear combinations of the original variables. The results of the analysis present a convenient visualization of the differentiation between the analyzed groups, meaning a projection of the data along principal components where the original data varies the most in mutually orthogonal dimensions. While the first principal component is required to have the largest possible variance, the second component is computed under the constraint of being orthogonal to the first component.

DFA is another method for data analysis when the groups to be discriminated are defined before the analysis is performed. The input variables for DFA are the features extracted from the response of the at least one sensor. The method determines linear combinations of the input variables in order to receive a minimum variance within each group and maximum variance between groups. Similarly to the PCA method, the DFA computes orthogonal principal components as output variables using linear transformation. Moreover, the first canonical variable is the most dominant discriminating dimension for binary approaches. For calcification of more than two groups, the next canonical variables might also represent additional dimensions of discrimination.

SVM is a supervised learning model with associated learning algorithms that analyze data and recognize patterns, used for classification and regression analysis. Given a set of training examples, each marked as belonging to one of two categories, an SVM training algorithm builds a model that assigns new examples into one category or the other, making it a non-probabilistic binary linear classifier.

The learning and pattern recognition algorithm for use in statistical analysis of the comparison of the skin-emitted or excreted VOCs and SVOCs profiles of subjects with known clinical outcomes can further be selected from multi-layer perception (MLP), generalized regression neural network (GRNN), fuzzy inference system (FIS), self-organizing map (SOM), radial bias function (RBF), genetic algorithm (GAS), neuro-fuzzy system (NFS), adaptive resonance theory (ART), partial least squares (PLS), multiple linear regression (MLR), principal component regression (PCR), linear discriminant analysis (LDA), cluster analysis, and nearest neighbor. Each possibility represents a separate embodiment of the present invention.

Additional algorithms, which can be used in the methods and devices of the present invention, include Fisher linear discriminant analysis (FLDA), soft independent modeling of class analogy (SIMCA), K-nearest neighbors (KNN), genetic algorithms, and fuzzy logic algorithms and canonical discriminant analysis (CDA).

In some exemplary embodiments, the learning and pattern recognition algorithm is DFA.

Statistically significant differences between principal component scores or groups obtained using the learning and pattern recognition algorithms can be studied using ANOVA, Wilcoxon, Student's t-test or combinations thereof. Sensitivity and specificity of the sample separation from the learning and pattern recognition algorithm can be evaluated, for example, by leave-one-out cross-validation or K-fold analysis.

According to some embodiments, prior to applying the algorithm to the measured response of the at least one sensor, feasibility of the algorithm is evaluated by using the database of response patterns.

The statistical analysis of the comparison of the skin-emitted or excreted VOCs and SVOCs profiles of subjects with known clinical outcomes can further involve supervised models. In some embodiments, the supervised models include artificial neural networks; chaotic models; (DFA; and a combination of ANN and chaotic parameters, fuzzy or cellular automated-based models. The models can be validated in an attempt to identify the minimum number of failures in the diagnosis and VOCs present in real samples and, also, the most important information hidden in the output signals of sensors. For this purpose the number of true positive (TP), true negative (TN), false positive (FP) and false negative (FN) predictions can be determined, Then, classification accuracy can be defined by calculating the sensitivity and specificity of the built model, while Sensitivity=TP/(TP+FN); Specificity=TN/(TN+FP) and Accuracy=(TP+TN)/n.

Other classification techniques that are known to those skilled in statistical data analysis can be used as well. Regardless of the classification technique that is used, the technique and its application in this context are readily susceptible to computerized implementation. For example, pattern recognition and data classification can be conducted using MATLAB® (The MathWorks).

In some embodiments, the step of comparing the response of the at least one sensor to the reference value is performed by a computing system configured for executing various algorithms stored on a non-transitory memory. In certain such embodiments, the sensing unit is coupled to said computing system.

In some embodiments, the step of comparing the response of the at least one sensor to the reference value is performed by a processing unit. In certain embodiments, said processing unit is a part of the skin-mountable medical device.

In some embodiments, the step of comparing the response of the at least one sensor to the reference value is performed by a remote sensor. In some embodiments, the step of comparing the response of the at least one sensor to the reference value is performed by a portable electronic device. In certain such embodiments, the skin-mountable medical device is configured to transmit the output signal of the at least one sensor to a remote server and/or a portable electronic device.

Response Induced Parameters

The output signal of the at least one sensor can be analyzed to extract a plurality of response induced parameters (also termed "sensing features" hereinbelow). The output signal of the at least one sensor upon exposure to a test sample can change with time. Typically, the signal increases or decreases upon the exposure until reaching steady state and decreases and/or increases, respectively, upon the removal of the test sample. According to some embodiments, the output signal of the at least one sensor comprises a plurality of response induced parameters. In some embodiments, the computing system configured for executing various algorithms stored on a non-transitory memory extracts a plurality of response-induced parameters from the output signal of the at least one sensor. In some embodiments, the processing unit extracts a plurality of response-induced parameters from the output signal of the at least one sensor. In some embodiments, the remote server and/or the portable electronic device extract a plurality of response-induced parameters from the output signal of the at least one sensor.

In some embodiments, said plurality of response induced parameters extracted from the output signal of the at least one sensor is analyzed by the learning and pattern recognition algorithm.

In some embodiments, the database of responses of the at least one sensor to skin-emitted or excreted VOCs or SVOCs of subjects afflicted with pulmonary tuberculosis and/or of subjects that are TB negative includes a plurality of response-induced parameters. In some embodiments, the reference value is generated by selecting the value of the response induced parameter that is determined as the cut-off for classifying TB positive and TB negative samples.

Without wishing to being bound by theory or mechanism of action, extraction of the plurality of response induced parameters, from the output signal of the at least one sensor allows to improve accuracy, sensitivity and/or specificity of the at least one sensor. Extracting a plurality of response induced parameters can further allow decreasing the minimal number of sensors in the sensing unit required to provide diagnosing of tuberculosis.

The plurality of response induced parameters can include at least two response induced parameters. According to other embodiment, the plurality of response induced parameters includes at least three response induced parameters, at least four response induced parameters, at least five response induced parameters, at least six response induced parameters, or at least seven response induced parameters. Each possibility represents a separate embodiment of the invention.

The response induced parameters can be selected from steady state normalized response, the time interval for obtaining steady state normalized response, and the time required to reach baseline after removal of the test sample. In some embodiments, the response induced parameters include full non steady state response at the beginning of the signal, full non steady state response at the beginning of the signal normalized to baseline, full non steady state response at the middle of the signal, full non steady state response at the middle of the signal normalized to baseline, full steady state response, full steady state response normalized to baseline, area under non steady state response, area under steady state response, the gradient of the response upon exposure to the test sample, the gradient of the response upon removal of the test sample, the time required to reach a certain percentage of the response, such as the time required to reach 10%, 20%, 30%, 40%, 50%, 60%, 70%, 80%, 90% or 100% of the response upon exposure to the test sample, and the time required to reach a certain percentage of the response, such as the time required to reach 100%, 90%, 80%, 70%, 60%, 50%, 40%, 30%, 20% or 10% of the response upon removal of the test sample. Each possibility represents a separate embodiment of the invention.

In certain embodiments, the response-induced parameters are selected from the group consisting of full non-steady state response at the beginning of the signal, full non-steady state response at the beginning of the signal normalized to baseline, full non-steady state response at the middle of the signal, full non-steady state response at the middle of the signal normalized to baseline, full steady state response, full steady state response normalized to baseline, area under non-steady state response, area under steady state response, the gradient of the response upon exposure of the at least one sensor, and the time required to reach 10%, 20%, 30%, 40%, 50%, 60%, 70%, 80%, 90% or 100% of the response upon exposure of the at least one sensor.

In particular embodiments, the response-induced parameters are selected from the group consisting of the normalized change of sensor's resistance at the full non steady state response at the middle of the signal normalized to baseline, the full non steady state response at the peak of the signal normalized to baseline, the full steady state response at the end of the signal normalized to baseline, and the area under steady state response. In certain embodiments, at least two of said response induced parameters are extracted from the output signals of the at least one sensor. Optionally, at least three of said response-induced parameters are extracted from the output signals. In other embodiments, the response-induced parameters extracted from the output signal include the normalized change of sensor's resistance at the full non steady state response at the middle of the signal normalized to baseline, the full non steady state response at the peak of the signal normalized to baseline, the full steady state response at the end of the signal normalized to baseline, and the area under steady state response.

In certain embodiments, database of responses of the at least one sensor to skin-emitted or excreted VOCs or SVOCs of subjects afflicted with pulmonary tuberculosis and/or of subjects that are TB negative includes at least two of said response induced parameters. Optionally, the database includes at least three of said response-induced parameters. In other embodiments, the database includes the normalized change of sensor's resistance at the full non steady state response at the middle of the signal normalized to baseline, the full non steady state response at the peak of the signal normalized to baseline, the full steady state response at the end of the signal normalized to baseline, and the area under steady state response.

In another embodiment, the plurality of response induced parameters are extracted from the output signal of the at least one sensor, including a change in resistance, impedance, capacitance, inductance, conductivity, and optical properties of the sensor upon exposure thereof to the breath sample. Each possibility represents a separate embodiment of the invention. In a particular embodiment, the plurality of response induced parameters are extracted from a change in resistance or conductivity of the at least one sensor.

Skin-Mountable Medical Device

In some aspects and embodiments of the invention there is provided a skin-mountable medical device for diagnosing tuberculosis in a subject, said device comprising a flexible fixing unit and a sensing unit comprising at least one sensor comprising at least one of conductive nanostructures coated with an organic coating, a conducting polymer and a conductive polymer composite.

In some currently preferred embodiments, said skin-mountable device provides real-time diagnosing of tuberculosis. In further embodiments, said skin-mountable device provides real-time diagnosing of pulmonary tuberculosis.

In some embodiments the fixing unit has two opposing surfaces forming a structure comprising an internal face and an external face. In further embodiments, said internal face contacts said sensing unit and is faces the skin during use. In still further embodiments, the sensing unit is disposed on said internal face of the fixing unit. In particular embodiments, the sensing unit is attached to said internal face. The sensing unit can be attached to the internal face of the fixing unit by any means as known in the art, as long as the attachment does not screen the at least one sensor from the skin of a subject, when the device is in use. In certain embodiments, the sensing unit is adhered to the internal face of the fixing unit.

In some embodiments, the fixing unit is configured to provide contact between the sensing unit and the skin of the subject. In further embodiments, the fixing unit enables positioning of the device on the skin of the subject. In still further embodiments, the fixing unit provides fixation of the device on the skin of the subject. In certain such embodiments, the surface of the internal face of the fixing unit should be sufficient to accommodate the sensing unit and to allow fixation of the device on the skin of the subject.

In some embodiments the fixing unit comprises an adhesive surface. In further embodiments, the internal face of the fixing unit comprises an adhesive surface. In some embodiments, the sensing unit is disposed on said adhesive surface of the internal strap. In some embodiments the internal face is mountable to the skin. In some embodiments the internal face is adhered to the skin. It is to be understood that the internal face is adhered to the skin except for the internal face surface, on which the sensing unit is disposed. In some embodiments the adhesive is a water resistant adhesive.

In certain embodiments, the fixing unit is in the form of a plaster. The skin-mountable devices according to some embodiments of the invention can be integrated into wearable articles, for example by incorporating the sensing unit into plasters or adhesive bandages, which stick to the subject's skin.

Adhesives, such as, but not limited to, acrylic adhesives, rubber adhesives, and silicone adhesives, which are typically used for formation of plasters, may be used as adhesives for the devices of the invention, so long that they are devoid of compounds, which may result in false positive indication of the sensor(s). Such compounds include VOCs and SVOCs, which are detectable by the sensor(s). Thus, the adhesive material, according to some embodiments, has a vapor pressure of below about 0.4 mm Hg at 25° C.

In some embodiments the fixing unit comprises a flexible strap. In certain embodiments, said strap comprises connectable ends, such as, but not limited to, Velcro® hook and loop fasteners.

The fixation of the device and its sensing unit to the skin also enables the isolation of skin area, from which a test sample(s) is derived, from the environment, thus reducing the concentration of VOCs and SVOCs, originating from the subject's environment, and increasing the concentration VOCs and SVOCs emitted or excreted from the skin of the subject in the test sample, thereby improving the sensor(s) accuracy, sensitivity and/or specificity. In some embodiments the fixing unit is configured to substantially isolate skin area from the environment, when mounted on said skin area. In some embodiments the internal face is configured to substantially isolate skin area from the environment, when mounted on said skin area. In some embodiments the internal face is configured to substantially isolate the headspace of the skin from the environment, when mounted thereto.

The term "headspace of the skin" as used herein refers to the volume above the skin, when the volume is substantially sealed. The headspace of the skin volume contains a mixture of VOC and SVOCS, which may be indicative of a disease, including, inter alia, pulmonary tuberculosis.

In some embodiments the device further comprises at least one separation membrane located on the internal face of the fixing unit, configured to separate the at least one sensor from the skin, when in use. In general, a separation membrane may provide a barrier between sweat emitted from the skin of the user and the sensing unit, for reduction of the effects caused by the humidity. In addition, a membrane may protect the skin from the nanomaterials in the sensing unit. Such membrane can be hydrophobic and/or oleophobic. The non-limiting examples of suitable membrane materials include polytetrafluoroethylene (PTFE), polyethersulfone (PES) polymers and their derivatives. In some embodiments the at least one separation membrane comprises polytetrafluoroethylene and/or polyethersulfone. In certain embodiments, the at least one separation membrane is permeable to the VOCs and SVOCs emitted or excreted from skin. In some embodiments, the at least one separation membrane is vapor permeable.

The various embodiments of the sensing unit of the skin-mountable device and the at least one sensor are described hereinabove.

In some embodiments the skin-mountable device comprises a detection device configured to measure the output signal of the at least one sensor, as described hereinabove.

In some embodiments the skin-mountable device further comprises a flexible battery. In some embodiments the flexible battery is attached to the internal face of the fixing unit. In some embodiments the flexible battery is attached to the external face of the fixing unit. In some embodiments the flexible battery incorporates an integrating energy harvesting technology.

In some embodiments the skin-mountable medical device further comprises a processing unit and/or a transmitter.

In some embodiments the skin-mountable medical device comprises a processing unit. In some embodiments the at least one sensor is configured to transmit an output signal to the processing unit upon detection of at least one VOC or SVOC emitted or excreted from the skin. In some embodiments the at least one sensor is configured to transmit an output signal to the processing unit upon adsorption of at least one VOC or SVOC emitted or excreted from the skin on the material of said sensor. In some embodiments the at least one sensor is configured to transmit an output signal to the processing unit upon absorption of at least one VOC or SVOC emitted or excreted from the skin in the material of said sensor. In some embodiments the at least one sensor is configured to transmit an output signal to the processing unit upon occurrence of a redox reaction involving the material of said sensor, induced by the at least one VOC or SVOC emitted or excreted from the skin.

In some embodiments the processing unit is disposed on the external face of the fixing unit. In some embodiments, the processing unit is communicatively coupled to the sensing unit and/or to the measuring device. In some embodiments, the processing unit is electronically coupled to the sensing unit and/or to the measuring device.

In some embodiments the processing unit is configured to analyze the output signal of the at least one sensor measured by the detection device. In some embodiments, the processing unit receives an output signal of the at least one sensor and compares said signal to a reference. In further embodiments, the processing unit provides a positive indication signal or a negative indication signal following the analysis of the output signal of the at least one sensor, thereby enabling real-time diagnosing of tuberculosis. In some embodiments the processing unit provides a positive indication signal, thereby enabling real-time diagnosing of tuberculosis.

In some embodiments, the processing unit of the device further comprises an algorithm configured to differentiate between the response of the at least one sensor to the VOCs or SVOCs and the response of said at least one sensor to a stimulus selected from the group consisting of temperature, humidity, lateral strain, and combinations thereof. Each possibility represents a separate embodiment of the invention.

In some embodiments the skin-mountable medical device further comprises a transmitter. In some embodiments the at least one sensor is configured to transmit an output signal to the transmitter upon detection of at least one VOC or SVOC emitted or excreted from the skin. In some embodiments the at least one sensor is configured to transmit an output signal to the transmitter upon adsorption of at least one VOC or SVOC emitted or excreted from the skin on the material of said sensor. In some embodiments the at least one sensor is configured to transmit an output signal to the transmitter upon absorption of at least one VOC or SVOC emitted or excreted from the skin in the material of said sensor. In some embodiments the at least one sensor is configured to transmit an output signal to the transmitter upon occurrence of a redox reaction involving the material of said sensor, induced by the at least one VOC or SVOC emitted or excreted from the skin.

In some embodiments the transmitter is disposed on the external face of the fixing unit. In some embodiments, the transmitter is communicatively coupled to the sensing unit and/or to a measuring device. In some embodiments, the transmitter is electronically coupled to the sensing unit and/or to a measuring device.

The transmitter can include a communication component for remote communication, as known in the art, including, inter alia, GSM/UMTS mobile broadband modem, Bluetooth, wireless data transmitter including Wi-Fi and communications satellites. Each possibility represents a separate embodiment of the invention.

In some embodiments, the transmitter receives an output signal of the at least one sensor and transmits said signal to a remote server and/or to a portable electronic device.

In some embodiments, the transmitter receives an output signal of the at least one sensor and transmits said signal to a remote server. The remote server can comprise an algorithm, which analyzes said output signal. In certain embodiments, the remote server comprises an algorithm, which compares said signal to a reference.

In some embodiments, the transmitter receives an output signal of the at least one sensor and transmits said signal to a portable electronic device. The portable electronic device can comprise an algorithm, which analyses said signal. In certain embodiments, the portable electronic device comprises an algorithm, which compares said signal to a reference. In some embodiments, the portable electronic device comprises a smartphone application, which compares said signal to a reference. The non-limiting examples of the suitable portable electronic devices include a smartphone, a tablet, and a Chromebook.

In some embodiments, the remote sensor provides a positive indication signal or a negative indication signal following the analysis of the output signal of the sensor, thereby enabling real-time diagnosing of tuberculosis. In some embodiments the remote sensor provides a positive indication signal, thereby enabling real-time diagnosing of tuberculosis.

In some embodiments, the portable electronic device provides a positive indication signal or a negative indication signal following the analysis of the output signal of the sensor, thereby enabling real-time diagnosing of tuberculosis. In some embodiments the portable electronic device provides a positive indication signal, thereby enabling real-time diagnosing of tuberculosis.

In some embodiments the positive indication is provided when the output signal is greater than a reference. In some embodiments the negative indication is provided when the output signal is smaller than a reference. The methods to obtain the reference, including the suitable learning and pattern recognition algorithms and its use are described hereinabove.

In some embodiments, the remote server further comprises an algorithm configured to differentiate between the response of the at least one sensor to the VOCs or SVOCs and the response of said at least one sensor to a stimulus selected from the group consisting of temperature, humidity, lateral strain, and combinations thereof. In some embodiments, the portable electronic device further comprises an algorithm configured to differentiate between the response of the at least one sensor to the VOCs or SVOCs and the response of said at least one sensor to a stimulus selected from the group consisting of temperature, humidity, lateral strain, and combinations thereof.

In some currently preferred embodiments, the skin-mountable device comprises the processing unit and the transmitter. In some embodiments, the transmitter is further configured to transmit the positive indication signal or the negative indication signal from the remote sensor and/or the portable electronic device to the processing unit. In some embodiments, the transmitter is further configured to transmit the positive indication signal or the negative indication signal from the processing unit to the remote server and/or the portable electronic device.

Without wishing to being bound by theory or mechanism of action, analyzing the signal by the processing unit is preferred when the connectivity to the remote server and/or portable electronic device is insufficient. In areas with good mobile or wireless connectivity, the analysis of the output signal of the at least one sensor is preferably performed by the remote server and/or portable electronic device, as it can include a greater amount of learning and pattern recognition algorithms and/or datasets than the processing unit of the device.

In some embodiments, the skin-mountable device furthers comprise a data storage unit, configured to store the positive indication signal and/or the negative indication signal on the device. Said indication signals can be obtained from the processing unit, the remote server, and/or the portable electronic device. Each possibility represents a separate embodiment of the invention. In certain embodiments, the data storage unit is configured to store the positive indication signal and/or the negative indication signal obtained from the processing unit.

In some embodiments, the skin-mountable device is coupled to a cloud storage system, configured to store the positive indication signal and/or the negative indication signal. Said indication signals can be obtained from the processing unit and/or from the remote computing system. Said indication signals can be obtained from the processing unit, the remote server, and/or the portable electronic device. Each possibility represents a separate embodiment of the invention.

In some embodiments, the skin-mountable device further comprises a geophysical location defining unit, such as, but not limited to, GPS.

The plurality of positive indication signals obtained by using the device of the invention can be stored and used for (near)real-time or future analysis. For example, said positive indication signals in combination with the geophysical location of the subject can provide beneficial data on spreading of tuberculosis, as well as allow alerting the population about a risk of tuberculosis infection. Accordingly, in some embodiments, the skin-mountable device is configured to receive an alert signal of a TB positive subject being in vicinity of the device. Said alert signal can be transmitted by any one of the remote server, portable electronic device or another skin-mountable device. Each possibility represents a separate embodiment of the invention. In certain embodiments, the skin-mountable device is configured to communicate with another skin mountable device of the invention.

In some embodiments, the skin-mountable device further comprises at least one indicator. In some embodiments, the processing unit is configured to transmit the positive indication signal or the negative indication signal to the at least one indicator, thereby displaying the diagnosis outcome. In some embodiments, the transmitter is configured to transmit the positive indication signal or the negative indication signal to the at least one indicator, thereby displaying the diagnosis outcome. The positive indication signal and/or a negative indication signal can be transmitted to the transmitter by the remote server and/or the portable electronic device.

In some embodiments the at least one indicator is selected from an acoustic indicator and a visual indicator. In some embodiments the at least one indicator comprises an acoustic indicator. In some embodiments the at least one indicator comprises a visual indicator. In some embodiments the indicator comprises a visual display selected from light-emitting diode (LED) and/or organic light-emitting diode (OLED).

The medical device can further comprise an additional indicator configured to provide indication that there is an insufficient concentration of VOCs and/or SVOCs for providing the diagnosis. In some embodiments the indication that there is an insufficient concentration of VOCs and/or SVOCs for providing the diagnosis, is generated in response to the output signal of the at least one sensor transmitted to the processing unit.

The medical device can further comprise an additional indicator configured to provide an alert signal indicating a threat of a potential tuberculosis infection. In certain embodiments, said alert signal is displayed by said additional indicator when a TB positive subject is in vicinity of the device.

In some embodiments, the medical device further comprises at least one sensor selected from the group consisting of a temperature sensor, a humidity sensor, and a touch sensor. In certain embodiments, the medical device further comprises a temperature sensor, a humidity sensor, or both. Each possibility represents a separate embodiment of the invention.

In some embodiments, the medical device further comprises a USB port.

In some embodiments, the medical device further incudes an absorbent material, as detailed hereinabove. The absorbent material layer can be disposed between the skin of the subject and the sensing unit or between the sensing unit and the flexible fixing unit. Each possibility represents a separate embodiment of the invention.

In some embodiments the medical device is configured to provide continuous monitoring of tuberculosis. In certain embodiments, tuberculosis monitoring is provided by prolonged wearing of the device.

FIG. 1 schematically represents skin-mountable device 100 according to some embodiments of the invention. Said skin mountable device comprises adhesive patch 102 comprising internal face 102a and external face 102b. Sensing unit 104 comprising sensor 106 and two electrodes 108 supported on flexible substrate 110 is disposed on internal face 102a of adhesive patch 102. Sensor 106 is configured to face the skin of the subject, when device 100 is in use. Separation membrane 105 is disposed on internal face 102a of adhesive patch 102 and is configured to separate sensor 106 from the skin of the subject when device 100 is in use to provide a barrier between sweat emitted from the skin and sensing unit 104. External face 102b comprises processing unit 112, flexible battery 114 and indicator 116, configured to display a positive or a negative indication signal.

The Method for the Real-Time Diagnosing of Tuberculosis

In some aspects and embodiments of the invention there is provided a method for the real-time diagnosing of tuberculosis in a subject utilizing the skin-mountable medical device according to the principles of the present invention.

In some embodiments, the method comprises providing the skin-mountable medical device of the invention and mounting the skin-mountable medical device on the skin of a subject, thus exposing the at least one sensor to at least one VOC or SVOC emitted or excreted from the skin.

In some embodiments, the fixing unit of the device comprises an internal face comprising adhesive surface. In further embodiments mounting the skin-mountable medical device on the skin of the subject comprises sticking the internal face of the flexible fixing unit to the skin of the subject. As the fixing strap may be in the form of an adhesive plaster, its fixation to the skin of the subject may be achieved through sticking the face, which comprises adhesives, to the skin. In some embodiments, the fixing unit of the device comprises a flexible strap. In further embodiments, mounting the skin-mountable medical device on the skin of the subject comprises fastening the flexible strap on a body part of a subject.

In some embodiments mounting the skin-mountable medical device on the skin of the subject further comprises substantially isolating the skin of the subject, which is in contact with the flexible fixing unit, from the environment.

In some embodiments, mounting the skin-mountable medical device on the skin of a subject comprises mounting the skin-mountable medical device on at least one of chest area skin, mastoid skin and brachium skin. In some embodiments the mounting the skin-mountable medical device on the skin of a subject comprises mounting the skin-mountable medical device on the chest area skin. In some embodiments the mounting the skin-mountable medical device on the skin of a subject comprises mounting the skin-mountable medical device on the mastoid skin. In some embodiments the mounting the skin-mountable medical device on the skin of a subject comprises mounting the skin-mountable medical device on the brachium skin.

In some embodiments the mounting the skin-mountable medical device on the skin of a subject comprises sticking the internal face of the flexible fixing unit to at least one of chest area skin, mastoid skin and brachium skin.

In some embodiments, mounting the skin-mountable medical device on the skin of a subject comprises fastening the flexible strap of the flexible fixing unit around at least one of the chest, head, neck and arm of the subject.

In some embodiments, the method comprises permanent mounting of the device. In certain embodiments, the method comprises mounting the device and wearing it for at least about 30 days. In further embodiments, the method comprises mounting the device and wearing it for at least about 45 days, 60 days, 90 days or 120 days. Each possibility represents a separate embodiment of the invention. Thus, in some embodiments, the method provides continuous monitoring of tuberculosis in a subject. In additional embodiments, the method allows identifying the onset of tuberculosis.

In some embodiments, the method further comprises removing the device from the skin of the subject and exposing it to the ambient air to reduce the concentration of the skin-emitted or excreted VOCs or SVOCs in the sensor material. In further embodiments, the method comprises repeated mounting of the skin-mountable medical device on the skin of the subject. Alternatively, the skin-mountable medical device can include a pump, configured to flush the sensor with ambient air after predetermined periods of exposure to skin-emitted or excreted VOCs or SVOCs.

In some embodiments, the method comprises measuring an output signal of the at least one sensor upon exposure thereof to the at least one VOC or SVOC. In some embodiments, the measuring step is performed after about 5 minutes to about 240 minutes following the mounting step. In some embodiments, the measuring step is performed continuously or repeatedly. In certain embodiments, the measuring step is performed at least about once a day. In further embodiments, the measuring step is performed at least about twice a day, at least about three times a day or at least about four times a day.

In some embodiments, the measuring step is performed by the measuring device, as described hereinabove.

In some embodiments, the method comprises analyzing the output signal of the at least one sensor. In some embodiments, the skin-mountable device comprises a processing unit. In further embodiments, the method comprises analyzing the output signal by the processing unit of the device. In some embodiments, the skin-mountable device comprises a transmitter. In some embodiments, the transmitter is configured to receive an output signal of the at least one sensor and transmit said signal to a remote server. In some embodiments, the transmitter is configured to receive an output signal of the at least one sensor and transmit said signal to a portable electronic device. In further embodiments, the method comprises analyzing the output signal by the remote sensor. In further embodiments, the method comprises analyzing the output signal by the portable electronic device.

In some embodiments, analyzing the output signal of the at least one sensor comprises comparing the output signal to a reference. Said comparison can involve application of various algorithms, as described hereinabove.

In some embodiments, analyzing the output signal of the at least one sensor comprises extracting a plurality of response-induced parameters from said signal, as described hereinabove. In certain embodiments, the response-induced parameters are selected from the group consisting of full non-steady state response at the beginning of the signal, full non-steady state response at the beginning of the signal normalized to baseline, full non-steady state response at the middle of the signal, full non-steady state response at the middle of the signal normalized to baseline, full steady state response, full steady state response normalized to baseline, area under non-steady state response, area under steady state response, the gradient of the response upon exposure of the at least one sensor, and the time required to reach 10%, 20%, 30%, 40%, 50%, 60%, 70%, 80%, 90% or 100% of the response upon exposure of the at least one sensor.

In certain embodiments, the sensing unit comprises a plurality of sensors. In some currently preferred embodiments, the signal of each sensor is analyzed independently. In further embodiments, the signal of each sensor is compared to a reference value. In still further embodiments, each response induced parameters extracted from the output signal is analyzed independently. In yet further embodiments, each response induced parameter is compared to a reference. In other embodiments, exposure of the plurality of sensors forms a response pattern, being analyzed by a learning a pattern recognition algorithm. In certain such embodiments, at least one of the processing unit and a remote server or portable electronic device comprises said learning a pattern recognition algorithm. The non-limiting examples of said algorithms include unsupervised principal component analysis (PCA), discriminant function analysis (DFA), artificial neural networks (ANN), support vector machine analysis (SVM), multi-layer perception (MLP), generalized regression neural network (GRNN), fuzzy inference system (FIS), self-organizing map (SOM), radial bias function (RBF), genetic algorithm (GAS), neuro-fuzzy system (NFS), adaptive resonance theory (ART), partial least squares (PLS), multiple linear regression (MLR), principal component regression (PCR), linear discriminant analysis (LDA), cluster analysis, nearest neighbor, Fisher linear discriminant analysis (FLDA), soft independent modeling of class analogy (SIMCA), K-nearest neighbors (KNN), genetic algorithms, and fuzzy logic algorithms and canonical discriminant analysis (CDA).

In some embodiments, the method comprises diagnosing tuberculosis if the output signal of the at least one sensor is greater than a reference. In further embodiments, diagnosing tuberculosis comprises transmitting the positive indication signal or the negative indication signal to the at least one indicator, thereby displaying the diagnosis outcome. The positive indication signal or the negative indication signal can be transmitted from the processing unit. In other embodiments, the positive indication signal or the negative indication signal are transmitted from the remote server or from a portable electronic device through a transmitter.

In some embodiments, diagnosing tuberculosis comprises transmitting the positive indication signal or a negative indication signal from the processing unit to the remote server and/or the portable electronic device.

The Method of Diagnosing Pulmonary Tuberculosis by Analyzing VOCs or SVOCs Indicative of Tuberculosis In some aspects and embodiments of the invention there is provided a method of diagnosing tuberculosis, which involves determining the levels of specific VOCs and SVOCs emitted or excreted from subject's skin, which are tuberculosis biomarkers. As mentioned hereinabove, it was surprisingly found by the inventors that specific skin-emitted VOCs and SVOCs can be used as tuberculosis biomarkers even following the derivation thereof from the skin.

Thus, according to another aspect there is provided a method of diagnosing tuberculosis in a subject, comprising the steps of placing an absorbent material on the skin of the subject for a predetermined period of time, thereby obtaining a test sample comprising at least one volatile organic compound (VOC) or semi-volatile organic compound (SVOC) emitted or excreted from the skin of the subject; retrieving the test sample from the absorbent material; determining the level of at least one VOC or SVOC selected from the group consisting of 2-methylbutane, 2,2,4,6,6-pentamethylheptane, cyclopentane, isopropyl alcohol, 2,3-dimethyl-2,3-butanediol diisobutyl phthalate, squalene and xylene in the retrieved test sample; and comparing the level of the at least one VOC or SVOC from the test sample with the level of said at least one VOC or SVOC in a control sample, whereby a significantly different level of said at least one VOC or SVOC in the test sample as compared to the level of said compound in the control sample is indicative of tuberculosis.

The steps of placing an absorbent material on the skin of the subject for a predetermined period of time and obtaining a test sample can be similar to the corresponding steps in the non-real time diagnosing method, as described hereinabove.

In some embodiments the method comprises the step of determining the levels of a plurality of VOCs or SVOCs. In some embodiments the method comprises the step of determining the levels of at least two VOCs or SVOCs. In some embodiments the method comprises the step of determining the levels of at least three VOCs or SVOCs. In some embodiments the method comprises the step of determining the levels of at least four VOCs or SVOCs. In some embodiments the method comprises the step of determining the levels of at least five VOCs or SVOCs, at least six VOCs or SVOCs or at least seven VOCs or SVOCs. Each possibility represents a separate embodiment of the invention. In certain embodiments, the method comprises the step of determining the levels of each VOCs or SVOCs from the above list.

In some embodiments the at least one VOC or SVOC is selected from the group consisting of 2-methylbutane, 2,2,4,6,6-pentamethylheptane, cyclopentane, 2,3-dimethyl-2,3-butanediol, diisobutyl phthalate, squalene, xylene and combinations thereof. In some embodiments the at least two VOCs or SVOCs are selected from the group consisting of 2-methylbutane, 2,2,4,6,6-pentamethylheptane, cyclopentane, 2,3-dimethyl-2,3-butanediol, diisobutyl phthalate, squalene, xylene and combinations thereof. In some embodiments the at least three VOCs or SVOCs are selected from the group consisting of 2-methylbutane, 2,2,4,6,6-pentamethylheptane, cyclopentane, 2,3-dimethyl-2,3-butanediol, diisobutyl phthalate, squalene, xylene and combinations thereof. In some embodiments the at least four VOCs or SVOCs are selected from the group consisting of 2-methylbutane, 2,2,4,6,6-pentamethylheptane, cyclopentane, 2,3-dimethyl-2,3-butanediol, diisobutyl phthalate, squalene, xylene and combinations thereof.

In some embodiments the step of determining the level of the at least one VOC or SVOC comprises the use of at least one technique selected from the group consisting of Gas-Chromatography (GC), GC-lined Mass-Spectrometry (GC-MS), Proton Transfer Reaction Mass-Spectrometry (PTR-MS), Electronic nose device, and Quartz Crystal Microbalance (QCM). Each possibility represents a separate embodiment of the invention.

In certain embodiments, the step of determining the level of the at least one VOC or SVOC comprises the use of GC-MS. In further embodiments, the GC-MS is combined with a thermal desorption system.

Gas Chromatography (GC) linked to mass spectrometry (MS) is often used to determine the chemical identity and composition of breath VOCs (Miekisch et al. Clinica Chimica Acta, 2004, 347, 25-39). In this set-up, the GC utilizes a capillary column having characteristic dimensions (length, diameter, film thickness) as well as characteristic phase properties. The difference in the chemical properties of different molecules in a mixture allows the separation of the molecules as the sample travels through the column, wherein each molecule has a characteristic time (termed retention time) in which it passes through the column under set conditions. This allows the mass spectrometer to capture, ionize, accelerate, deflect, and detect the ionized molecules separately. The MS signal is obtained by ionization of the molecules or molecular fragments and measurement of their mass to charge ratio by comparing it to a reference collection.

In some embodiments, the molecular structures of the VOCs or SVOCs are determined by spectral library match. In other embodiments, the molecular structures of the VOCs or SVOCs are determined by measuring pure standards of the relevant chemicals.

In certain embodiments, the level of the at least one VOC or SVOC in the test sample is significantly increased as compared to the level of said compound in a control sample. According to other embodiments, the level of the at least one VOC or SVOC in the test sample is significantly decreased as compared to the level of said compound in a control sample.

The control samples, according to some embodiments, are obtained from a control individual, i.e., an individual not having tuberculosis or any other chronic disease.

The term "significantly different" as used herein refers to a quantitative difference in the concentration or level of the VOC or SVOC from the test sample as compared to the level of said VOC or SVOC in control samples obtained from individuals not having tuberculosis. A statistically significant difference can be determined by any test known to the person skilled in the art. Common tests for statistical significance include, as mentioned hereinabove, t-test, ANOVA1 Kruskal-Wallis, Wilcoxon, Mann-Whitney and odds ratio. Individual samples (of unknown status) can be compared with data from the reference group (negative control). An increase or decrease in the level as compared to a control or reference value or mean control level or reference value, or a change, difference or deviation from a control or reference value, can be considered to exist if the level differs from the control level or reference value, by about 5% or more, by about 10% or more, by about 20% or more, or by about 50% or more compared to the control level or reference value. Statistical significance may alternatively be calculated as P<0.05. Methods of determining statistical significance are known and are readily used by a person of skill in the art. In a further alternative, increased levels, decreased levels, deviation, and changes can be determined by recourse to assay reference limits or reference intervals. These can be calculated from intuitive assessment or non-parametric methods. Overall, these methods calculate the 0.025, and 0.975 fractiles as 0.025*(n+1) and 0.975*(n+1). Such methods are well known in the art. The presence of a VOC or SVOC marker which is absent in a control sample, is also contemplated as an increased level, deviation or change. The absence of a VOC or SVOC marker which is present in a control, for example, is also contemplated as a decreased level, deviation or change. In some embodiments, individual samples (of unknown status) can be compared with data obtained from a positive control group known to have tuberculosis. In accordance with these embodiments, a significantly different level of at least one VOC in the test sample as compared to the level of said compound in the control sample would be diagnosed as is known in the art.

According to some embodiments, the significant difference in the level of the at least one VOC or SVOC in the test sample as compared to the level of said compound in the control sample, wherein said difference is indicative of tuberculosis, comprises at least one standard deviation [SD] in the level of said VOC or SVOC in the samples of a negative control population. More preferably, the levels of VOCs or SVOCs in test samples are at least 2[SD] or 3[SD] larger or smaller than their mean level in samples of a negative control population. Accordingly, individual samples (of unknown status) are considered to belong to a sick population when the level of VOCs or SVOCs is at least 1[SD], 2[SD] or 3[SD] larger or smaller than the mean level of said VOCs or SVOCs in the samples of a negative control population.

In particular embodiments, the levels of a plurality of VOCs or SVOCs in the test sample form a pattern which is significantly different from the pattern of said VOCs or SVOCs in the control sample. According to further embodiments, the pattern is significantly different from a predetermined pattern of occurrence of said skin-emitted or excreted VOCs or SVOCs. The pattern can be analyzed with a learning and pattern recognition algorithm, as described hereinabove.

The test sample and or the control sample can be further compared with a sample comprising VOCS and SVOCs present in the environment of the subject to eliminate the effect of said environmental VOCs or SVOCs on the test sample.

Tuberculosis Diagnosing and Treatment

The methods of the invention are directed to diagnosing tuberculosis in a subject. In various embodiments, the subject is selected from a subject who is at risk of developing tuberculosis, a subject who is suspected of having tuberculosis, and a subject who is afflicted with tuberculosis. Each possibility represents a separate embodiment of the invention. In certain embodiments, said tuberculosis is pulmonary tuberculosis.

In some embodiments the tuberculosis is tuberculosis caused by *M. tuberculosis* bacteria. The subject being at risk of developing tuberculosis can be a subject living in the area of widespread environmental contamination by *M. tuberculosis* bacteria.

In some embodiments diagnosing tuberculosis is performed even in the presence of at least one confounding factor selected from smoking, HIV infection, consumption of medication, and combinations thereof. In some embodiments diagnosing tuberculosis is performed even in the presence of HIV infection.

In some embodiments the diagnosing methods according to various aspects and embodiments of the invention further comprise treating the subject if tuberculosis is diagnosed. In some embodiments the treating the subject comprises giving an anti-tuberculosis drug to the subject. In some embodiments the anti-tuberculosis drug is selected from rifampicin, isoniazid, ethambutol, pyrazinamide isonicotinic acid hydrazide and combinations thereof. Each possibility represents a separate embodiment of the invention.

As used herein and in the appended claims the singular forms "a", "an," and "the" include plural references unless the content clearly dictates otherwise. Thus, for example, reference to "a pattern recognition algorithm" includes a plurality of such algorithms and equivalents thereof known to those skilled in the art, and so forth.

The terms "coated", "capped" and "functionalized are used herein interchangeably.

The terms "non-real time" and "off-line" are used herein interchangeably.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Detection of Tuberculosis by a Direct Contact of an Absorbent Material on a Human Skin (Off-Line Method).

An analytical evaluation of compounds excreted from humans' skin was first performed by placing an absorbent material on a human skin and analyzing its contents using off-line methods: (a) Gas-Chromatography linked with Mass Spectrometry (GC-MS), and (b) an array of sensors based on nanomaterials.

Polydimethylsiloxane (PDMS) was used as an absorbent material. It was cleaned prior the sampling using a solution of 5% Decon 90 decontaminant in distilled water (18.2 Me), stored in a vacuum oven at 200° C. for at least 15 hours (see Riazanskaia et al. 2008, Analyst 133, 1020-1027) followed by thermal conditioning at 270° C. under a constant pure Nitrogen gas flow for 120 minutes. Tenax TA was also used as absorbing material. 20/35 meshed Tenax underwent thermal conditioning at 300° C. under a constant pure Nitrogen gas flow for 180 minutes and stored inside polyester meshed envelopes, which were cleaned in advance with a solution of 5% Decon 90 decontaminant in distilled water (18.2 Me). Thereafter, the Tenax was stored in a vacuum oven at 100° C. for at least 15 hours.

The absorbent material was placed on a volunteer's skin after a preforming a cleaning process of the designated skin area with sterile alcohol.

In the experiments the absorbent material was covered with an aluminum foil. The cover material was covered with a medical adhesive tape. Duration of the sampling was one hour. The samples of the volunteer skin's excretions in either PDMS or Tenax were stored in closed vials, wrapped with Parafilm in refrigerator at 2-8° C. before the analyses.

An analytical evaluation of the compounds adsorbed in the PDMS or Tenax was performed by GC/MS-QP2010 instrument (Shimadzu Corporation). GC/MS was equipped with a SLB-5 ms capillary column (with 5% phenyl methyl siloxane; 30 meter length; 0.25 mm internal diameter; 0.5 mm thicknesses; from Sigma-Aldrich), and was combined with a thermal desorption (TD) system (TD20; Shimadzu Corporation). The following oven temperature profile was set: (a) 6 min at 40° C.; (b) 13° C./min ramp until 170° C.; (c) 2 min at 170° C. (d) 6° C./min ramp until 300° C.; and (e) 15 min at 300° C.

The GC-MS and PT-MS profiles of Volatile Organic Compounds (VOCs) and semi-Volatile Organic Compounds (semi-VOCs) were compared to National Institute of Standards and Technology ("NIST") main library and analyzed by ANOVA, Wilcoxon and Student's t-test.

Two studies were conducted for investigation of the proposed approach for detection of active TB by detection of unique patterns of VOCs which emitted directly from human skin. The first study was conducted in in Cape Town, South Africa and the other in New Delhi, India. The volunteers' skin was sampled at several different body locations (chest area and inner arm area) by off-line methods using absorbing materials as described above (Tenax and PDMS). The samples were transferred to examination in the Technion, Israel, for the MS and nano-sensor array analyses. The complete South African study included 196 volunteers including 92 subjects afflicted with active TB and 104 non-TB and healthy subjects. Some of the South African clinical study designs presented hereinbelow included two group with 66 participants within each group: Group A included 10 patients with active TB; and Group B: 56 TB suspected volunteers, which present clinical symptoms yet with negative microbiological test results. The complete Indian study included 286 volunteers including 90 subjects afflicted with active TB and 196 non-TB and healthy subjects. Some of the Indian clinical study designs presented hereinbelow included three groups: Group C included 27 patients with active TB; Group D included 12 TB suspected volunteers, which present clinical symptoms yet with negative microbiological test results; and Group E included 12 healthy control volunteers. The clinical classification refers to two gold standards currently available: sputum culture and GexeXpert. All the participants in the study were screened for HIV and QFT-TB (QuantiFERON-TB Gold) test in order to further evaluated the effect of this potential confounding factors.

The sensitivity (True Positive/True positive+False negative), specificity (True Negative/True Negative+False Positive), accuracy (True Positive+True Negative/n), Positive Predictive Value (PPV=True positive/True positive+False Positive) and Negative Predictive Value (NPV=True Negative/True Negative+False Negative) of each test were calculated, evaluating the discriminative power of the diagnostic model.

Nano-Sensor Array Analysis

A stainless steel cell for the exposure contained the Gold NanoParticle (GNP)-based sensors mounted upon a customized polytetrafluoroethylene (PTFE) circuit. To transfer the VOCs trapped upon the absorption materials, the samples were thermally desorbed at 270° C. in an auto-sampler desorption system (TD20; Shimadzu Corporation, Japan). The desorbed samples were temporarily stored in a stainless steel column at 150° C. In parallel, the chamber containing the sensors was kept under vacuum conditions (~30 mTor) until the sample had been directed into the chamber. The remaining volume was filled with pure $N_2$ until reaching atmospheric pressure. A Keithley data logger device (model 2701 DMM) was used to sequentially acquire resistance readings from the sensor array for 5 min in vacuum prior to exposure (taken as baseline) followed by 5 min of sample that filled the chamber, followed by another 5 min of sensors recovery starting with chamber vacuum. The whole system was controlled by a custom-made LabView program. To supervise the sensor's functionality during the experiment, and to overcome sensor response drift, a fixed calibration gas mixture containing 11.5 ppm isopropyl alcohol, 2.8 ppm trimethylbenzene and 0.6 ppm 2-ethylhexanol was exposed to the sensors on a daily basis.

Linear Discriminant Function Analysis (DFA) models with Leave-one-out validation based on the normalized (according to the daily calibration) extracted features from responses of sensor-based nanoarray were built by using DFA algorithm with Matlab software for gaining the highest accuracy of the classification. For each tested binary comparison, more than one combination of sensors had the same accuracy rate. Each of this combinations owns different sensitivity and specificity, therefore, the choice of the desired model can be tailored-up according to the specifications: higher sensitivity or higher specificity (with the same accuracy). The models which are presented here are only an example for each binary discrimination with the highest accuracy and sensitivity. Other models had the same accuracy with lower sensitivity and higher specificity. P-value for each model's canonical values were calculated based on non-parametric method Wilcoxon and were lower than 0.05.

Preparation of Gold Nanoparticle Sensors

Gold nanoparticles coated with organic layers can be synthesized using the two-phase Brust method (Brust et al. 2002, Colloids and Surfaces A, 202, 175-186; Brust et al. 1994, Journal of the Chemical Society, Chemical Communications, 801-802). $AuCl_4$ was transferred from aqueous $HAuCl_4 \cdot XH_2O$ solution (25 mL, 36.5 mM) to a toluene solution by phase-transfer reagent tetraoctylammonium bromide (TOAB; 80 mL, 34.3 mM). After stirring, the organic phase was isolate and an excess of the chosen thiol was added to the solution. In order to receive a monodispersed solution of Au NPs, the molar ratio of $HAuCl_4 \cdot XH_2O$ to thiol is varied between 1:1 and 1:10 depending on the type of thiol. After stirring for 10 min, an aqueous solution of reducing agent sodium borohydride ($NaBH_4$), in large excess (25 mL, 0.4 M) is added to the solution. The reaction occurred by stirring at room temperature for 3 hours, producing a dark-brown solution. After separating the solution from the aqueous phase, the resulting solution was subjected to solvent removal in a rotary evaporator at 40° C. and followed by addition ethanol to the dried solution. The samples were kept in freezer for several days until sedimentation of the particles and afterwards were transferred to a centrifuge at 400 rpm and a temperature of 4° C. for additional sedimentation of the particles. The resulting solution is subjected to solvent removal in a rotary evaporator. The NPs were purified from free thiol ligands by repeated extractions. The coated gold nanoparticles were prepared at a range of concentration between 1 mg/mL and 500 mg/mL.

The coated gold nanoparticles were then dispersed in either toluene or ethanol. Chemiresistive layers were formed by drop-casting the solution onto semi-circular microelectronic transducers, until a resistance of several MΩ was reached. The devices were dried for 2 hours at ambient temperatures and then baked overnight at 50° C. in a vacuum oven. The microelectronic transducers consisted of ten pairs of circular interdigitated (ID) gold electrodes on silicon with 300 nm thermal oxide (Silicon Quest International, Nevada, US). The outer diameter of the circular electrode area was 3 mm, and the gap between two adjacent electrodes and the width of each electrode, was 20 µm each.

Preparation of Sensors of Functionalized Single Walled Carbon Nanotubes

Sensors of functionalized single walled carbon nanotubes were formed by drop-casting a solution of SWCNTs (from ARRY International LTD, Germany; ~30% metallic, ~70% conducting, average diameter=1.5 nm, length=7 mm) in dimethylformamide (DMF, from Sigma Aldrich Ltd., >98% purity) onto the pre-prepared electrical transducers. The sensors were based on an electrically continuous random network of SWCNTs (U.S. Pat. Nos. 8,366,630; 8,481,324; the contents of each of which are hereby incorporated in their entirety). After the deposition, the device was slowly dried overnight under ambient conditions to enhance the self-assembly of the SWCNTs and to afford the evaporation of the solvent. The procedure was repeated until a resistance of 100 KΩ to 10 MΩ was obtained. The microelectronic transducer for the SWCNT sensor consisted of ten pairs of 4.5 mm wide, interdigitated Ti/Pd electrodes on silicon with two microns of thermal oxide (Silicon Quest International, Nevada, US). The gap between two adjacent electrodes was 100 µm. The SWCNT sensor was organically functionalized with a polycyclic Aromatic Hydrocarbon (PAH) derivative hexa-perihexabenzocoronene.

Preparation of the PDMS Absorbent Material

A. List of Equipment/Instruments:

Double distilled water (DDW) system: Barnstead™ Easypure™ II, USA. Model number: D7381, Serial number: 1286061117477.

Vacuum oven: DAIHAN Scientific, CO. LTD., WiseVen. Model number: WOV-30, Serial number: 04022041168006.

Cutting printer: Silhouette studio, Silhouette Cameo 2, Serial number: T409B011631. Printer accessories: Blade number: SILH-BLADE-3-3T, cutting mat: CUT-MAT-12-3T.

TC-20: Markes International Ltd., TC-20: Multi-tube conditioner and dry-purge unit, B. List of Materials:

PDMS sheets: Specialty Silicone Products, Inc. (SSP), SSP-M823-0.017: molded translucent ultra-thin silicone membrane, Size: 12"×12"" with thickness 0.017". Batch numbers: FE013, DF012. Israeli distributor: Mechanic Art. Decon 90: Decon Laboratories, Inc., Contran 70, catalog number: 1002.

C. Cutting PDMS

The PDMS sheet was placed on the cutting mat and was cut using the cutting printer. The PDMS cutting size was 1 cm×2.5 cm. Each PDMS sheet contains approximately 594 such strips.

D. PDMS Cleaning

The PDMS sheets were first cleaned using a DDW: Decon 90 solution in the ratio of 100 mL:5 mL. Thereafter the PDMS strips were washed again with DDW. The PDMS strips were placed inside glass vials, which were organize inside aluminum trays. The trays were placed inside the vacuum oven set to a temperature of 200° C. for 24 hours. Afterwards, the trays were covered with aluminum foils until they reached room temperature and then corked.

E. PDMS Conditioning

The PDMS strips were conditioned every month, and underwent GC-MS quality check. The conditioning parameters were: 25 PSI, 270° C. for 2 hr. A single strip out of every 50 strips was checked by GC-MS and then discarded.

Preparation of the Tenax Absorbent Material

A. List of Equipment/Instruments:

Double distilled water (DDW) system: Barnstead™ Easypure™ II, USA. Model number: D7381, Serial number: 1286061117477.

Vacuum oven: DAIHAN Scientific, CO. LTD., WiseVen. Model number: WOV-30, Serial number: 04022041168006

Cutting printer: Silhouette studio, Silhouette Cameo 2, Serial number: T409B011631. Printer accessories: Blade number: SILH-BLADE-3-3T, cutting mat: CUT-MAT-12-3T.

TC-20: Markes International Ltd., TC-20: Multi-tube conditioner and dry-purge

B. Cutting and Sealing PES Envelopes:

The PES was according to the size of the cutting mat using the cutting printer. The PES cutting size is 40.3 mm×65.11 mm. Each PES sheet can contain 28 bags. A heat sealer was used to seal two edges of each PES piece to form a shape of an envelope.

C. PES Cleaning:

The PES sheets were first cleaned using a DDW: Decon 90 solution in the ratio of 100 mL:5 mL. Thereafter the PDMS strips were washed again with DDW. The PDMS strips were placed inside glass vials, which were organize inside aluminum trays. The trays were placed inside the vacuum oven set to a temperature of 100° C. for 24 hours. Afterwards, the trays were covered with aluminum foils until they reached room temperature and then corked.

D. Tenax Weighing and Conditioning:

In a dry lab, 134 mg batches of Tenax were weight in a weighing dish with tolerance error of 2 mg and placed inside 8 ml glass vials. The vials were corked and stored at room temperature. The Tenax was conditioned every month, and underwent GC-MS quality check. The conditioning parameters were: 20 PSI, 300° C. for 3 hr. A single Tenax tube piece out of every 20 Tenax tubes was check by GC-MS and then discarded.

E. Organization of Tenax Inside PES Envelopes:

The Tenax was poured to the PES envelope carefully. The Tenax was arranged in the lower part of the envelope, and the upper edge of the envelope (the only part that is open) was sealed by a heating sealer at the maximum heat. Immediately thereafter the vial was closed with the Tenax filled envelope and sealed with parafilm.

Inclusion and Exclusion Criteria for the Clinical Studies.

Active TB patients:

Volunteers aged 18-85.

Clinical symptoms (at least two of the TB classic symptoms: cough for more than 2 weeks, loss of weight, a single recorded temp>38° C., night sweats, generalized fatigue, hemoptysis, chest pain or active lesions, such as leaking, cheese, voids, etc. in chest radiograph).

Positive microbiology (either a positive Gene Xpert MTB/RIF or/and culture [MGIT for M. tb]).

Newly untreated diagnosed patients.

Chest X-ray supports diagnosis of TB.

HIV test.

QFT test.

Non TB:

Volunteers aged 18-85.

Clinical symptoms Negative culture result.

Negative GeneXpert test result.

Chest x-rays do not support diagnosis of active TB.

HIV test.

QFT test.

No clinical symptoms at follow up of 8 weeks.

Healthy Control:

No clinical symptoms

Clinical follow-up of 8 weeks

HIV test

QFT test

No clinical symptoms on follow up

Example 1: Nano-Sensor Array Analysis—DFA Analysis of Samples from the Inner Arm Area, South Africa DFA analyses of PDMS samples from the inner arm area of the 66 volunteers in the South African study were made for discrimination between the skin samples of active TB subjects from samples of Non-TB subjects. The results were compared with clinical tuberculosis results. The DFA model was based on the following chemiresistors and their features:

1. diketopyrrolopyrrole-naphthalene copolymer (PDPP-TNT) chemiresistor—delta R middle feature.
2. tert-dodecanethiol-based GNPs chemiresistor—delta R peak feature.
3. diketopyrrolopyrrole-naphthalene copolymer (PDPP-TNT)—delta R peak feature.
4. 3-ethoxythiophenol-based GNPs chemiresistor—delta R peak feature.

The delta R features and areas under curve are chemiresistor characteristics extracted from the responses of the sensors towards the sample. For each sensor there are possible features. Delta R end feature, delta R peak feature and delta R middle feature refer to the resistance at the end, at the peak or at the middle of the exposure, respectively, minus the vacuum resistance prior to the exposure. The area under response feature refers to the area under the peak during the exposure.

The results are given in Table 1:

TABLE 1

| | | distinguishing between Active TB and non TB subjects (inner arm) | |
|---|---|---|---|
| | | VOC test | |
| | | Active TB | Non-TB |
| Clinical TB result | Active TB | 10 | 0 |
| | Non-TB | 9 | 47 |

As seen in Table 1, all ten samples extracted from active TB subjects were found positive for TB, while out of the 56 samples extracted from Non-TB volunteers, nine were found positive for TB and 47 were found negative. The test performance in terms of sensitivity, specificity, accuracy, positive and negative predictive values are 100%, 83.9%, 86.3%, 52.6% and 100% respectively. Confounding factors, such as smoking and HIV status were found to not affect the results.

It was found that additional sensor combinations yielded the same accuracy, in similar inner arm area DFA models:

Decanethiol-based GNPs chemiresistor (X04y07-G)—Area under response feature; diketopyrrolopyrrole-naphthalene copolymer (PDPP-TNT) chemiresistor—Area under response feature; diketopyrrolopyrrole-naphthalene copolymer (PDPP-TNT)—chemiresistor—delta R peak feature; dodecanethiol-based GNPs chemiresistor—delta R peak feature.

Diketopyrrolopyrrole-naphthalene copolymer (PDPP-TNT) chemiresistor—Area under response feature; diketopyrrolopyrrole-naphthalene copolymer (PDPP-TNT)—chemiresistor—delta R peak feature; 2-nitro-4-(trifluoromethyl)benzenethiol-based GNPs chemiresistor—area under response feature; 2-nitro-4-(trifluoromethyl)benzenethiol-based GNPs chemiresistor—delta R peak feature.

2-nitro-4-(trifluoromethyl)benzenethiol-based GNPs chemiresistor—delta R end feature; 3-ethoxythiophenol-based GNPs chemiresistor—area under response feature; 2-ethylhexanethiol-based GNPs chemiresistor—delta R end feature; 2-ethylhexanethiol-based GNPs chemiresistor—delta R peak feature.

2-ethylhexanethiol-based GNPs chemiresistor—delta R peak feature; dibutyl disulfide-based GNPs chemiresistor—delta R end feature; 3-ethoxythiophenol-based GNPs chemiresistor—area under response feature; 3-ethoxythiophenol-based GNPs chemiresistor—delta R end feature.

2-ethylhexanethiol-based GNPs chemiresistor—delta R peak feature; decanethiol-based GNPs chemiresistor—delta R middle feature, dibutyl disulfide-based GNPs chemiresistor—delta R end feature, 3-ethoxythiophenol-based GNPs chemiresistor—area under response feature.

3-ethoxythiophenol-based GNPs chemiresistor—area under response feature, dibutyl disulfide-based GNPs chemiresistor—delta R end feature, 2-nitro-4-(trifluoromethyl)benzenethiol-based GNPs chemiresistor—delta R middle feature; 2-ethylhexanethiol-GNPs chemiresistor—delta R peak feature.

Benzyl mercaptan-based GNPs chemiresistor—area under response feature; 3-ethoxythiophenol-based GNPs chemiresistor—delta R end feature; octadecanethiol-based GNPs chemiresistor—Delta R middle feature, 2-ethylhexanethiol-GNPs chemiresistor—delta R peak feature.

Random networks (RNs) of carbon nanotubes (CNTs) with crystal hexa-perihexabenzocoronene (HBC) with C12 chemiresistor (HBC—C12)—area under response feature; 2-naphthalenethiol-based GNPs chemiresistor—area under curve feature; diketopyrrolopyrrole-naphthalene copolymer (PDPP-TNT) chemiresistor—delta R middle feature; diketopyrrolopyrrole-naphthalene copolymer (PDPP-TNT)—chemiresistor—delta R peak feature.

Octadecanethiol-based GNPs chemiresistor—delta R middle feature; benzyl mercaptan-based GNPs chemiresistor—delta R middle feature; octadecanethiol-based GNPs chemiresistor—delta R peak feature; 2-ethylhexanethiol-GNPs chemiresistor—delta R peak.

Tert-dodecanethiol-based GNPs chemiresistor—area under response feature; benzyl mercaptan-based GNPs chemiresistor—area under response feature; random networks (RNs) of carbon nanotubes (CNTs) with crystal hexa-perihexabenzocoronene (HBC) with C12 chemiresistor (HBC—C12)—area under response feature; 2-ethylhexanethiol-GNPs chemiresistor—delta R peak feature.

Decanethiol-based GNPs chemiresistor—area under response feature, tert-dodecanethiol-based GNPs chemiresistor area under curve feature; 2-nitro-4-(trifluoromethyl)benzenethiol-based GNPs chemiresistor—delta R end feature; 2-ethylhexanethiol-GNPs chemiresistor—delta R peak feature.

Example 2: Nano-Sensor Array Analysis—DFA Analysis of Samples from the Chest Area DFA analyses of PDMS samples from the inner arm area of 65 volunteers were made for discrimination between the skin samples of active TB subjects from samples of Non-TB subjects. The results were compared with clinical tuberculosis results. The DFA model was based on the following chemiresistors and their features:

1. decanethiol-based GNPs chemiresistor—area under response feature
2. decanethiol-based GNPs chemiresistor—delta R end feature
3. decanethiol-based GNPs chemiresistor—delta R end feature
4. dodecanethiol-based GNPs chemiresistor—delta R middle feature The results are given in Table 2:

TABLE 2

| | | distinguishing between Active TB and non TB subjects (chest) | |
|---|---|---|---|
| | | VOC test | |
| | | Active TB | Non-TB |
| Clinical TB result | Active TB | 10 | 0 |
| | Non-TB | 7 | 48 |

As seen in Table 2, all ten samples extracted from active TB subjects' chests were found positive for TB, while out of the 55 samples extracted from Non-TB volunteers' chests, seven were found positive for TB and 48 were found negative. The test performance in terms of sensitivity, specificity, accuracy, positive and negative predictive values are 100%, 85.7%, 89.2%, 58.8% and 100% respectively. Confounding factors, such as smoking and HIV status were found to not affect the results.

It was found that additional sensor combinations yielded the same accuracy, in similar inner arm area tests:

Octadecanethiol-based GNPs chemiresistor—area under response feature; decanethiol-based GNPs chemiresistor—area under response feature; decanethiol-based GNPs chemiresistor—delta R middle feature; decanethiol-based GNPs chemiresistor—delta R end feature.

Octadecanethiol-based GNPs chemiresistor—delta R end feature; decanethiol-based GNPs chemiresistor—area under response feature; decanethiol-based GNPs chemiresistor—delta R middle feature; decanethiol-based GNPs chemiresistor—delta R end feature.

Decanethiol-based GNPs chemiresistor—area under response feature; decanethiol-based GNPs chemiresistor—delta R end feature; decanethiol-based GNPs chemiresistor (additional sensor in the array with the same chemistry)—area under response feature; decanethiol-based GNPs chemiresistor—delta R end feature.

Example 3: Nano-Sensor Array Analysis—DFA Analysis of Samples Among HIV Negative and QFT Positive Subjects, South Africa Example 3A: analysis of samples from the inner part of the arm—DFA analyses of PDMS samples from the inner arm area of 35 volunteers in the South African study were made for discrimination between the skin samples of active TB subjects from samples of Non-TB subjects. Among the 35 volunteers, which are HIV negative with QFT positive, five have active TB. The DFA model was based on the following chemiresistors and their features:

1. random networks (RNs) of carbon nanotubes (CNTs) with crystal hexa-perihexabenzocoronene (HBC) with C12 chemiresistor (HBC—C12)—area under response feature.
2. a composite of black carbon with poly(propylene-urethaneureaphenyl-disulfide) PPUU-2S mixed with poly(urethane-carboxyphenyl-disulfide) PUC-2S chemiresistor—area under response feature.
3. 2-ethylhexanethiol-based GNPs chemiresistor—delta R Peak feature.
4. diketopyrrolopyrrole-naphthalene copolymer (PDPP-TNT) chemiresistor—delta R peak feature.

The results are given in Table 3A:

TABLE 3A distinguishing between Active TB and non TB subjects (inner arm, HIV negative and QFT positive)

|  |  | VOC test | |
|---|---|---|---|
|  |  | Active TB | Non-TB |
| Clinical | Active TB | 5 | 0 |
| TB result | Non-TB | 2 | 28 |

QFT is a blood test that aids in the detection of *M. tuberculosis* infection. However, it occasionally also provides indication of general infections. Since there is an effect of the HIV status on the QFT results, the sub-analysis was divided according to the HIV status. The purpose of the sub-analysis among HIV negative was to ensure that the sensor array is able to discriminate between active pulmonary TB infection from a group of TB negatives that may be infected with latent TB and/or extra-pulmonary TB. As seen in Table 3A, all five samples extracted from active TB subjects were found positive for TB, while out of the 30 samples extracted from Non-TB volunteers, two were found positive for TB and 28 were found negative. The test performance in terms of sensitivity, specificity, accuracy, positive and negative predictive values are 100%, 93%, 94.2%, 71.4% and 100% respectively.

Therefore, this analysis provides an indication that active TB infection can be detected with high accuracy from latent TB and extra-pulmonary TB cases among HIV negative population through the VOC test from the inner arm area.

Example 3B: analysis of samples from the chest area— DFA analyses of PDMS samples from the chest area of 34 volunteers were made for discrimination between the skin samples of active TB subjects from samples of Non-TB subjects. Among the 34 volunteers, which are HIV negative with QFT positive, five have active TB. The DFA model was based on the following chemiresistors and their features:

1. 3-ethoxythiophenol-based GNPs chemiresistor—area under response feature
2. tert-dodecanethiol-based GNPs chemiresistor—delta R Peak feature
3. 4-chlorobenzenemethanethiol-based GNPs chemiresistor—delta R Peak feature The results are given in Table 3B:

TABLE 3B distinguishing between Active TB and non TB subjects (chest, HIV negative and QFT positive)

|  |  | VOC test | |
|---|---|---|---|
|  |  | Active TB | Non-TB |
| Clinical | Active TB | 5 | 0 |
| TB result | Non-TB | 4 | 25 |

As seen in Table 3B, all five samples extracted from active TB subjects were found positive for TB, while out of the 29 samples extracted from Non-TB volunteers, four were found positive for TB and 25 were found negative. The test performance in terms of sensitivity, specificity, accuracy, positive and negative predictive values are 100%, 86.2%, 88.2%, 55.5% and 100% respectively.

Therefore, this analysis provides an indication that active TB infection can be detected with high accuracy from latent TB and extra-pulmonary TB cases among HIV negative population through the VOC test from the chest area.

Example 4: Nano-Sensor Array Analysis—DFA Analysis of Samples Among HIV Negative Subjects, South Africa Example 4A: analysis of samples from the inner part of the arm—DFA analyses of PDMS samples from the inner arm area of 41 volunteers in the South African study were made for discrimination between the skin samples of active TB subjects from samples of Non-TB subjects. Among the 41 volunteers, which are HIV negative, six have active TB. The DFA model included the chemiresistors and features of Example 3A. The results are given in Table 4A:

TABLE 4A distinguishing between Active TB and non
TB subjects (inner arm, HIV negative)

| | | VOC test | |
|---|---|---|---|
| | | Active TB | Non-TB |
| Clinical | Active TB | 6 | 0 |
| TB result | Non-TB | 2 | 33 |

As seen in Table 4A, all six samples extracted from active TB subjects were found positive for TB, while out of the 35 samples extracted from Non-TB volunteers, two were found positive for TB and 33 were found negative. The test performance in terms of sensitivity, specificity, accuracy, positive and negative predictive values are 100%, 94.3%, 95.1%, 75% and 100% respectively. Therefore, there is an indication that the detection of tuberculosis through the VOC test is improved, when eliminating the HIV factor by using HIV negative subjects, and taking samples from in the inner arm.

Example 4B: analysis of samples from the chest area—DFA analyses of PDMS samples from the inner arm area of 40 volunteers were made for discrimination between the skin samples of active TB subjects from samples of Non-TB subjects. Among the 40 volunteers, which are HIV negative, six have active TB. The DFA model was based on the following chemiresistors and their features:
1. diketopyrrolopyrrole-naphthalene copolymer (PDPP-TNT) chemiresistor—area under response feature
2. decanethiol-based GNPs chemiresistor (X03y12-G)—delta R end feature
3. decanethiol-based GNPs chemiresistor (X04y10-G)—delta R peak feature
4. dibutyl disulfide-based GNPs chemiresistor—delta R peak feature The results are given in Table 4B:

TABLE 4B distinguishing between Active TB and non
TB subjects (chest, HIV negative)

| | | VOC test | |
|---|---|---|---|
| | | Active TB | Non-TB |
| Clinical | Active TB | 6 | 0 |
| TB result | Non-TB | 6 | 28 |

As seen in Table 4B, all six samples extracted from active TB subjects were found positive for TB, while out of the 34 samples extracted from Non-TB volunteers, six were found positive for TB and 28 were found negative. The test performance in terms of sensitivity, specificity, accuracy, positive and negative predictive values are 100%, 82.3%, 85%, 50% and 100% respectively.

Example 5: Nano-Sensor Array Analysis—Analysis of PDMS Samples Among HIV Positive and QFT Positive Subjects, South Africa Example 5A: analysis of samples from the inner part of the arm—analyses of PDMS samples from the inner arm area of eight volunteers in the South African study were made for discrimination between the skin samples of active TB subjects from samples of Non-TB subjects. Among the eight volunteers, which are HIV positive and QFT positive, two have active TB. The experimental model was based on one extracted feature of butanethiol-based GNPs chemiresistor—delta R end feature.

The results are given in Table 5A:

TABLE 5A distinguishing between Active TB and non
TB subjects (inner arm, HIV positive and QFT positive)

| | | VOC test | |
|---|---|---|---|
| | | Active TB | Non-TB |
| Clinical | Active TB | 2 | 0 |
| TB result | Non-TB | 0 | 6 |

As seen in Table 5A, the two samples extracted from active TB subjects were found positive for TB, and the six samples extracted from Non-TB volunteers, were found negative for TB. The test performance in terms of sensitivity, specificity, accuracy, positive and negative predictive values are 100%, 100%, 100%, 100% and 100% respectively.

Example 5B: analysis of samples from the chest area—analyses of PDMS samples from the chest area of eight volunteers were made for discrimination between the skin samples of active TB subjects from samples of Non-TB subjects. Among the eight volunteers, which are HIV positive and QFT positive, two have active TB. The experimental model was based only on one extracted feature of 2-ethylhexanethiol-based GNPs chemiresistor delta R end feature.

The results are given in Table 5B:

TABLE 5B distinguishing between active TB and non TB subjects
(chest, HIV positive and QFT positive)

| | | VOC test | |
|---|---|---|---|
| | | Active TB | Non-TB |
| Clinical | Active TB | 2 | 0 |
| TB result | Non-TB | 1 | 5 |

As seen in Table 5B, the two samples extracted from active TB subjects were found positive for TB, while out of the three samples extracted from Non-TB volunteers, one were found positive for TB and two were found negative. The test performance in terms of sensitivity, specificity, accuracy, positive and negative predictive values are 100%, 83.3%, 87.5%, 66.7% and 100% respectively.

Example 6: Nano-Sensor Array Analysis—DFA Analysis of Samples Among HIV Positive Subjects, South Africa Example 6A: analysis of samples from the inner part of the arm—DFA analyses of PDMS samples from the inner arm area of 25 volunteers in the South African study were made for discrimination between the skin samples of active TB subjects from samples of Non-TB subjects. Among the 25 volunteers, which are HIV positive, four have active TB. The DFA model was based on the following chemiresistors and their features:
1. random networks (RNs) of carbon nanotubes (CNTs) With crystal hexa-perihexabenzocoronene (HBC) with C12 chemiresistor (HBC—C12) chemiresistor—delta R end feature 2. Random networks (RNs) of carbon nanotubes (CNTs) With crystal hexa-perihexabenzocoronene (HBC) with C12 chemiresistor (HBC—C12) chemiresistor—delta R middle feature The results are given in Table 6A:

TABLE 6A distinguishing between Active TB and non TB subjects (inner arm, HIV positive)

| | | VOC test | |
|---|---|---|---|
| | | Active TB | Non-TB |
| Clinical TB result | Active TB | 4 | 0 |
| | Non-TB | 2 | 19 |

As seen in Table 6A, all four samples extracted from active TB subjects were found positive for TB, while out of the 21 samples extracted from Non-TB volunteers, two were found positive for TB and 19 were found negative. The test performance in terms of sensitivity, specificity, accuracy, positive and negative predictive values are 100%, 90%, 92%, 66.7% and 100% respectively.

Example 6B: analysis of samples from the chest area—DFA analyses of PDMS samples from the chest area of 25 volunteers were made for discrimination between the skin samples of active TB subjects from samples of Non-TB subjects. Among the 25 volunteers, which are HIV positive, four have active TB. The DFA model was based on the following chemiresistors and features:
1. Dibutyl Disulfide-based GNPs chemiresistor—delta R end feature
2. a composite of black carbon with poly(propylene-urethaneureaphenyl-disulfide) PPUU-25-delta R middle feature
3. 2-naphthalenethiol-based GNPs chemiresistor—delta R peak feature The results are given in Table 6B:

TABLE 6B distinguishing between Active TB and non TB subjects (chest, HIV negative)

| | | VOC test | |
|---|---|---|---|
| | | Active TB | Non-TB |
| Clinical TB result | Active TB | 4 | 0 |
| | Non-TB | 3 | 18 |

As seen in Table 6B, all four samples extracted from active TB subjects were found positive for TB, while out of the 21 samples extracted from Non-TB volunteers, three were found positive for TB and 18 were found negative. The test performance in terms of sensitivity, specificity, accuracy, positive and negative predictive values are 100%, 85.7%, 88%, 57.1% and 100% respectively.

Example 7: GC-MS Analysis, South African Study

GC-MS analysis of samples taken from the 66 volunteers of the South African study was conducted in parallel to the sensor-based test. PDMS and Tenax samples were taken through exposing the absorbing materials to the skin of the volunteers (chest and inner arm) during one hour. The samples were then analyzed by GC-MS.

GC-MS (GCMS-QP2010; Shimadzu Corporation, Japan), combined with a thermal desorption system (TD20; Shimadzu Corporation, Japan), was used for the chemical analysis of the skin samples. The following oven temperature profile was set: (a) 6 min at 40° C.; (b) 13° C./min ramp until 170° C.; (c) 2 min at 170° C. (d) 6° C./min ramp until 300° C.; and (e) 15 min at 300° C. An SLB-5 ms capillary column (Sigma Aldrich Ltd.) with 5% phenyl methyl siloxane (30 m length, 0.25 mm internal diameter, and 0.5 µm thickness) was employed.

GC-MS chromatograms were analyzed with GC-MS solutions version 2.53SU1 Postrun analysis program (Shimadzu Corporation) and OpenChrom program in conjugation with Matlab software designed especially towards this study. The area under peaks of potential VOCs, which appeared in at least 80% of all active TB samples, were compared with the area under peaks in non-TB samples as well as in room samples. Potential VOCs which presented p-values below 0.05 with Wilcoxon test for the comparison of Active TB and NON-TB, as well as for the binary comparison of Active TB and room samples were validated in both programs. At this stage, the molecular structures of the VOCs were determined tentatively by spectral library match. In the future, compounds that had statistically significant changes in the abundance of their ions will be further analyzed by measuring pure standards of the relevant chemicals. Five different potential VOCs were discovered during a comparison between Active TB patients and Non-TB patients. Bars=Std Err Mean.

Example 7A: GC-MS Analysis of 2-methylbutane

GC-MS analyses of Tenax samples from the chest area of 64 volunteers were made for discrimination between samples extracted from active TB subjects and samples extracted from Non-TB subjects. Control samples were also taken from the room in which the experiment was carried out. The results are given in FIG. 2 and in Table 7A, based on Postrun analysis program:

TABLE 7A

GC-MS abundance of 2-methylbutane from active TB and non TB subjects

| | Mean | Std Dev | Std Err Mean |
|---|---|---|---|
| Active | 148727.00 | 91091.00 | 28805.00 |
| Non-TB | 46584.00 | 76997.30 | 10478.00 |
| Room | 79766.00 | 77200.60 | 10316.00 |

Figure 2:
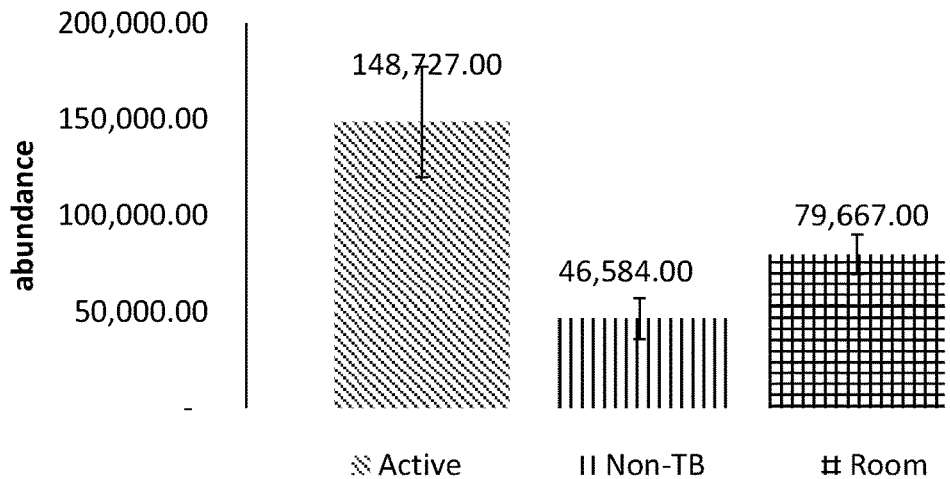
FIG. 2: Changes in abundance of 2-methylbutane acquired by GC-MS analysis of samples from the chest area of 64 TB-afflicted volunteers (diagonal bar), non-TB subjects (vertical bar) and room air control sample (grid bar). The columns and error bars represent the mean abundance and standard error of mean (SEM), respectively.

As seen from Table 7A and from FIG. 2, sample extracted from active TB subjects contain significantly more 2-methylbutane than samples derived from non TB subjects and room samples. According to Wilcoxon test, based on both GC-MS analyses, all the binary compressions between the three groups are significant with the p-value lower than 0.05. p-value to discriminate between Active and non TB subjects is 0.001. 2-methylbutane has not been reported as a TB-related VOC to date. Its higher production among active TB subjects may be associated with oxidative stress.

Tentative recognition according to their similarity index compared to a GC-MS search library, which includes the following compounds: 2-methylbutane; n-pentane; 2,4-dimethylpentane; 2,3-dimethylbutane; 3-methyl-2-pentanone; 1-chloro-2-methylpropane; oxalic acid, allyl hexyl ester; 2,6-dimethylheptane; 2-methylheptane; 2,2-dimethylbutane; n-heptane; 2-chloro-3-methylbutane; 1-chloro-2-methylpropane; and 2,5-dimethylhexane.

Example 7B: GC-MS Analysis of 2,2,4,6,6-pentamethylheptane

GC-MS analyses of Tenax samples from the chest area of 64 volunteers were made for discrimination between samples extracted from active TB subjects and samples extracted from Non-TB subjects and room samples. The results are given in FIG. 3 and in Table 7B, based on Postrun analysis program:

TABLE 7B

GC-MS abundance of 2,2,4,6,6-pentamethylheptane from active TB and non TB subjects

|  | Mean | Std Dev | Std Err Mean |
|---|---|---|---|
| Active | 149317.00 | 108745.00 | 34388.00 |
| Non-TB | 77084.00 | 69207.00 | 9418.00 |
| Room | 88317.00 | 60548.00 | 8091.00 |

Figure 3:
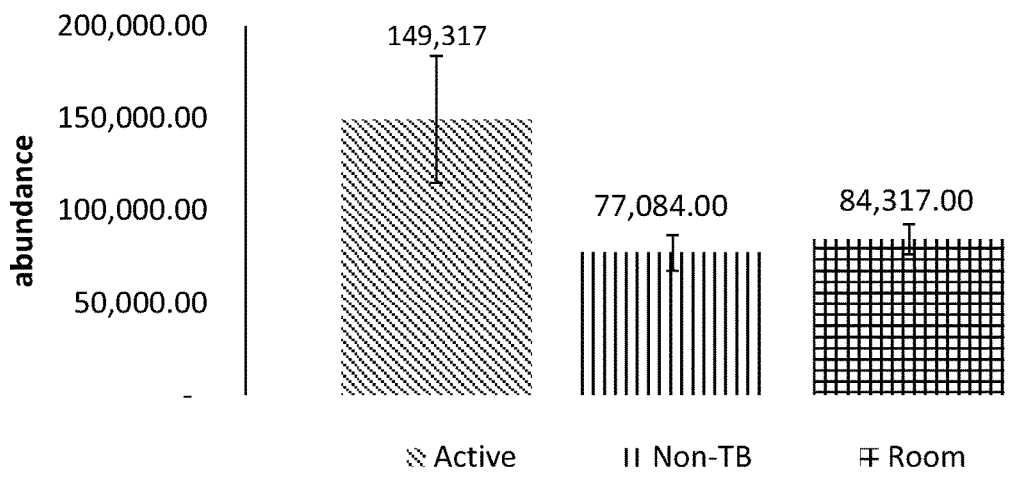
FIG. 3: Changes in abundance of 2,2,4,6,6-pentamethyl-heptane acquired by GC-MS analysis of samples from the chest area of 64 TB-afflicted volunteers (diagonal bar), non-TB subjects (vertical bar) and room air control sample (grid bar). The columns and error bars represent the mean abundance and standard error of mean (SEM), respectively.

As seen from Table 7B and from FIG. 3, sample extracted from active TB subjects contain significantly more 2,2,4,6,6-pentamethylheptane than samples derived from non TB subjects and room samples that serve as control samples. According to Wilcoxon test, based on both GC-MS analyses, all the binary compressions between the Active TB group and non-TB and room groups are significant with the p-values 0.0129 and 0.0461, respectively. This VOC was reported in the literature as an in—vitro tuberculosis marker (Phillips, Michael et al. Tuberculosis, Volume 87, Issue 1, 44-52), as a bacterial metabolite and as a oxidative stress product (Wood, William L., et al. Spectroscopy 21.6 (2006); Poli, Diana, et al. Respiratory research 6.1 (2005): 71; Phillips, Michael, et al. The Lancet 353.9168 (1999): 1930-1933). 2,2,4,6,6-pentamethylheptane has not been reported as a TB-related VOC to date.

Tentative recognition according to their similarity index compared to a GC-MS search library, which includes the following compounds: 2,2,4,6,6-pentamethylheptane; 2,2-dimethyldecane; 4-ethyl-2,2,6,6-tetramethylheptane; 2,2,4,6,6-pentamethylheptane; 2,2,9-trimethyldecane; 2,2-dimethylundecane; 2,2,5-trimethyldecane; 2,2,4-trimethylhexane; 2,2,8-trimethyldecane; 2,2,4-trimethyldecane; 2,2,6-trimethyloctane; 2,2-dimethyltetradecane; 2,2,5-trimethylhexane; 2,2,6-trimethyldecane; 2,2,7-trimethyldecane; 2,2,11,11-tetramethyldodecane; 2,2,4,4,6,8,8-heptamethylnonane; 2,2-dimethyloctane; 2,2,3-trim ethylnonane; and 2,2,4,4,6,8,8-heptamethylnonane.

Example 7C: GC-MS Analysis of Cyclopentane

GC-MS analyses of Tenax samples from the chest area of 64 volunteers were made for discrimination between samples extracted from active TB subjects and samples extracted from Non-TB subjects and room samples. The results are given in FIG. 4 and in Table 7C, based on Postrun analysis program:

TABLE 7C

GC-MS abundance of cyclopentane from active TB and non TB subjects

|  | Mean | Std Dev | Std Err Mean |
|---|---|---|---|
| Active | 1532077.00 | 608862.00 | 192539.00 |
| Non-TB | 1108082.00 | 644052.00 | 87644.00 |
| Room | 1172337.00 | 764570.00 | 102170.00 |

Figure 4:
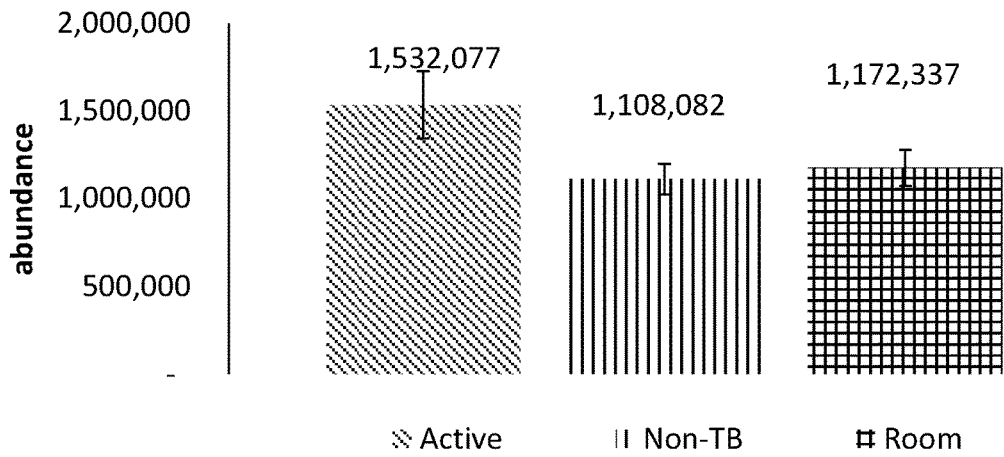
FIG. 4: Changes in abundance of cyclopentane acquired by GC-MS analysis of samples from the chest area of 64 TB-afflicted volunteers (diagonal bar), non-TB subjects (vertical bar) and room air control sample (grid bar). The columns and error bars represent the mean abundance and standard error of mean (SEM), respectively.

As seen from Table 7C and from FIG. 4 samples extracted from active TB subjects contain more cyclopentane than samples derived from non TB subjects and room samples that serve as control samples. According to Wilcoxon test, based on both GC-MS analyses, the binary compressions between the Active TB group and non-TB is significant with the p-values of 0.0312. Cyclopentane has not been reported as a TB-related VOC to date. Its higher production among active TB subjects may be associated with oxidative stress.

Tentative recognition according to their similarity index compared to a GC-MS search library, which includes the following compounds: cyclopentane; methylcyclobutane; 1-pentene; 1-methylcyclobutane; tetrahydro-6-methyl-2H-pyran-2-one; ethylcyclopropane; dihydro-2H-pyran-2,6(3H)-dione; dihydro-3-methyl-2,5-furandione; 7-methyl-1,4-dioxaspiro[2.4]heptan-5-one; cyclobutanone; tetrahydro-3-methyl-thiophene 1,1-dioxide; 6-methyl-1,4-dioxaspiro[2.4]heptan-5-one; carbonochloridic acid, pentyl ester; and 3,4-dimethylcyclopentanone.

Example 7D: GC-MS Analysis of Isopropyl Alcohol

GC-MS analyses of Tenax samples from the chest area of 64 volunteers were made for discrimination between samples extracted from active TB subjects and samples extracted from Non-TB subjects and room samples. The results are given in FIG. 5 and in Table 7D, based on Postrun analysis program:

TABLE 7D

GC-MS abundance of isopropyl alcohol from active TB and non TB subjects

|  | Mean | Std Dev | Std Err Mean |
|---|---|---|---|
| Active | 10339230.00 | 1768305.00 | 559187.00 |
| Non-TB | 13349122.00 | 3930888.00 | 534926.00 |
| Room | 13150879.00 | 4466031.00 | 596798.00 |

Figure 5:
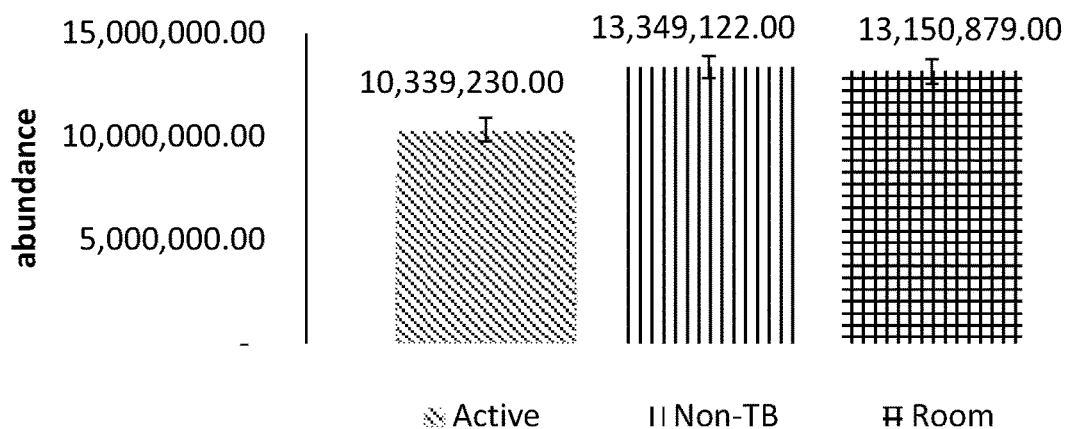
FIG. 5: Changes in abundance of isopropyl alcohol acquired by GC-MS analysis of samples from the chest area of 64 TB-afflicted volunteers (diagonal bar), non-TB subjects (vertical bar) and room air control sample (grid bar). The columns and error bars represent the mean abundance and standard error of mean (SEM), respectively.

As seen from Table 7D and from FIG. 5 samples extracted from active TB subjects contain less isopropyl alcohol than samples derived from non TB subjects and room samples that serve as control samples. According to Wilcoxon test, based on both GC-MS analyses, all the binary compressions between the Active TB group and non-TB and room groups are significant with the p-values 0.0064 and 0.0389, respectively.

Tentative recognition according to their similarity index compared to a GC-MS search library, which includes the following compounds: isopropyl alcohol; 2-pentanol; propylene glycol; (R)-(−)-3-methyl-2-butanol; 2-ethoxy-propane; (S)-(+)-2-pentanol; 2-hexanol; (+/−)-2-butanol; (S)-(+)-1,2-propanediol; R-(−)-1,2-propanediol; 4-penten-2-ol; (R)-2-hexanol; 3-methyl-2-pentanol; (S)-2-hexanol; 2-pentanol; 1-chloro-2-propanol; 1-methoxy-butane; and 1-bromo-2-propanol.

Example 7E: GC-MS Analysis of 2,3-dimethyl-2,3-butanediol

GC-MS analyses of PDMS samples from the inner arm area of 66 volunteers were made for discrimination between samples extracted from active TB subjects and samples extracted from Non-TB subjects and room samples. The results are given in FIG. 6 and in Table 7E, based on Postrun analysis program:

TABLE 7E

GC-MS abundance of 2,3-dimethyl-2,3-butanediol from active TB and non TB subjects

|  | Mean | Std Dev | Std Err Mean |
|---|---|---|---|
| Active | 20334.20 | 29059.90 | 9189.50 |
| Non-TB | 10295.20 | 19776.30 | 2642.70 |
| Room | 47.40 | 113.80 | 14.20 |

Figure 6:
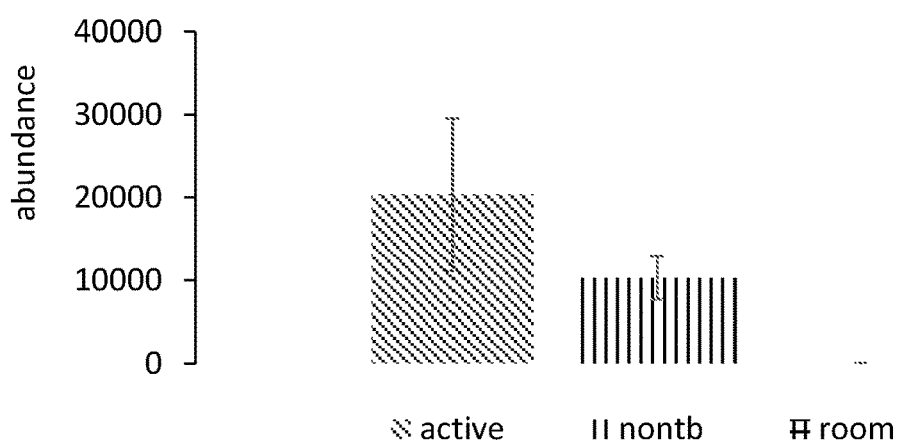
FIG. 6: Changes in abundance of 2,3-dimethyl-2,3-butanediol acquired by GC-MS analysis of samples from the inner arm area of 64 TB-afflicted volunteers (diagonal bar), non-TB subjects (vertical bar) and room air control sample (grid bar). The columns and error bars represent the mean abundance and standard error of mean (SEM), respectively.

As seen from Table 7E and from FIG. 6 samples extracted from active TB subjects contain more of 2,3-dimethyl-2,3-butanediol than samples derived from non TB subjects, whereas this molecule almost does not appear in room samples. This finding supports the endogenic source of this VOC. According to Wilcoxon test, based on both GC-MS analyses, all the binary compressions between the three groups are significant with the p-value lower than 0.05. p-value to discriminate between Active and non TB subjects is lower than 0.001. This potential material did not appear in the literature as skin VOC or TB-related VOC.

Tentative recognition according to their similarity index compared to a GC-MS search library, which includes the following compounds: 2,3-dimethyl-2,3-butanediol; 2,4-dimethyl-2-pentanol; 2,3-dimethyl-2-pentanol; 2-methyl-4-pentene-2-ol; 2-hydroxy-2-methylpropanoic acid, methyl ester; pentamethylethanol; 2-hexanol methyl ether; 2-isopropoxypropionic acid, methyl ester; 2,3-dimethyl-2-pentanol; 2,4-dimethyl-2-pentanol; 2,6-dimethyl-2-octanol; 2-methoxy-3-methylbutane; 2-hydroxy-2-methyl-propanoic acid, ethyl ester; 2-methyl-2-propanol; 2-decanol methyl ether; 3-ethyl-2-methyl-2-heptanol; 2-methyl-2-dodecanol; 1-(2-methoxypropoxy)-2-propanol; 2,3,3-trimethyl-2-pentanol; and 3-methylbutanamide.

Example 8: Nano-Sensor Array Analysis—DFA Analysis of PDMS Samples from the Inner Arm Area, India DFA analyses of PDMS samples from the inner arm area of the 51 volunteers in the Indian study were made for discrimination between (i) the skin samples of active TB subjects from samples of both healthy control and Non-TB volunteers and (ii) the skin samples of active TB subjects from samples of Non-TB subjects. The results were compared with clinical tuberculosis results.

Example 8A: For the discrimination of Active TB samples from both healthy controls and Non-TB samples, the DFA model was based on the following chemiresistors and their features:
1. Tert-dodecanethiol GNPs chemiresistor—area under response feature
2. decanethiol-based GNPs chemiresistor (X03y12-G)—delta R end feature
3. 3-ethoxythiophenol GNPs chemiresistor—delta R middle feature
4. random networks (RNs) of carbon nanotubes (CNTs) with crystal hexa-perihexabenzocoronene (HBC) with C12 chemiresistor (HBC—C12)—delta R end feature
5. a composite of black carbon with poly(propylene-urethaneureaphenyl-disulfide) PPUU-2S-area under response feature The results are given in Tables 8A:

TABLE 8A distinguishing between Active TB and healthy control and Non-TB group (inner arm)

|  |  | VOC test | |
|---|---|---|---|
|  |  | Active TB | Healthy and Non-TB |
| Clinical TB result | Active TB | 23 | 4 |
|  | Healthy and Non-TB | 4 | 20 |

As seen in Table 8A, out of the 27 samples extracted from active TB subjects, 23 were found positive for TB, while out of the 24 samples extracted from Non-TB and healthy control volunteers, 4 were found positive for TB and 20 were found negative. The test performance in terms of accuracy, sensitivity and specificity are 84.3%, 85% and 83% respectively. Confounding factors, such as smoking and HIV status were found to not affect the results.

Example 8B: For the discrimination of Active TB samples from Non-TB samples, the DFA model was based on the following chemiresistors and their features:
1. a composite of black carbon with poly(propylene-urethaneureaphenyl-disulfide) PPUU-2S-delta R middle feature
2. Tert-dodecanethiol GNPs chemiresistor—area under response feature
3. Tert-dodecanethiol GNPs chemiresistor—delta R end feature
4. a composite of black carbon with poly(propylene-urethaneureaphenyl-disulfide) PPUU-2S mixed with poly(urethane-carboxyphenyl-disulfide) PUC-2S chemiresistor—delta R peak feature The results are given in Tables 8B:

TABLE 8B distinguishing between Active TB and Non-TB (inner arm)

|  |  | VOC test | |
|---|---|---|---|
|  |  | Active TB | Non-TB |
| Clinical TB result | Active TB | 25 | 2 |
|  | Non-TB | 1 | 11 |

As seen in Table 8B, out of the 27 samples extracted from active TB subjects, 25 were found positive for TB, while out of the 12 samples extracted from Non-TB volunteers, 1 were found positive for TB and 11 were found negative. The test performance in terms of accuracy, sensitivity and specificity are 92.3%, 92.6% and 91.6% respectively. Confounding factor, smoking status, was found to not affect the results.

Example 9: Nano-Sensor Array Analysis—DFA Analysis of PDMS Samples from the Chest Area, India DFA analyses of PDMS samples from the chest area of the 49 volunteers in the Indian study were made for discrimination between (i) the skin samples of active TB subjects from samples of both healthy control and Non-TB volunteers and (ii) the skin samples of active TB subjects from samples of Non-TB subjects. The results were compared with clinical tuberculosis results.

Example 9A: For the discrimination of Active TB samples from both healthy controls and Non-TB samples, the DFA model was based on the following chemiresistors and their features:
1. a composite of black carbon with poly(propylene-urethaneureaphenyl-disulfide) PPUU-2S-delta R peak feature
2. Tert-dodecanethiol GNPs chemiresistor—area under response feature
3. 2-ethylhexanethiol GNPs chemiresistor—delta R middle feature
4. 1-Decanethiol GNPs chemiresistor—delta R middle feature
5. 3-ethoxythiophenol GNPs chemiresistor—delta R middle feature The results are given in Tables 9A:

TABLE 9A distinguishing between Active TB and Active TB and healthy control and Non-TB group (chest)

| | | VOC test | |
| --- | --- | --- | --- |
| | | Active TB | Healthy and Non-TB |
| Clinical TB result | Active TB | 23 | 3 |
| | Healthy and Non-TB | 2 | 21 |

As seen in Table 9A, out of the 26 samples extracted from active TB subjects, 23 were found positive for TB, while out of the 23 samples extracted from healthy controls and Non-TB volunteers, 2 were found positive for TB and 21 were found negative. The test performance in terms of accuracy, sensitivity and specificity are 89.7%, 88% and 91% respectively. Confounding factors, such as smoking and HIV status were found to not affect the results.

Example 9B: For the discrimination of Active TB samples from Non-TB samples, the DFA model was based on the following chemiresistors and their features:
1. a composite of black carbon with poly(propylene-urethaneureaphenyl-disulfide) PPUU-2S-delta R peak feature
2. 1-Decanethiol GNPs chemiresistor—delta R end feature
3. 1-Decanethiol GNPs chemiresistor—delta R peak feature
4. 4-chlorobenzene methane thiol GNPs chemiresistor—delta R middle feature The results are given in Tables 9B:

TABLE 9B distinguishing between Active TB and Non-TB (chest)

| | | VOC test | |
| --- | --- | --- | --- |
| | | Active TB | Non-TB |
| Clinical TB result | Active TB | 24 | 2 |
| | Non-TB | 1 | 10 |

As seen in Table 9B, out of the 26 samples extracted from active TB subjects, 24 were found positive for TB, while out of the 11 samples extracted from Non-TB volunteers, 1 were found positive for TB and 10 were found negative. The test performance in terms of accuracy, sensitivity and specificity are 91.9%, 92.3% and 90% respectively. Confounding factor, smoking status, was found to not affect the results.

It was found that additional sensor combinations yielded the same accuracy, in similar chest area DFA models:
Random networks (RNs) of carbon nanotubes (CNTs) with crystal hexa-perihexabenzocoronene (HBC) with C12 chemiresistor (HBC—C12)—area under response feature; 1-Decanethiol-delta R end feature; 2-naphtalenethiol-delta R end feature; decanethiol-based GNPs chemiresistor (X04y10-G)—delta R peak feature.
Decanethiol-based GNPs chemiresistor—delta R end feature; 3-ethoxythiophenolbased GNPs chemiresistor—delta R end feature; 3-ethoxythiophenol-based GNPs chemiresistor-delta R peak feature; random networks (RNs) of carbon nanotubes (CNTs) with crystal hexa-perihexabenzocoronene (HBC) with C12 chemiresistor (HBC—C12)—delta R peak feature.
Decanethiol-based GNPs chemiresistor—delta R end feature; random networks (RNs) of carbon nanotubes (CNTs) with crystal hexa-perihexabenzocoronene (HBC) with C12 chemiresistor (HBC—C12)—delta R peak feature; Hexanethiol-based GNPs chemiresistor-delta R middle feature; 3-ethoxythiophenol-based GNPs chemiresistor—delta R peak feature.
Random networks (RNs) of carbon nanotubes (CNTs) with crystal hexa-perihexabenzocoronene (HBC) with C12 chemiresistor (HBC—C12)—delta R peak feature; random networks (RNs) of carbon nanotubes (CNTs) with crystal hexa-perihexabenzocoronene (HBC) with C12 chemiresistor (HBC—C12)—delta R middle feature; decanethiol-based GNPs chemiresistor (X03y12-G)—delta R peak feature; decanethiol-based GNPs chemiresistor—delta R end feature.
A composite of black carbon with poly(propylene-urethaneureaphenyl-disulfide) PPUU-2S-delta R peak feature; 2-naphtalenethiol-based GNPs chemiresistor—delta R middle feature; decanethiol-based GNPs chemiresistor (X04y07-G)—delta R middle feature; decanethiol-based GNPs chemiresistor (X04y10-G)—delta R peak feature.
A composite of black carbon with poly(propylene-urethaneureaphenyl-disulfide) PPUU-2S-delta R peak feature; 2-naphtalenethiol-based GNPs chemiresistor—delta R middle feature; decanethiol-based GNPs chemiresistor—delta R middle feature; decanethiol-based GNPs chemiresistor (X03y12-G)—delta R peak feature. 2-naphtalenethiol-based GNPs chemiresistor—delta R peak feature; decanethiol-based GNPs chemiresistor (X08y08-G)—area under response feature; decanethiol-based GNPs chemiresistor—delta R peak feature; benzyl mercaptan-based GNPs chemiresistor—delta R peak feature.

Example 10: Nano-Sensor Array Analysis—DFA Analysis of Tenax Samples from the Inner Arm Area, India DFA analyses of Tenax samples from the inner arm area of the 28 volunteers in the Indian study were made for discrimination between (i) the skin samples of active TB subjects from samples of both healthy control and Non-TB volunteers and (ii) the skin samples of active TB subjects from samples of Non-TB subjects. The results were compared with clinical tuberculosis results.

Example 10A: For the discrimination of Active TB samples from both healthy controls and Non-TB samples, the DFA model was based on the following chemiresistors and their features:
1. 1-Decanethiol-based GNPs chemiresistor—area under response feature
2. 1-Decanethiol-based GNPs chemiresistor—delta R middle feature
3. 2-nitro-4-(trifluoromethyl)benzenethiol GNPs chemiresistor—delta R peak feature The results are given in Tables 10A:

TABLE 10A distinguishing between Active TB and healthy control and Non-TB group (inner arm)

| | | VOC test | |
|---|---|---|---|
| | | Active TB | Healthy and Non-TB |
| Clinical TB result | Active TB | 12 | 1 |
| | Healthy and Non-TB | 1 | 14 |

As seen in Table 10A, out of the 13 samples extracted from active TB subjects, 12 were found positive for TB, while out of the 15 samples extracted from Non-TB and healthy control volunteers, 1 was found positive for TB and 14 were found negative. The test performance in terms of accuracy, sensitivity and specificity are 92.85%, 92% and 93% respectively.

Example 10B: For the discrimination of Active TB samples from Non-TB samples, the DFA model was based on the following chemiresistors and their features:
1. Hexanethiol-based GNPs chemiresistor—delta R end feature
2. Hexanethiol-based GNPs chemiresistor—delta R peak feature The results are given in Table 10B:

TABLE 10B distinguishing between Active TB and Non-TB (inner arm)

| | | VOC test | |
|---|---|---|---|
| | | Active TB | Non-TB |
| Clinical TB result | Active TB | 12 | 1 |
| | Non-TB | 0 | 5 |

As seen in Table 10B, out of the 18 samples extracted from active TB subjects, 12 were found positive for TB, while out of the 5 samples extracted from Non-TB volunteers, all the samples were found negative. The test performance in terms of accuracy, sensitivity and specificity are 94.4%, 91.6% and 100% respectively.

It was found that additional sensor combination yielded the same accuracy, in similar chest area DFA models:
Hexanethiol-based GNPs chemiresistor—delta R peak feature; 3-ethoxythiophenol-based GNPs chemiresistor—delta R end feature.

Example 11: Nano-Sensor Array Analysis—DFA Analysis of Tenax Samples from the Chest, India DFA analyses of Tenax samples from the chest area of the 26 volunteers in the Indian study were made for discrimination between (i) the skin samples of active TB subjects from samples of both healthy control and Non-TB volunteers and (ii) the skin samples of active TB subjects from samples of Non-TB subjects. The results were compared with clinical tuberculosis results.

Example 11A: For the discrimination of Active TB samples from both healthy controls and Non-TB samples, the DFA model was based on the following chemiresistors and their features:
1. 1-Decanethiol-based GNPs chemiresistor—delta R peak feature
2. 3-ethoxythiophenol-based GNPs chemiresistor—area under response feature
3. diketopyrrolopyrrole-naphthalene copolymer (PDPP-TNT) chemiresistor—delta R peak feature The results are given in Tables 11A:

TABLE 11A distinguishing between Active TB and healthy control and Non-TB group (chest)

| | | VOC test | |
|---|---|---|---|
| | | Active TB | Healthy and Non-TB |
| Clinical TB result | Active TB | 11 | 1 |
| | Healthy and Non-TB | 1 | 13 |

As seen in Table 11A, out of the 12 samples extracted from active TB subjects, 11 were found positive for TB, while out of the 14 samples extracted from Non-TB and healthy control volunteers, 1 was found positive for TB and 13 were found negative. The test performance in terms of accuracy, sensitivity and specificity are 92.3%, 91.7% and 92.9% respectively.

It was found that additional sensor combination yielded the same accuracy, in similar chest area DFA models:
Diketopyrrolopyrrole-naphthalene copolymer (PDPP-TNT) chemiresistor delta R peak feature; 3-ethoxythiophenol-based GNPs chemiresistor—delta R peak feature; 1-Decanethiol-based GNPs (x04Y10-G) chemiresistor—area under response feature.
Diketopyrrolopyrrole-naphthalene copolymer (PDPP-TNT) chemiresistor delta R peak feature; 1-Decanethiol-based GNPs (x05Y14-G) chemiresistor—delta R peak feature; 3-ethoxythiophenol-based GNPs chemiresistor—area under response feature.
Diketopyrrolopyrrole-naphthalene copolymer (PDPP-TNT) chemiresistor delta R peak feature; 1-Decanethiol-based GNPs (x05Y14-G) chemiresistor—delta R peak feature; Hexanethiol-based GNPs chemiresistor—area under response feature.
Diketopyrrolopyrrole-naphthalene copolymer (PDPP-TNT) chemiresistor delta R peak feature; 3-ethoxythiophenol-based GNPs chemiresistor—delta R peak feature; Hexanethiol-based GNPs chemiresistor—area under response feature.
Diketopyrrolopyrrole-naphthalene copolymer (PDPP-TNT) chemiresistor delta R peak feature; a composite of black carbon with poly(propylene-urethaneureaphenyl-disulfide) PPUU-2S-delta R peak feature; a composite of black carbon with poly(propylene-urethaneureaphenyl-disulfide) PPUU-2S-area under response feature.
Diketopyrrolopyrrole-naphthalene copolymer (PDPP-TNT) chemiresistor delta R peak feature; a composite of black carbon with poly(propylene-urethaneureaphenyl-disulfide) PPUU-2S-delta R peak feature; dodecanethiol-based GNPs chemiresistor—area under response feature.

Diketopyrrolopyrrole-naphthalene copolymer (PDPP-TNT) chemiresistor—delta R peak feature; 1-Decanethiol-based GNPs (x04Y10-G) chemiresistor—delta R end feature; 3-ethoxythiophenol-based GNPs chemiresistor—delta R middle feature.

Diketopyrrolopyrrole-naphthalene copolymer (PDPP-TNT) chemiresistor—delta R peak feature; 1-Decanethiol-based GNPs (x04Y10-G) chemiresistor—delta R end feature; 1-Decanethiol-based GNPs (x05Y14-G) chemiresistor—delta R peak feature.

Diketopyrrolopyrrole-naphthalene copolymer (PDPP-TNT) chemiresistor—delta R peak feature; 1-Decanethiol-based GNPs (x04Y10-G) chemiresistor—delta R end feature; 3-ethoxythiophenol-based GNPs chemiresistor—delta R peak feature.

Diketopyrrolopyrrole-naphthalene copolymer (PDPP-TNT) chemiresistor—delta R peak feature; 3-ethoxythiophenol-based GNPs chemiresistor—delta R end feature; 3-ethoxythiophenol-based GNPs chemiresistor—delta R peak feature.

3-ethoxythiophenol-based GNPs chemiresistor—delta R peak feature; Octadecanethiol-based GNPs chemiresistor—delta R middle feature; 1-Decanethiol-based GNPs (x04Y07-G) chemiresistor—delta R middle feature.

Diketopyrrolopyrrole-naphthalene copolymer (PDPP-TNT) chemiresistor delta R peak feature; 3-ethoxythiophenol-based GNPs chemiresistor—delta R peak feature; 3-ethoxythiophenol-based GNPs chemiresistor—delta R middle feature.

Diketopyrrolopyrrole-naphthalene copolymer (PDPP-TNT) chemiresistor delta R peak feature; 3-ethoxythiophenol-based GNPs chemiresistor—delta R peak feature; 2-naphtalenethiol-based GNPs chemiresistor—delta R middle feature.

Example 11B: For the discrimination of Active TB samples from Non-TB samples, the DFA model was based on the following chemiresistors and their features:
1. diketopyrrolopyrrole-naphthalene copolymer (PDPP-TNT) chemiresistor—delta R peak feature
2. 3-ethoxythiophenol-based GNPs chemiresistor—area under response feature The results are given in Table 11B:

TABLE 11B

| distinguishing between Active TB and Non-TB (chest) | | |
|---|---|---|
| | VOC test | |
| | Active TB | Non-TB |
| Clinical TB result | Active TB | 11 | 1 |
| | Non-TB | 1 | 4 |

As seen in Table 11B, out of the 12 samples extracted from active TB subjects, 11 were found positive for TB, while out of the 5 samples extracted from Non-TB volunteers, 1 was found positive for TB and 4 were found negative. The test performance in terms of accuracy, sensitivity and specificity are 88.2%, 91% and 80% respectively.

It was found that additional sensor combination yielded the same accuracy, in similar chest area DFA models:

Diketopyrrolopyrrole-naphthalene copolymer (PDPP-TNT) chemiresistor—area under response feature; diketopyrrolopyrrole-naphthalene copolymer (PDPP-TNT) chemiresistor—delta R middle feature.

Diketopyrrolopyrrole-naphthalene copolymer (PDPP-TNT) chemiresistor delta R peak feature; 3-ethoxythiophenol-based GNPs chemiresistor—delta R end feature.

Diketopyrrolopyrrole-naphthalene copolymer (PDPP-TNT) chemiresistor—area under response feature; diketopyrrolopyrrole-naphthalene copolymer (PDPP-TNT) chemiresistor—delta R middle feature; random networks (RNs) of carbon nanotubes (CNTs) with crystal hexa-perihexabenzocoronene (HBC) with C12 chemiresistor (HBC—C12)—delta R middle feature.

Example 12: Nano-Sensor Array Analysis—DFA Analysis of Samples from the Inner Arm Area Among QFT Positive Volunteers, India Example 12A: DFA analyses of PDMS samples from the inner arm area of the 36 volunteers with positive QFT test result in the Indian study were made for discrimination between the skin samples of active TB subjects from samples of both healthy control and Non-TB volunteers.

For the discrimination of Active TB samples from both healthy controls and Non-TB samples, the DFA model was based on the following chemiresistors and their features:
1. diketopyrrolopyrrole-naphthalene copolymer (PDPP-TNT) chemiresistor—area under response feature.
2. Octadecanethiol-based GNPs chemiresistor—delta R peak feature.
3. 3-ethoxythiophenol-based GNPs chemiresistor—delta R peak feature.
4. Dibutyl disulfide-based GNPs chemiresistor—delta R peak feature.

The results are given in Table 12A:

TABLE 12A

| distinguishing between Active TB and heathy and Non-TB among QFT positive volunteers (arm) | | | |
|---|---|---|---|
| | | VOC test | |
| | | Active TB | Healthy and Non-TB with positive QFT result |
| Clinical TB result | Active TB | 19 | 3 |
| | Healthy and Non-TB with positive QFT result | 3 | 11 |

As seen in Table 12A, out of the 22 samples extracted from active TB subjects with positive QFT test result, 19 were found positive for TB, while out of the 14 samples extracted from healthy and Non-TB volunteers with positive QFT test result, 3 were found positive for TB and 11 were found negative. The test performance in terms of accuracy, sensitivity and specificity are 83.3%, 86% and 78% respectively.

It was found that additional sensor combination yielded the same accuracy, in similar chest area DFA models:

Diketopyrrolopyrrole-naphthalene copolymer (PDPP-TNT) chemiresistor—area under response feature; 1-Decanethiol-based GNPs (x04Y07-G) chemiresistor—delta R peak feature; 1-Decanethiol-based GNPs chemiresistor—delta R middle feature; 1-Decanethiol-based GNPs chemiresistor—area under response feature.

1-Decanethiol-based GNPs (x04Y07-G) chemiresistor—area under response feature; diketopyrrolopyrrole-naphthalene copolymer (PDPP-TNT) chemiresistor—area under response feature; 3-ethoxythiophenol-based GNPs chemiresistor—delta R peak feature; dodecanethiol-based GNPs chemiresistor—delta R peak feature.

3-ethoxythiophenol-based GNPs chemiresistor—delta R peak feature; dodecanethiol-based GNPs chemiresistor—delta R peak feature; diketopyrrolopyrrole-naphthalene copolymer (PDPP-TNT) chemiresistor—area under response feature; 1-Decanethiol-based GNPs (x04Y10-G) chemiresistor—area under response feature.

Tert-dodecanethiol-based GNPs chemiresistor—area under response feature; 1-Decanethiol-based GNPs (x04Y10-G) chemiresistor—delta R end feature; Tert-dodecanethiol-based GNPs chemiresistor—delta R middle feature; 1-Decanethiol-based GNPs (x08Y08-G) chemiresistor—delta R middle feature Diketopyrrolopyrrole-naphthalene copolymer (PDPP-TNT) chemiresistor—area under response feature; 1-Decanethiol-based GNPs (x02Y10-G) chemiresistor—area under response feature; Octadecanethiol-based GNPs chemiresistor—delta R peak feature; Hexanethiol-based GNPs chemiresistor—delta R peak feature.

Diketopyrrolopyrrole-naphthalene copolymer (PDPP-TNT) chemiresistor—area under response feature; 1-Decanethiol-based GNPs (x08Y08-G) chemiresistor—delta R middle feature; random networks (RNs) of carbon nanotubes (CNTs) with crystal hexa-perihexabenzocoronene (HBC) with C12 chemiresistor (HBC—C12)—area under response feature; a composite of black carbon with poly(propylene-urethaneurea-phenyl-disulfide) PPUU-2S-area under response feature.

Diketopyrrolopyrrole-naphthalene copolymer (PDPP-TNT) chemiresistor—area under response feature; random networks (RNs) of carbon nanotubes (CNTs) with crystal hexa-perihexabenzocoronene (HBC) with C12 chemiresistor (HBC—C12)—area under response feature; random networks (RNs) of carbon nanotubes (CNTs) with crystal hexa-perihexabenzocoronene (HBC) with C12 chemiresistor (HBC—C12)-delta R middle feature; Octadecanethiol-based GNPs chemiresistor—delta R peak feature.

Diketopyrrolopyrrole-naphthalene copolymer (PDPP-TNT) chemiresistor—area under response feature; a composite of black carbon with poly(propylene-urethaneureaphenyl-disulfide) PPUU-2S mixed with poly(urethane-carboxyphenyl-disulfide) PUC-2S chemiresistor—area under response feature; 1-Decanethiol-based GNPs chemiresistor—delta R end feature; diketopyrrolopyrrole-naphthalene copolymer (PDPP-TNT) chemiresistor—area under response feature; a composite of black carbon with poly(propylene-urethaneureaphenyl-disulfide) PPUU-2S mixed with poly(urethane-carboxyphenyl-disulfide) PUC-2S chemiresistor—delta R peak feature Diketopyrrolopyrrole-naphthalene copolymer (PDPP-TNT) chemiresistor—area under response feature; a composite of black carbon with poly(propylene-urethaneureaphenyl-disulfide) PPUU-2S mixed with poly(urethane-carboxyphenyl-disulfide) PUC-2S chemiresistor—area under response feature; random networks (RNs) of carbon nanotubes (CNTs) with crystal hexa-perihexabenzocoronene (HBC) with C12 chemiresistor (HBC—C12)—delta R middle feature; Hexanethiol-based GNPs chemiresistor—delta R peak feature.

Diketopyrrolopyrrole-naphthalene copolymer (PDPP-TNT) chemiresistor—area under response feature; Octadecanethiol-based GNPs chemiresistor—delta R end feature; Hexanethiol-based GNPs chemiresistor—delta R peak feature; Dibutyl disulfide-based GNPs chemiresistor—delta R peak feature.

Diketopyrrolopyrrole-naphthalene copolymer (PDPP-TNT) chemiresistor—area under response feature; 1-Decanethiol-based GNPs (x08Y08-G) chemiresistor—delta R end feature; Tert-dodecanethiol-based GNPs chemiresistor—delta R peak feature; a composite of black carbon with poly(propylene-urethaneurea-phenyl-disulfide) PPUU-2S mixed with poly(urethane-carboxyphenyl-disulfide) PUC-2S chemiresistor—delta R peak feature.

Diketopyrrolopyrrole-naphthalene copolymer (PDPP-TNT) chemiresistor—area under response feature; 1-Decanethiol-based GNPs (x08Y08-G) chemiresistor—delta R middle feature; 1-Decanethiol-based GNPs (x04Y10-G) chemiresistor—delta R end feature; 2-naphtalenethiol-based GNPs chemiresistor—delta R peak feature.

diketopyrrolopyrrole-naphthalene copolymer (PDPP-TNT) chemiresistor—area under response feature; 1-Decanethiol-based GNPs (x04Y10-G) chemiresistor—delta R end feature; Hexanethiol-based GNPs chemiresistor—delta R peak feature; Dibutyl disulfide-based GNPs chemiresistor—delta R peak feature.

Diketopyrrolopyrrole-naphthalene copolymer (PDPP-TNT) chemiresistor—area under response feature; Hexanethiol-based GNPs chemiresistor—delta R peak feature; 2-ethylhexanethiol-based GNPs chemiresistor—delta R end feature; dodecanethiol-based GNPs chemiresistor—delta R peak feature.

Diketopyrrolopyrrole-naphthalene copolymer (PDPP-TNT) chemiresistor—area under response feature; dodecanethiol-based GNPs chemiresistor—delta R end feature; Octadecanethiol-based GNPs chemiresistor—delta R peak feature; Hexanethiol-based GNPs chemiresistor—delta R peak feature.

Diketopyrrolopyrrole-naphthalene copolymer (PDPP-TNT) chemiresistor—area under response feature; Octadecanethiol-based GNPs chemiresistor—delta R peak feature; Hexanethiol-based GNPs chemiresistor—delta R peak feature; Octadecanethiol-based GNPs chemiresistor—delta R middle feature.

Diketopyrrolopyrrole-naphthalene copolymer (PDPP-TNT) chemiresistor—area under response feature; Octadecanethiol-based GNPs chemiresistor—delta R peak feature; Hexanethiol-based GNPs chemiresistor—delta R peak feature; 2-ethylhexanethiol-based GNPs chemiresistor—delta R middle feature.

Diketopyrrolopyrrole-naphthalene copolymer (PDPP-TNT) chemiresistor—area under response feature; dodecanethiol-based GNPs chemiresistor—delta R peak feature; Hexanethiol-based GNPs chemiresistor—delta R peak feature; 1-Decanethiol-based GNPs (x04Y10-G) chemiresistor—delta R middle feature.

Diketopyrrolopyrrole-naphthalene copolymer (PDPP-TNT) chemiresistor—area under response feature; Octadecanethiol-based GNPs chemiresistor—delta R peak feature; Hexanethiol-based GNPs chemiresistor—delta R peak feature; Dibutyl disulfide-based GNPs chemiresistor—delta R peak feature.

Diketopyrrolopyrrole-naphthalene copolymer (PDPP-TNT) chemiresistor—area under response feature; Hexanethiol-based GNPs chemiresistor—delta R peak feature; 1-Decanethiol-based GNPs (x02Y10-G) chemiresistor—delta R peak feature; dodecanethiol-based GNPs chemiresistor—delta R peak feature.

Diketopyrrolopyrrole-naphthalene copolymer (PDPP-TNT) chemiresistor—area under response feature; Hexanethiol-based GNPs chemiresistor—delta R peak feature; 1-Decanethiol-based GNPs (x08Y08-G) chemiresistor—delta R peak feature; dodecanethiol-based GNPs chemiresistor—delta R peak feature.

Hexanethiol-based GNPs chemiresistor—delta R peak feature; a composite of black carbon with poly(propylene-urethaneureaphenyl-disulfide) PPUU-2S-area under response feature; Dibutyl disulfide-based GNPs chemiresistor—delta R middle feature; 3-ethoxythiophenol-based GNPs chemiresistor—delta R peak feature.

A composite of black carbon with poly(propylene-urethaneureaphenyl-disulfide) PPUU-2S-delta R end feature; Tert-dodecanethiol-based GNPs chemiresistor—delta R middle feature; 3-ethoxythiophenol-based GNPs chemiresistor—delta R middle feature, 2-nitro-4-(trifluoromethyl)benzenethiol-based GNPs chemiresistor—delta R middle feature.

Example 12B: Additional DFA analyses was preformed based on Tenax samples from the inner arm area of the 19 volunteers with positive QFT test result in the Indian study were made for discrimination between the skin samples of active TB subjects from samples of both healthy control and Non-TB volunteers.

For the discrimination of Active TB samples from both healthy controls and Non-TB samples, the DFA model was based on the following chemiresistors and their features:
1. Dodecanethiol-based GNPs chemiresistor—area under response feature
2. 1-Decanethiol (X05Y14-G)-based GNPs chemiresistor—delta R end feature The results are given in Table 12B:

TABLE 12B distinguishing between Active TB and heathy and Non-TB among QFT positive (arm)

| | | VOC test | |
|---|---|---|---|
| | | Active TB | Healthy and Non-TB with positive QFT result |
| Clinical TB result | Active TB | 10 | 1 |
| | Healthy and Non-TB with positive QFT result | 2 | 6 |

As seen in Table 12B, out of the 11 samples extracted from active TB subjects with positive QFT test result, 10 were found positive for TB, while out of the 8 samples extracted from healthy and Non-TB volunteers with positive QFT test result, 2 were found positive for TB and 6 were found negative. The test performance in terms of accuracy, sensitivity and specificity are 84.2%, 90% and 75% respectively.

It was found that additional sensor combination yielded the same accuracy, in similar chest area DFA models:
Octadecanethiol-based GNPs chemiresistor—area under response feature; 1-Decanethiol (X05Y14-G)-based GNPs chemiresistor—delta R end feature.

Octadecanethiol-based GNPs chemiresistor—area under response feature; 1-Decanethiol (X04Y07-G)-based GNPs chemiresistor—delta R middle feature.

1-Decanethiol (X05Y14-G)-based GNPs chemiresistor—delta R end feature; 2-nitro-4-(trifluoromethyl)benzenethiol-based GNPs chemiresistor—area under response feature Example 13: Nano-Sensor Array Analysis—DFA Analysis of Samples from the Chest Area Among QFT Positive Volunteers, India Example 13A: DFA analyses of PDMS samples from the chest area of the 34 volunteers with positive QFT test result in the Indian study were made for discrimination between the skin samples of active TB subjects from samples of both healthy control and Non-TB volunteers.

For the discrimination of Active TB samples from both healthy controls and Non-TB samples, the DFA model was based on the following chemiresistors and their features:
1. 2-nitro-4-(trifluoromethyl)benzenethiol-based GNPs chemiresistor—area under response feature
2. 2-ethylhexanethiol-based GNPs chemiresistor—delta R end feature
3. 2-nitro-4-(trifluoromethyl)benzenethiol-based GNPs chemiresistor—delta R peak feature
4. random networks (RNs) of carbon nanotubes (CNTs) with crystal hexa-perihexabenzocoronene (HBC) with C12 chemiresistor (HBC—C12)—delta R peak feature The results are given in Table 13A:

TABLE 13A distinguishing between Active TB and heathy and Non-TB among QFT positive volunteers (chest)

| | | VOC test | |
|---|---|---|---|
| | | Active TB | Healthy and Non-TB with positive QFT result |
| Clinical TB result | Active TB | 20 | 1 |
| | Healthy and Non-TB with positive QFT result | 1 | 12 |

As seen in Table 13A, out of the 21 samples extracted from active TB subjects with positive QFT test result, 20 were found positive for TB, while out of the 13 samples extracted from healthy and Non-TB volunteers with positive QFT test result, 1 was found positive for TB and 12 were found negative. The test performance in terms of accuracy, sensitivity and specificity are 94.1%, 95% and 92% respectively. Smoking status was tested and had a negligible effect on the discrimination.

It was found that additional sensor combination yielded the same accuracy, in similar chest area DFA models:
2-nitro-4-(trifluoromethyl)benzenethiol-based GNPs chemiresistor—delta R peak feature; random networks (RNs) of carbon nanotubes (CNTs) with crystal hexa-perihexabenzocoronene (HBC) C) with C12 chemiresistor (HBC—C12)—delta R peak feature; 3-ethoxythiophenol-based GNPs chemiresistor—area under response feature; 1-Decanethiol-based GNPs chemiresistor—delta R middle feature.

Example 13B: Additional DFA analyses was preformed base on Tenax samples from the chest area of the 18 volunteers with positive QFT test result in the Indian study were made for discrimination between the skin samples of active TB subjects from samples of both healthy control and Non-TB volunteers.

For the discrimination of Active TB samples from both healthy controls and Non-TB samples, the DFA model was based on the following chemiresistors and their features:

1. 1-Decanethiol (X03Y12-G)-based GNPs chemiresistor—area under response feature.
2. Octadecanethiol)-based GNPs chemiresistor—delta R peak feature.

The results are given in Table 13B:

TABLE 13B distinguishing between Active TB and heathy and Non-TB among QFT positive (chest)

| | | VOC test | |
|---|---|---|---|
| | | Active TB | Healthy and Non-TB with positive QFT result |
| Clinical TB result | Active TB | 9 | 1 |
| | Healthy and Non-TB with positive QFT result | 0 | 8 |

As seen in Table 13B, out of the 10 samples extracted from active TB subjects with positive QFT test result, 9 were found positive for TB, while out of the 8 samples extracted from healthy and Non-TB volunteers with positive QFT test result, all were found negative. The test performance in terms of accuracy, sensitivity and specificity are 94.4%, 90% and 100% respectively.

Example 14: GC-MS Analysis, Indian Study

GC-MS analysis of samples taken from the 54 volunteers of the Indian study was conducted in parallel to the sensor-based test. PDMS and Tenax samples were taken through exposing the absorbing materials to the skin of the volunteers (chest and inner arm) during one hour. The samples were then analyzed by GC-MS under the same conditions mentioned in Example 7. The area under peaks of potential VOCs, which appeared in at least 70% of all active TB samples, were compared with the area under peaks in non-TB samples as well as in room samples. At this stage, the molecular structures of the VOCs were determined tentatively by spectral library match. In the future, compounds that had statistically significant changes in the abundance of their ions will be further analyzed by measuring pure standards of the relevant chemicals. Three different potential VOCs were discovered during a comparison between Active TB patients and both healthy and Non-TB volunteers. Bars=Std Err Mean.

Example 14A: GC-MS Analysis of Xylene

GC-MS analyses of Tenax samples from the inner arm area of 28 volunteers were made for discrimination between samples extracted from active TB subjects and samples extracted from both healthy and Non-TB subjects. Control samples were also taken from the room in which the experiment was carried out. The results are given in FIG. 7 and in Table 14A, based on Post run program analysis:

TABLE 14A

GC-MS abundance of xylene from active TB and both healthy and non TB subjects

| | Mean | Std Dev | Std Err Mean |
|---|---|---|---|
| Active | 34,190 | 17,715.2 | 5,114 |
| Healthy and Non-TB | 56,807 | 30,240.2 | 7,560 |
| Room | 100,172 | 79,584.2 | 12,583 |

Figure 7:
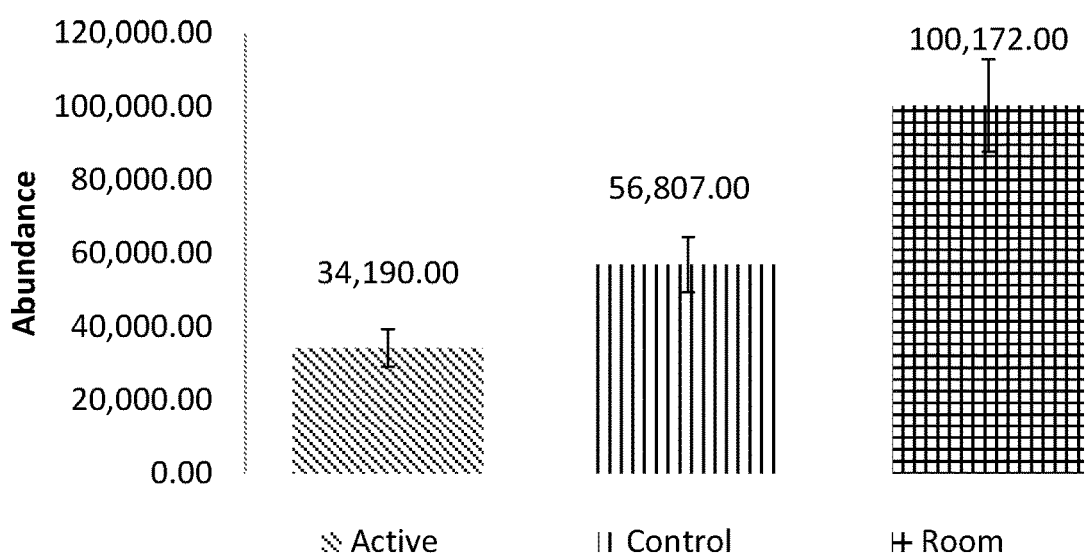
FIG. 7: Changes in abundance of xylene acquired by GC-MS analysis of samples from the inner arm area of 28 TB-afflicted volunteers (diagonal bar), non-TB subjects (vertical bar) and room air control sample (grid bar). The columns and error bars represent the mean abundance and standard error of mean (SEM), respectively.

As seen from Table 14A and from FIG. 7, sample extracted from active TB subjects contain significantly less xylene than samples derived from both healthy and non TB subjects and room samples. According to Wilcoxon test, based on both GC-MS analyses, all the binary compressions between the three groups are significant with the p-value lower than 0.05. Xylene has been reported as a TB-related VOC in urine; however with an opposite trend.

Its lower abundance among active TB subjects may be associated to unique pathways of *M. tuberculosis* involving ethylbenzene degradation/toluene and xylene degradation. Moreover, the highest abundance was obtained for the room samples, as expected due to pollutants.

Tentative recognition according to their similarity index compared to a GC-MS search library, which includes the following compounds: 5-(1-methylethylidene)-1,3-cyclopentadiene; ethylbenzene; 1,6-heptadiyne; 2,6-octadiyne; m-xylene; o-xylene; p-xylene; (nitromethyl)-benzene; 5-methyl-1,6-heptadien-3-yne; tricyclo[4.1.1.0(7,8)]oct-3-ene; (phenylmethoxy)-urea; 1,7-octadiyne; 1-ethenyl-3-methylene-cyclopentene.

Example 14B: GC-MS Analysis of Squalene

GC-MS analyses of Tenax samples from the inner arm area of 28 volunteers were made for discrimination between samples extracted from active TB subjects and samples extracted from both healthy and Non-TB subjects. Control samples were also taken from the room in which the experiment was carried out. The results are given in FIG. 8 and in Table 14B, based on Post run program analysis:

TABLE 14B

GC-MS abundance of squalene from active TB and both healthy and non TB subjects

| | Mean | Std Dev | Std Err Mean |
|---|---|---|---|
| Active | 52,394 | 62,443 | 18,026 |
| Healthy and Non-TB | 108,837 | 105,863 | 26,466 |
| Room | 46,824 | 277,103 | 43,814 |

Figure 8:
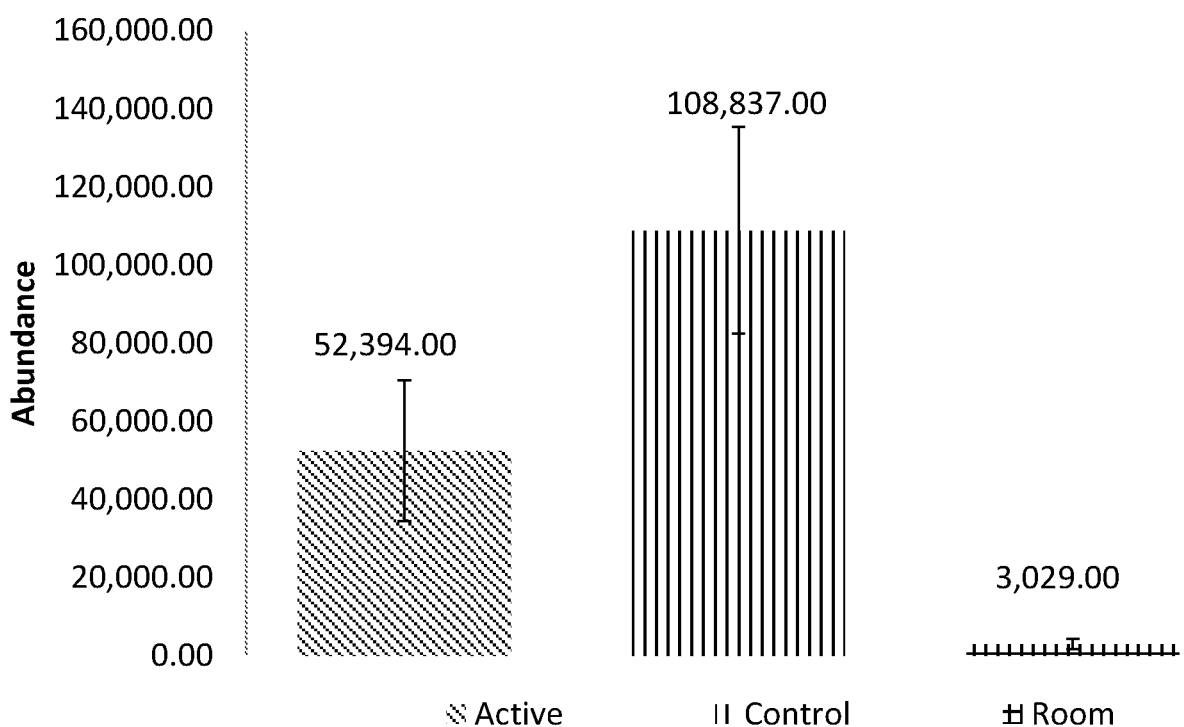
FIG. 8: Changes in abundance of squalene acquired by GC-MS analysis of samples from the inner arm area of 28 TB-afflicted volunteers (diagonal bar), non-TB subjects (vertical bar) and room air control sample (grid bar). The columns and error bars represent the mean abundance and standard error of mean (SEM), respectively.

As seen from Table 14B and from FIG. 8, sample extracted from active TB subjects contain significantly less squalene than samples derived from both healthy and non TB subjects and room samples. According to Wilcoxon test, all the binary compressions between the three groups are significant with the p-value lower than 0.05 with the analysis of OpenChrom program in conjugation with Matlab software designed especially towards this study. Post-run program analysis shows a p-value=0.0601 to discriminate between Active and both healthy and non TB subjects, as displayed in FIG. 8.

Squalene has not been reported as a TB-related VOC to date. For *M. tuberculosis*, the requirements of the cell membrane can be satisfied by either sterol surrogates, synthesized directly from squalene by an anaerobic pathway, or by sterols synthesized from squalene by an aerobic pathway. This may be associated with the lower abundance among active TB subjects. In addition, *M. tuberculosis* uses P450s to initiate breakdown of host cholesterol as an energy source.

Tentative recognition according to their similarity index compared to a GC-MS search library, which includes the following compounds: 5,9,13-trimethyl-4,8,12-tetradecatrienal; 1-(3,5-dinitrophenoxy)-3,7,11-trimethyl-dodeca-2,6,10-triene; 2,6,10-dodecatrien-1-ol, 3,7,11-trim ethyl-, (E,E)-; farnesol; 4,8,12-trim ethyl-3,7,11-tridecatrienenitrile; 5,9,13-trimethyl-4,8,12-tetradecatrienenitrile; 6,11-dimethyl-2,6,10-dodecatrien-1-ol; 1,5,9-undecatriene, 2,6,10-trimethyl-, (Z)-; 7,11-dimethyl dodeca-2,6,10-trien-1-ol; 2,6-dimethyl-1,5-heptadiene; farnesol isomer a; 2,6,10,14,18,22-tetracosahexaene, 2,6,10,15,19,23-hexamethyl (all-E)-; 2,6-octadiene, 4,5-dimethyl-; 2,6-octadiene, 1-bromo-3,7-dimethyl-; (E)-all-trans-3,7,11-Trimethyl-2,6,10-dodecatriene-1-aldoxime; 1,6-octadiene, 3,5-dimethyl-, trans-; 4,9,13,17-tetramethyl-4,8,12,16-octadecatetraenal; hexadeca-2,6,10,14-tetraen-1-ol, 3,7,11,16-tetramethyl-, (E,E,E)-; 1,5-heptadiene, 3,3,5-trimethyl-, 2,6-dimethyl-2,6-octadiene; (Z)-all-trans-3,7,11-trimethyl-2,6,10-dodecatriene-1-aldoxime.

Example 14C: GC-MS Analysis of 1,2-Benzenedicarboxylic acid, bis(2-methylpropyl) ester (diisobutyl phthalate)

GC-MS analyses of Tenax samples from the inner arm area of 28 volunteers were made for discrimination between samples extracted from active TB subjects and samples extracted from both healthy and Non-TB subjects. Control samples were also taken from the room in which the experiment was carried out. The results are given in FIG. 9 and in Table 14C are based on OpenChrom program in conjugation with Matlab software analysis:

TABLE 14C

GC-MS abundance of 1,2-Benzenedicarboxylic acid, bis(2-methylpropyl) ester from active TB and both healthy and non TB subjects

|  | Mean | Std Dev | Std Err Mean |
|---|---|---|---|
| Active | 0.9707 | 0.36611 | 0.10569 |
| Healthy and Non-TB | 2.29916 | 2.49629 | 0.62407 |
| Room | 1.81308 | 1.16533 | 0.18425 |

Figure 9:
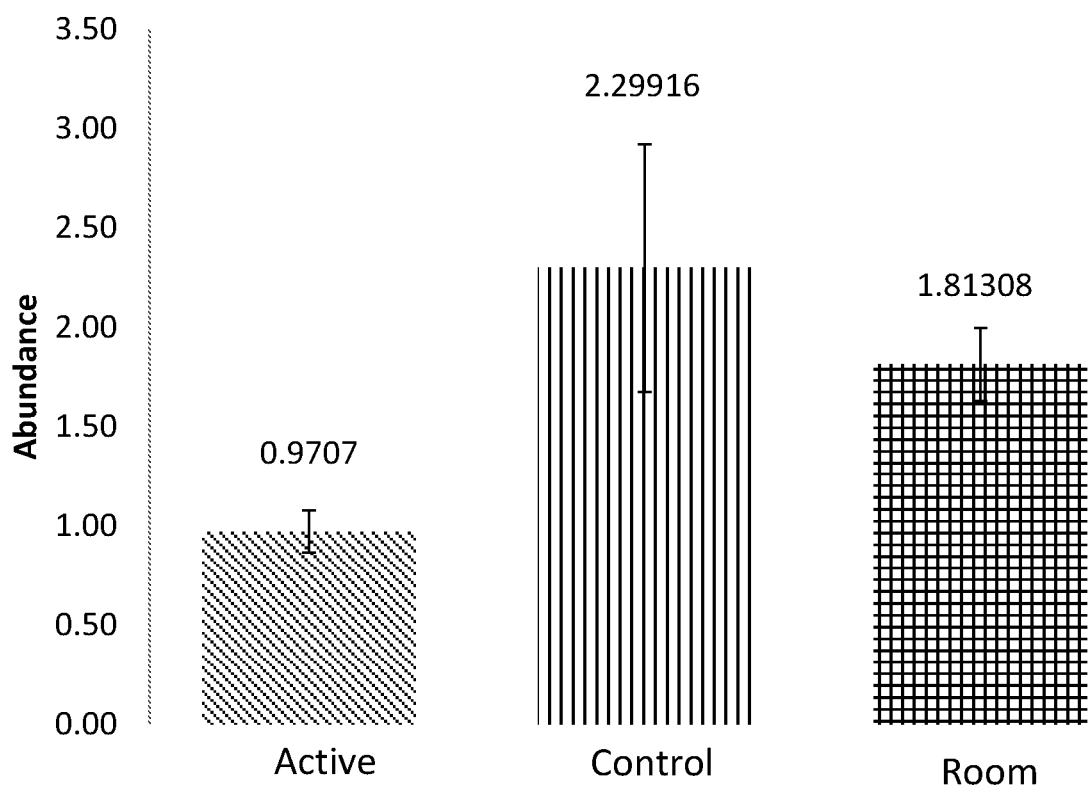
FIG. 9: Changes in abundance of 1,2-Benzenedicarboxylic acid, bis(2-methylpropyl) ester acquired by GC-MS analysis of samples from the inner arm area of 28 TB-afflicted volunteers (diagonal bar), non-TB subjects (vertical bar) and room air control sample (grid bar). The columns and error bars represent the mean abundance and standard error of mean (SEM), respectively. The values in are normalized by a factor of $10^6$

As seen from Table 14C and from FIG. 9, sample extracted from active TB subjects contain significantly less 1,2-Benzenedicarboxylic acid, bis(2-methylpropyl) ester than samples derived from both healthy and non TB subjects and room samples. The values in this table and figure are normalized by a factor of $10^6$.

According to Wilcoxon test, all the binary compressions between the three groups are significant with the p-value lower than 0.05 with the analysis of OpenChrom program in conjugation with Matlab software designed especially towards this study. However, Post-run program analysis shows no significant difference between the groups. This extreme difference between the analyses results can be explained by the programs ability to reduce and filter the external noise. The retention time of this VOC had a significant amount of noise that can adversely affect the ability of the discrimination between the studied groups. Specially developed software, able to deal with this problem and ignore the noise. 1,2-Benzenedicarboxylic acid, bis(2-methylpropyl) ester has not been reported as a TB-related VOC to date.

Tentative recognition according to their similarity index compared to a GC-MS search library, which includes the following compounds: phthalic acid, butyl ester, ester with butyl glycolate; di-n-octyl phthalate; Bis-(3,5,5-trimethylhexyl) phthalate; Phthalic acid, butyl undecyl ester; 1,2-benzenedicarboxylic acid, dihexyl ester; 1,2-benzenedicarboxylic acid, butyl octyl ester; phthalic acid, isobutyl octadecyl ester; 1,2-benzenedicarboxylic acid, butyl decyl ester; 1,2-benzenedicarboxylic acid, diisooctyl ester; 1,2-benzenedicarboxylic acid, dipropyl ester; phthalic acid, bis (7-methyloctyl) ester; 1,2-benzenedicarboxylic acid, butyl 2-ethylhexyl ester; phthalic acid, isohexyl 3-methylbut-2-en-1-yl ester; 1,2-benzenedicarboxylic acid, butyl 8-methylnonyl ester; phthalic acid, 4-cyanophenyl nonyl ester; 1,2-benzenedicarboxylic acid, diheptyl ester; phthalic acid, butyl tetradecyl ester; 1,2-benzenedicarboxylic acid, mono (2-ethylhexyl) ester; phthalic acid, isobutyl 3-methylbut-2-en-1-yl ester; 1,2-benzenedicarboxylic acid, decyl octyl ester; phthalic acid, butyl isohexyl ester; phthalic acid, isobutyl undecyl ester; phthalic acid, isohexyl pent-2-en-4-yn-1-yl ester;

Example 15: Nano-Sensor Array Analysis—DFA Analysis of Tenax Samples from the Inner Arm Area, South Africa A quadratic DFA analysis of Tenax samples from the inner arm area of the 196 volunteers was performed in the South African study. The complete study population included 92 volunteers with active TB and 104 non-TB and healthy volunteers (based on the collected Tenax Arm samples). The study population was divided into training group (70%) and test group (30%). The training group included 65 active TB cases and 78 non-TB and healthy cases. The test group included 27 TB cases and 31 non-TB and healthy cases.

A quadratic DFA model was applied and included 13 features for Tenax Arm samples. Prior probabilities were set to 0.1 for active TB and 0.9 non-TB and healthy. The DFA model was based on the following chemiresistors and their features:

1. 3-Ethoxythiophenol-Area under response feature
2. Decanethiol-based GNPs chemiresistor—delta R end feature
3. Decanethiol-based GNPs chemiresistor—delta R middle feature
4. Benzyl mercaptan-based GNPs chemiresistor—delta R end feature
5. Benzyl mercaptan-based GNPs chemiresistor—delta R peak feature
6. 2-Ethylhexanethiol-based GNPs chemiresistor—delta R end feature
7. 2-Ethylhexanethiol-based GNPs chemiresistor—delta R peak feature
8. A composite of black carbon with poly(propyleneurethaneureaphenyl-disulfide) PPUU-25-delta R end feature
9. 2-Ethoxythiophenol(2)-based GNPs chemiresistor—delta R end feature
10. Octadecanethiol-based GNPs chemiresistor—delta R middle feature
11. 2-Ethylhexanethiol-based GNPs chemiresistor—delta R middle feature
12. Decanethiol(2)-based GNPs chemiresistor—delta R middle feature 13. Decanethiol-based GNPs chemiresistor—delta R peak feature The delta R features and areas under curve are chemiresistor characteristics extracted from the responses of the sensors towards the sample. For each sensor there are 5 possible features. Delta R end feature, delta R peak feature and delta R middle feature refer to the resistance at the end, at the peak or at the middle of the exposure, respectively, minus the vacuum resistance prior to the exposure. The area under response feature refers to the area under the peak during the exposure.

The results are given in Table 15A:

TABLE 15A distinguishing between Active TB and non TB subjects (Tenax inner arm)

|  | Training (%) | Test (%) |
|---|---|---|
| Sensitivity | 95.4 | 92.6 |
| Specificity | 78.1 | 74.2 |
| Accuracy | 86.2 | 82.7 |

Confounding factors such as smoking, HIV and QFT statuses were tested and eliminated.

Further analysis, with the same DFA model, focused on HIV negative and QFT positive population (n=100). This analysis included TB positive (39) and TB negative samples (61). The results are given in Table 15B:

TABLE 15B distinguishing between Active TB and non TB subjects (Tenax inner arm, HIV negative and QFT positive)

|  | (%) |
|---|---|
| Sensitivity | 100 |
| Specificity | 85.2 |
| Accuracy | 91 |

Example 16: Nano-Sensor Array Analysis—DFA Analysis of Tenax Samples from the Chest Area, India A quadratic DFA analysis of Tenax samples from the chest area of the 286 volunteers was performed in the Indian study. The complete study population included 90 volunteers with active TB and 196 non-TB and healthy volunteers (based on the collected Tenax chest samples). The study population was divided into training group (70%) and test group (30%). The training group included 63 active TB cases and 137 non-TB and healthy cases. The test group included 27 TB cases and 59 non-TB and healthy cases.

A quadratic DFA model was applied and included 26 features for Tenax chest samples. Prior probabilities were set to 0.1 for active TB and 0.9 non-TB and healthy. The DFA model was based on the following chemiresistors and their features:

1. 1-Decanethiol-based GNPs chemiresistor—Area under response feature
2. 2-ethylhexanethiol-based GNPs chemiresistor—Area under response feature
3. Diketopyrrolopyrrole-naphthalene (TNT)—Area under response feature
4. Butanethiol-based GNPs chemiresistor—Area under response feature
5. 3-ethoxythiophenol-based GNPs chemiresistor—Area under response feature
6. 1-Decanethiol(2)-based GNPs chemiresistor—Area under response feature
7. 3-ethoxythiophenol(2)-based GNPs chemiresistor—Area under response feature
8. 4-chlorobenzene methanethiol-based GNPs chemiresistor—Area under response feature
9. Random networks (RNs) of carbon nanotubes (CNTs) with crystal hexa-perihexabenzocoronene (HBC) with C12 chemiresistor (HBC—C12)—Area under response feature
10. A composite of black carbon with poly(propylene-urethaneureaphenyl-disulfide) PPUU-2S mixed with poly(urethane-carboxyphenyl-disulfide) PUC-2S chemiresistor—Area under response feature
11. 3-ethoxythiophenol(3)-based GNPs chemiresistor—Area under response feature
12. Dibutyl Disulfide-based GNPs chemiresistor—Area under response feature
13. Dodecanethiol-based GNPs chemiresistor—Area under response feature
14. Octadecanethiol-based GNPs chemiresistor—delta R end feature
15. 2-ethylhexanethiol-based GNPs chemiresistor—delta R end feature
16. Diketopyrrolopyrrole-naphthalene (TNT)—delta R end feature
17. 3-ethoxythiophenol-based GNPs chemiresistor—delta R end feature
18. 1-Decanethiol-based GNPs chemiresistor—delta R end feature
19. 1-Decanethiol-delta R middle feature
20. Benzyl mercaptan-based GNPs chemiresistor—delta R middle feature
21. 1-Decanethiol-based GNPs chemiresistor—delta R middle feature
22. A composite of black carbon with poly(propylene-urethaneureaphenyl-disulfide) PPUU-2S chemiresistor—delta R middle feature
23. Tert-dodecanethiol-based GNPs chemiresistor—delta R peak feature
24. 2-ethylhexanethiol-based GNPs chemiresistor—delta R peak feature
25. 1-Decanethiol-based GNPs chemiresistor—delta R peak feature
26. 1-Decanethiol(2)—delta R peak feature The delta R features and areas under curve are chemiresistor characteristics extracted from the responses of the sensors towards the sample. For each sensor there are possible features. Delta R end feature, delta R peak feature and delta R middle feature refer to the resistance at the end, at the peak or at the middle of the exposure, respectively, minus the vacuum resistance prior to the exposure. The area under response feature refers to the area under the peak during the exposure.

The results are given in Table 16A:

TABLE 16A distinguishing between Active TB and
non TB subjects (Tenax chest)

| | Training (%) | Test (%) |
|---|---|---|
| Sensitivity | 87.3 | 88.8 |
| Specificity | 88.32 | 86.44 |
| Accuracy | 88 | 87.2 |

Confounding factors such as smoking, HIV and QFT statuses were tested and eliminated.

Further analysis, with the same DFA model, focused on HIV negative and QFT positive population (n=156). This analysis included TB positive (59) and TB negative samples (97). The results are given in Table 16B:

TABLE 16B distinguishing between Active TB and non TB subjects
(Tenax chest, HIV negative and QFT positive)

| | (%) |
|---|---|
| Sensitivity | 83 |
| Specificity | 85.9 |
| Accuracy | 91.9 |

Example 17: Fabrication of the Skin-Mountable Medical Device for Diagnosing and/or Monitoring Pulmonary Tuberculosis A skin-mountable device was fabricated. The skin-mountable device included a sensing unit and a flexible fixing unit. Dimensions of the sensing unit were 47 mm in length and 25 mm in width. The sensing unit included 16 sensors, including decanethiol-coated GNPs and hexanethiol-coated GNPs, which were prepared as detailed in the Materials and Methods section hereinabove. The sensors were exposed on one side of the sensing unit.

The sensing unit further included humidity and temperature sensors, a micro USB port and a rechargeable battery (having an operation maximum of 15 hours). The measurement range of the sensors of the sensing unit was 1K-1M Ohms. The sensing unit could further be operated via an electric cable.

The flexible fixing unit was a medical adhesive tape (i.e., a plaster). The sensing unit was attached to the flexible fixing unit with a side which did not include the exposed sensors.

Figure 10A:
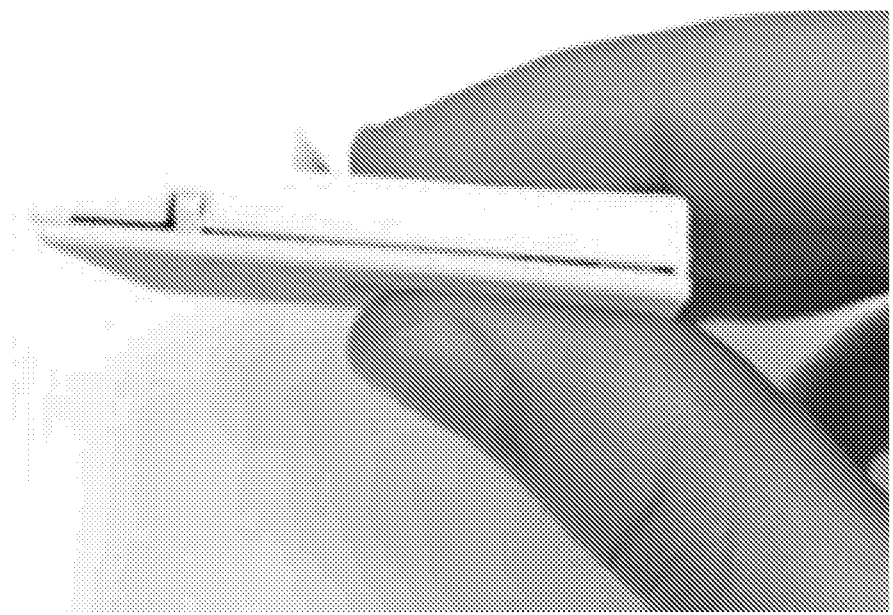
FIGS. 10A-10B: Photographs of the sensing unit of the skin mountable medical device according to some embodiments of the invention.
Figure 10B:
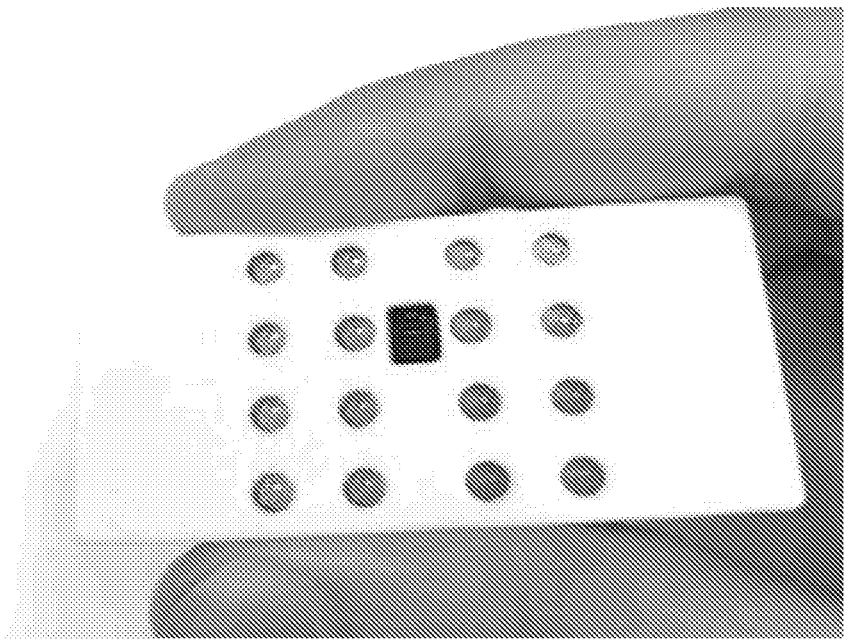

FIGS. 10A-10B show the photographs of the sensing unit of the skin-mountable device. The side with the exposed sensors, which is shown in FIG. 10B, was facing the skin of a subject when in use.

Figure 11:
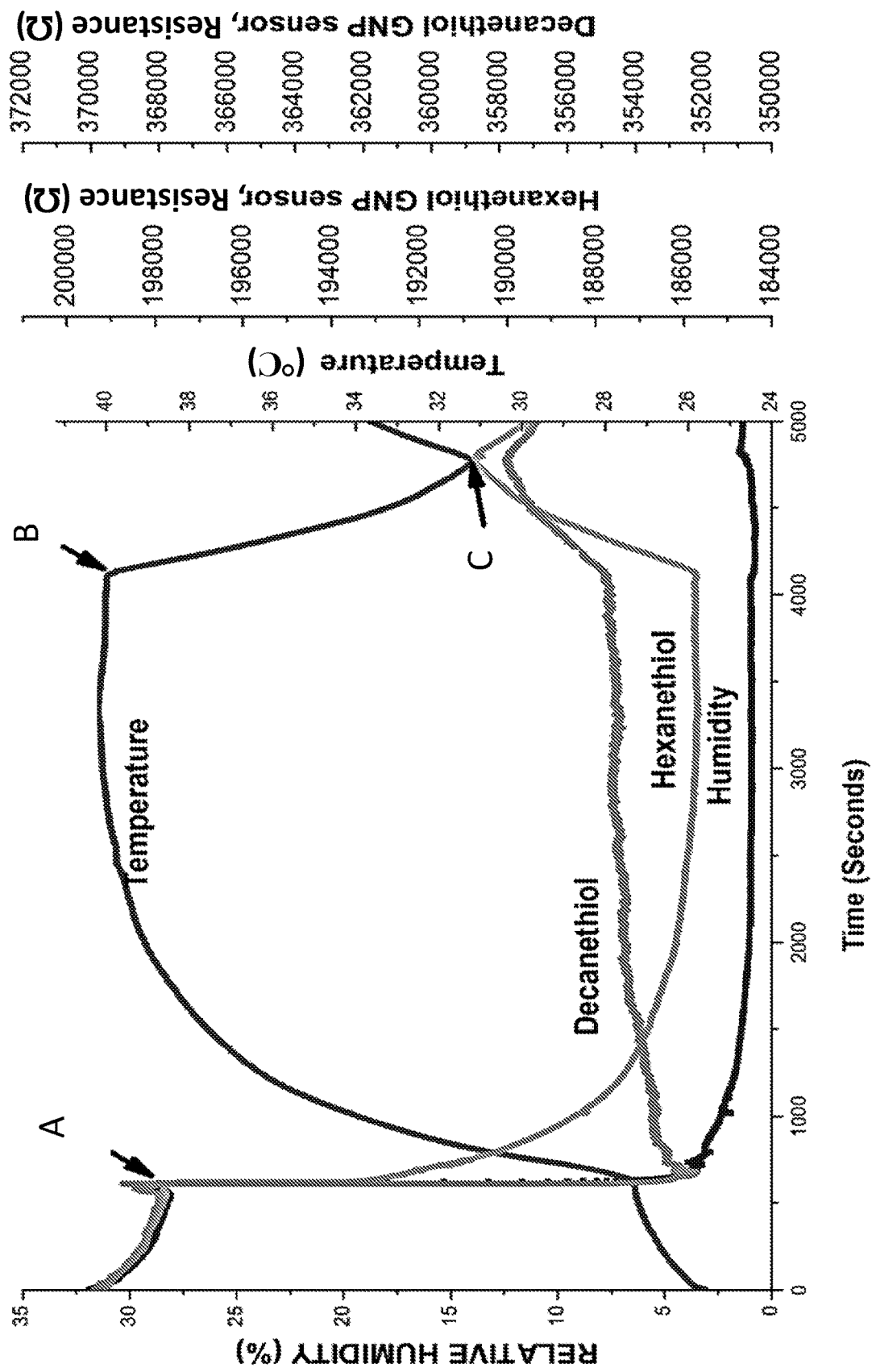
FIG. 11: Changes in the temperature, humidity, and resistance of the GNPs-based sensors, detected by the sensing unit shown in FIGS. 10A-10B, when placed on subject's skin.

The skin mountable medical device was placed on the skin with a humidity absorbent material ($CaSO_4$) and attached to the skin with the plaster. FIG. 11 presents the signals obtained from the sensors of the medical device before and during the time the device was attached to the skin. Point A on the graph indicates a time when the device was attached to the skin, point B indicates the addition of ice to lower the temperature of the device and point C indicates the removal of ice. It can be seen that there was a change in the signal of the humidity and temperature sensors when the device was attached to the skin (point A) and upon sudden change in the skin temperature due to ice addition and removal (points B and C, respectively). FIG. 11 further illustrates the change in the resistance of the GNPs-based sensors with decanethiol and hexanethiol surface chemistries, including a decrease in resistance when the sensing unit was attached to the skin.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A skin-mountable medical device for diagnosing and/or monitoring pulmonary tuberculosis in a subject, said device comprising:
    a flexible fixing strap;
    a sensing unit comprising at least one sensor comprising a conductive polymer composite comprising a disulfide polymer mixed with carbon black, wherein the disulfide polymer is selected from poly(propylene-urethaneureaphenyl-disulfide), poly(urethane-carboxyphenyl-disulfide) and combinations thereof; and
    at least one separation membrane that is hydrophobic and/or oleophobic,
wherein the flexible fixing strap has two opposing surfaces forming a structure comprising an internal face and an external face, wherein the sensing unit is disposed on said internal face and said internal face faces the skin of the subject during use, and
wherein the at least one separation membrane is disposed on the internal face of the flexible fixing strap, separates the at least one sensor from the skin, and provides a barrier between sweat emitted from the skin and the sensing unit.

2. The device of claim 1, further comprising at least one of (a) a processing unit, which receives an output signal of the at least one sensor and compares said signal to a reference value and (b) a transmitter, which receives the output signal of the at least one sensor and transmits said signal to a remote server and/or to a portable electronic device.

3. The device of claim 2, wherein at least one of the remote server and the portable electronic device comprises an algorithm, which compares the output signal of the at least one sensor to the reference value and/or an algorithm configured to differentiate between a response of the at least one sensor to skin-emitted or excreted volatile organic compounds (VOCs) or semi-volatile organic compounds (SVOCs) and a response of said at least one sensor to a stimulus selected from the group consisting of temperature, humidity, lateral strain, and combinations thereof.

4. A method for real-time diagnosing and/or monitoring pulmonary tuberculosis in a subject, the method comprising the steps of:
    (a) providing the skin-mountable medical device of claim 2;
    (b) mounting the skin-mountable medical device on the skin of the subject, thus exposing the at least one sensor to at least one volatile organic compound (VOC) or semi-volatile organic compound (SVOC) emitted or excreted from the skin;
    (c) measuring an output signal of the at least one sensor upon the exposure thereof to the at least one VOC or SVOC;
    (d) analyzing the output signal by at least one of the processing unit, the remote server and the portable electronic device; and (e) diagnosing tuberculosis if the output signal is greater than a reference value.

5. The method of claim 4, wherein the skin-mountable medical device is mounted on at least one of chest area skin, mastoid skin and brachium skin of the subject and wherein the step of measuring the output signal is performed after about 5 minutes to about 240 minutes following the step of mounting the skin-mountable medical device.

6. The method of claim 4, wherein the step of analyzing the output signal of the at least one sensor comprises extracting a plurality of response-induced parameters from said signal, the response-induced parameters being selected from the group consisting of full non-steady state response at the beginning of the signal, full non-steady state response at the beginning of the signal normalized to baseline, full non-steady state response at the middle of the signal, full non-steady state response at the middle of the signal normalized to baseline, full steady state response, full steady state response normalized to baseline, area under non-steady state response, area under steady state response, the gradient of the response upon exposure of the at least one sensor, and the time required to reach 10%, 20%, 30%, 40%, 50%, 60%, 70%, 80%, 90% or 100% of the response upon the exposure of the at least one sensor.

7. The device of claim 1, wherein the internal face comprises an adhesive, contacts the skin during use, and substantially isolates a skin area from the environment, when mounted on said skin area.

8. The device of claim 1, wherein the at least one sensor is configured in a form selected from the group consisting of a capacitive sensor, a resistive sensor, a chemiresistive sensor, an impedance sensor, and a field effect transistor sensor.

9. The device of claim 1, wherein the at least one separation membrane is made of a material selected from the group consisting of polytetrafluoroethylene (PTFE) polymers, polyethersulfone (PES) polymers, and derivatives thereof.

10. The device of claim 1, wherein the sensing unit comprises a sensor array, the sensor array comprising a plurality of sensors selected from the groups of sensors consisting of: dibutyl-disulfide-coated gold nanoparticles (GNPs), a composite of carbon black with poly(propylene-urethaneureaphenyl-disulfide), and 2-naphthalenethiol-based GNPs; hexakis(n-dodecyl)-peri-hexabenzocoronene (HBC—C12), a composite of black carbon with poly(propylene-urethaneureaphenyl-disulfide) mixed with poly(urethane-carboxyphenyl-disulfide), 2-ethylhexanethiol-coated GNPs, and diketopyrrolopyrrole-naphthalene copolymer (PDPP-TNT); Tert-dodecanethiol-coated GNPs, decanethiol-coated GNPs, 3-ethoxythiophenol coated GNPs, HBC—C12, and a composite of black carbon with poly(propylene-urethaneureaphenyl-disulfide) mixed with poly(urethane-carboxyphenyl-disulfide); a composite of carbon black with poly(propylene-urethaneureaphenyl-disulfide), tert-dodecanethiol-coated GNPs, a composite of black carbon with poly(propylene-urethaneureaphenyl-disulfide) mixed with poly(urethane-carboxyphenyl-disulfide), and 2-ethylhexanethiol-coated GNPs; a composite of carbon black with poly(propylene-urethaneureaphenyl-disulfide), tert-dodecanethiol-coated GNPs, 2-ethylhexanethiol-coated GNPs, decanethiol-coated GNPs, and 3-ethoxythiophenol-coated GNPs; a composite of carbon black with poly(propylene-urethaneureaphenyl-disulfide), decanethiol-coated GNPs, and 4-chlorobenzenemethanethiol-based GNPs; a composite of carbon black with poly(propylene-urethaneureaphenyl-disulfide), 2-naphthalenethiol-coated GNPs, and decanethiol-coated GNPs; a composite of carbon black with poly(propylene-urethaneureaphenyl-disulfide), 2-naphthalenethiol-coated GNPs, and decanethiol-coated GNPs; a composite of carbon black with poly(propylene-urethaneureaphenyl-disulfide), 2-naphthalenethiol-coated GNPs, and decanethiol-coated GNPs; a composite of carbon black with poly(propylene-urethaneureaphenyl-disulfide), 2-naphthalenethiol-coated GNPs, and decanethiol-coated GNPs; PDPP-TNT, and a composite of carbon black with poly(propylene-urethaneureaphenyl-disulfide); PDPP-TNT, dodecanethiol-coated GNPs, and a composite of carbon black with poly(propylene-urethaneureaphenyl-disulfide); PDPP-TNT, decanethiol-coated GNPs, HBC—C12, and a composite of carbon black with poly(propylene-urethaneureaphenyl-disulfide); PDPP-TNT, a composite of black carbon with poly(propylene-urethaneureaphenyl-disulfide) mixed with poly(urethane-carboxyphenyl-disulfide), 2-ethylhexanethiol-coated GNPs, and decanethiol-coated GNPs; PDPP-TNT, a composite of black carbon with poly(propylene-urethaneureaphenyl-disulfide) mixed with poly(urethane-carboxyphenyl-disulfide), 2-ethylhexanethiol-coated GNPs, HBC—C12, and hexanethiol-coated GNPs; PDPP-TNT, decanethiol-coated GNPs, tert-dodecanethiol-coated GNPs, a composite of black carbon with poly(propylene-urethaneureaphenyl-disulfide) mixed with poly(urethane-carboxyphenyl-disulfide), and 2-ethylhexanethiol-coated GNPs; hexanethiol-coated GNPs, a composite of carbon black with poly(propylene-urethaneureaphenyl-disulfide), dibutyl disulfide-coated GNPs, and 3-ethoxythiophenol-coated GNPs; and a composite of carbon black with poly(propylene-urethaneureaphenyl-disulfide), tert-dodecanethiol-coated GNPs, 3-ethoxythiophenol-coated GNPs, and 2-nitro-4-(trifluoromethyl)benzenethiol-coated GNPs.

* * * * *